(12) United States Patent
Bouchemal

(10) Patent No.: US 10,412,960 B2
(45) Date of Patent: Sep. 17, 2019

(54) MICROPARTICLES AND NANOPARTICLES MADE UP OF HYDROPHOBIZED POLYSACCHARIDES AND AN ALPHA-CYCLODEXTRINE

(71) Applicant: CENTRE NATIONAL DE LA RECHERCHE SCIENTIFIQUE, Paris (FR)

(72) Inventor: Kawthar Bouchemal, Palaiseau (FR)

(73) Assignees: CENTRE NATIONAL DE LA RECHERCHE SCIENTIFIQUE, Paris (FR); UNIVERSITE PARIS-SUD, Orsay (FR)

( * ) Notice: Subject to any disclaimer, the term of this patent is extended or adjusted under 35 U.S.C. 154(b) by 453 days.

(21) Appl. No.: 14/390,221

(22) PCT Filed: Apr. 5, 2013

(86) PCT No.: PCT/FR2013/000089
§ 371 (c)(1),
(2) Date: Oct. 2, 2014

(87) PCT Pub. No.: WO2013/150193
PCT Pub. Date: Oct. 10, 2013

(65) Prior Publication Data
US 2015/0151005 A1    Jun. 4, 2015

(30) Foreign Application Priority Data
Apr. 6, 2012  (FR) .................... 12 53242

(51) Int. Cl.
| | | |
|---|---|---|
| A61K 47/69 | (2017.01) | |
| A61K 51/12 | (2006.01) | |
| A61K 9/51 | (2006.01) | |
| A61K 9/16 | (2006.01) | |
| A01N 25/34 | (2006.01) | |
| B82Y 5/00 | (2011.01) | |
| A01N 43/16 | (2006.01) | |
| A61K 31/722 | (2006.01) | |
| A61K 31/727 | (2006.01) | |
| A61K 31/731 | (2006.01) | |
| A61K 47/61 | (2017.01) | |

(52) U.S. Cl.
CPC ............ *A01N 25/34* (2013.01); *A01N 43/16* (2013.01); *A61K 9/1652* (2013.01); *A61K 9/5161* (2013.01); *A61K 31/722* (2013.01); *A61K 31/727* (2013.01); *A61K 31/731* (2013.01); *A61K 47/61* (2017.08); *A61K 47/6951* (2017.08); *B82Y 5/00* (2013.01); *Y10T 428/2982* (2015.01)

(58) Field of Classification Search
CPC ............ A61K 47/48969; A61K 31/727; A61K 31/726; A61K 31/728; A61K 47/6951; A61K 51/1268; A61K 9/5161; A61K 9/1652
See application file for complete search history.

(56) References Cited

U.S. PATENT DOCUMENTS

| | | | | |
|---|---|---|---|---|
| 4,228,160 A | * | 10/1980 | Szejtli ................. | A61K 31/405 514/58 |
| 4,371,673 A | * | 2/1983 | Pitha ..................... | A61K 31/07 525/417 |
| 4,670,419 A | * | 6/1987 | Uda ...................... | A61K 47/40 514/10.1 |
| 4,696,918 A | * | 9/1987 | Stoddart ............... | A61K 31/28 514/58 |
| 7,682,635 B2 | * | 3/2010 | Gref ..................... | A61K 9/5161 424/499 |
| 2004/0109888 A1 | * | 6/2004 | Pun ...................... | A61K 9/0014 424/450 |
| 2005/0004348 A1 | | 1/2005 | Miyamoto et al. | |
| 2005/0203055 A1 | | 9/2005 | Zaneveld et al. | |
| 2008/0220030 A1 | | 9/2008 | Alonso et al. | |

FOREIGN PATENT DOCUMENTS

| | | |
|---|---|---|
| JP | 2003/267817 A | 9/2003 |
| WO | 2008/003685 A1 | 1/2008 |

OTHER PUBLICATIONS

Mourya, V. K., and Nazma N. Inamdar. "Chitosan-modifications and applications: opportunities galore." Reactive and Functional polymers 68.6 (2008): 1013-1051.*
Stella, Valentine J., and Roger A. Rajewski. "Cyclodextrins: their future in drug formulation and delivery." Pharmaceutical research 14.5 (1997): 556-567.*
Auzely-Velty, Rachel. "Self-assembling polysaccharide systems based on cyclodextrin complexation: Synthesis, properties and potential applications in the biomaterials field." Comptes Rendus Chimie 14.2-3 (2011): 167-177.*

(Continued)

*Primary Examiner* — Bethany P Barham
*Assistant Examiner* — Peter Anthopolos
(74) *Attorney, Agent, or Firm* — Young & Thompson

(57) ABSTRACT

Microparticles and nanoparticles of hydrophobized polysaccharide and an alpha-cyclodextrin, obtained by self-association in an aqueous medium, the hydrophobized polysaccharide being obtained by grafting of alkyl chains derived from fatty acids, by an acylation reaction. These microparticles and nanoparticles constitute systems used for encapsulating substances of interest, in particular in the pharmaceutical field, and vectorization thereof for therapeutic purposes.

13 Claims, 20 Drawing Sheets

(56) References Cited

OTHER PUBLICATIONS

Van De Manakker, Frank, et al. "Cyclodextrin-based polymeric materials: synthesis, properties, and pharmaceutical/biomedical applications." Biomacromolecules 10.12 (2009): 3157-3175.*
Fülöp, Z., et al. "Self-assembly of cyclodextrins: formation of cyclodextrin polymer based nanoparticles." Journal of Drug Delivery Science and Technology 22.3 (2012): 215-221.*
Layre, Anne-Magali, et al. "Tuning the interactions in cyclodextrin polymer nanoassennblies." European Polymer Journal 45.11 (2009): 3016-3026.*
Huh Kang Moo et al.: "Supramolecular hydrogel formation based on inclusion complexation between poly(ethylene glycol)-modified chitosan and alpha-cyclodextrin", Macromolecular Bioscience Feb. 20, 2004 LNKD-PUBMED:15468199, vol. 4, No. 2, Feb. 20, 2004 (Feb. 20, 2004), pp. 92-99, XP002685060, ISSN: 1616-5187 p. 92 p. 93, schema 1 p. 94; table 1 p. 94, left-hand column, paragraph 2 figure 9 p. 99, section "Conclusions".
Rinaudo M et al.: "Specific interactions in modified chitosan systems", Biomacromolecules, vol. 6. No. 5. Sep. 2005 (Sep. 2005), pp. 2396-2407. XP002685061, ISSN: 1525-7797, p. 2396. "introduction" p. 2397, section "Synthesis of Alkyl Chitosan" p. 2402-2403. section "(a) Interaction of Alkylated Chitosan and Free CD" figure 13.
Desbrieres J et al: "Hydrophobic Derivatives of Chitosan: Characterization and Rheological Behaviour", International Journal of Biological Macromolecules. Elsevier BV. NL, vol. 19. No. 1 Jan. 1, 1996 (Jan. 1, 1996). pp. 21-28 XP000944914, ISSN: 0141-8130. DOI: 10.1016/0141-8130(96)01095-1 the whole document.
Galant Celine et al.: "Altering associations in aqueous solutions of a hydrophobically modified alginate in the presence of beta-cyclodextrin monomers." The Journal of Physical Chemistry. B Jan. 12, 2006 LNKD-PUBMED:16471520, vol. 110. No. 1. Jan. 12, 2006 (Jan. 12, 2006). pp. 190-195. XP002685062, ISSN:1520-6106 abstract p. 190. left column. last phrase—right column. second paragraph p. 191. section "Synthesis and Solution Preparation" p. 194, section "Conclusions" figure 6.
Burckbuchler Virginie et al.: "Rheological and structural characterization of the interactions between cyclodextrin compounds and hydrophobically modified alginate" Biomacromolecules vol. 7. No. 6. Jun. 2006 (Jun. 2006), pp. 1871-1878, XP002685063, abstract figures 1.6.
Dowling M B et al.: "A self-assembling hydrophobically modified chitosan capable of reversible hemostatic action", Biomaterials Elsevier Science Ltd. UK, vol. 32, No. 13, May 2011 (May 2011), pp. 3351-3357, XP002685064, ISSN: 0142-9612 p. 3352, section 2.2 figure 4.
Karlberg Maria et al.: "Gels of hydrophobically modified hydroxyethyl cellulose cross-linked by amylose, Competition with cyclodextrin", Langmuir: The ACS Journal of Surfaces and Colloids Feb. 28, 2006 LNKDPUBMED: 16489813, vo 1. 22, No. 5, Feb. 28, 2006 (Feb. 28, 2006), pp. 2241-2248, XP002685065, ISSN: 0743-7463 abstract p. 2242, left-hand column, paragraph 1 p. 2242, section "Materials" p. 2248, section "Concluding Discussion".
Sashiwa H et al.: "Chemical modification of chitosan. 13.<1> Synthesis of organosoluble, palladium adsorbable, and biodegradable chitosan derivatives toward the chemical plating on plastics", Biomacromolecules 200209 US LNKDDOI: I0.I021/BM0200478, vol. 3, No. 5, Sep. 2002 (Sep. 2002), pp. 1120-1125, XP002685074, ISSN: 1525-7797 p. 1121, schema 1 et tableau 1.
Othman M et al.: "A comprehensive study of the spontaneous formation of nanoassemblies in water by a "lock-and-key" interaction between two associative polymers", Journal of Colloid and Interface Science, Academic Press, New York, NY, US, vo 1. 354, No. 2, Feb. 15, 2011 (Feb. 15, 2011), pp. 517-527, XP027580318, ISSN: 0021-9797 [retrieved on Dec. 30, 2010] the whole document.
Sihorkar V et al.: "Potential of polysaccharide anchored liposomes in drug delivery, targeting and immunization", Journal of Pharmacy and Pharmaceutical Sciences 2001 CA, vol. 4, No. 2, 2001, pp. 138-158, XP002698669, ISSN: 1482-1826 scheme 1: O-palmitoylPullulan.
International Search Report, dated Jun. 20, 2013, from corresponding PCT application.
FR Search Report, dated Oct. 11, 2014, from corresponding FR application.

* cited by examiner

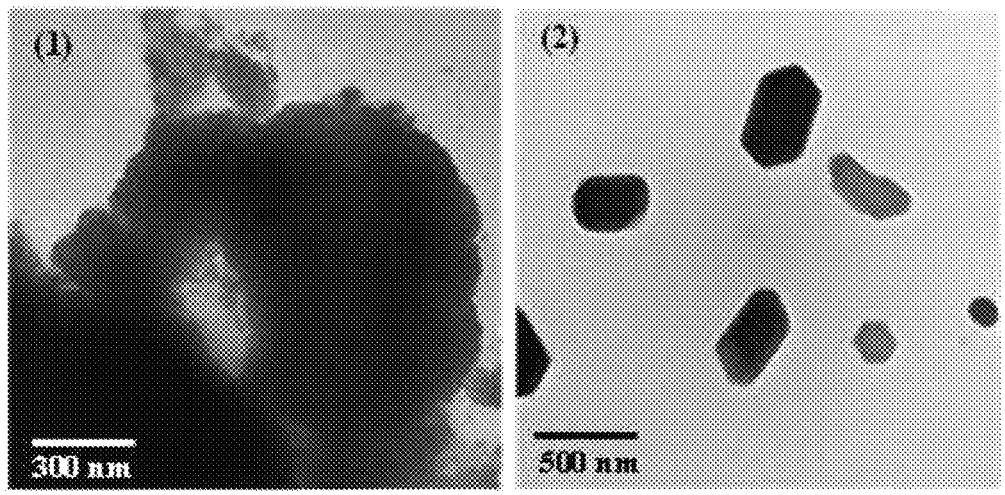
FIGURE 23
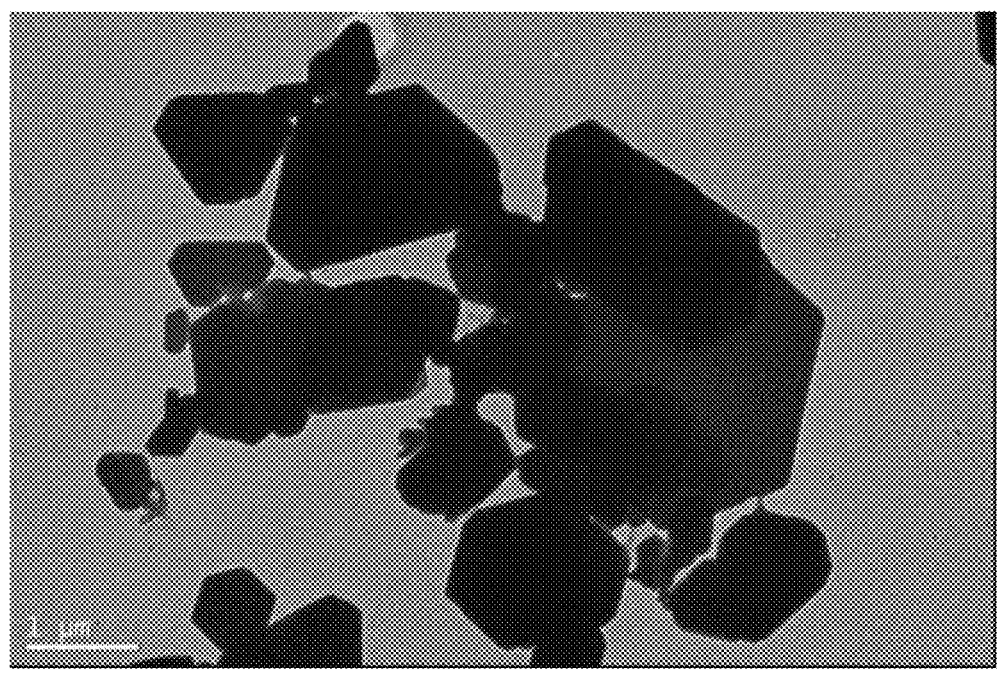
FIGURE 24 (1)

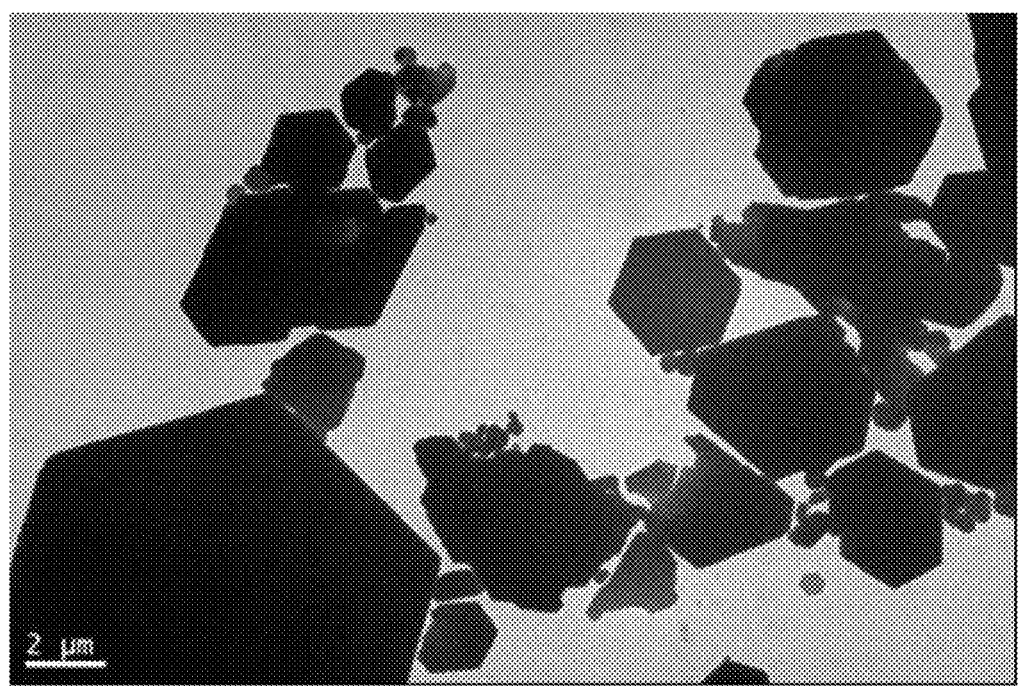
FIGURE 24 (2)

MICROPARTICLES AND NANOPARTICLES MADE UP OF HYDROPHOBIZED POLYSACCHARIDES AND AN ALPHA-CYCLODEXTRINE

The invention relates to microparticles and nanoparticles consisting of hydrophobized polysaccharides and an alpha-cyclodextrin.

The invention also relates to the use thereof as an encapsulation system.

At present, particles capable of containing and of vectorizing or encapsulating an active ingredient are the subject of active research. These particles must be capable of trapping a substance of interest, of conveying it in the body to the target cell or tissue, and then releasing it without any change in its structure. It is important that these particles are not toxic. However, there is a considerable drawback associated with their preparation. In fact, the latter often requires, in one step at least, the use of an organic solvent and/or the use of surfactants that are not biocompatible, sometimes under conditions of very high acidity. Removal of the molecules of solvent and/or of surfactant is often lengthy and incomplete, and adds a cost to the production of the particle. The toxic residual traces may moreover contribute to degradation of the active substances immobilized in the particles. This is why it is sought to produce these particles preferably in an aqueous medium, starting from polymers that are biocompatible and biodegradable.

The polysaccharides form a very useful class of polymers in the field of encapsulation. These polysaccharides include chitosan, chitin, hyaluronic acid and the glycosaminoglycans (GAGs).

Chitosan is a linear heteropolymer of N-acetyl-D-glucosamine and D-glucosamine joined together at β (1-4) according to the formula:

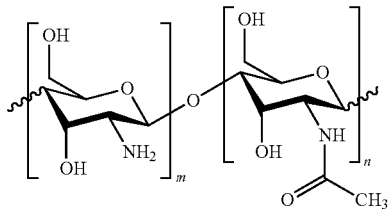

in which
m represents the number of D-glucosamine units,
n represents the number of N-acetyl-D-glucosamine units,
provided that the percentage of m relative to the total number of units is greater than 50%.

It has the advantage of being biocompatible and mucoadhesive. Chitosan nanoparticles have been used as adjuvants for vaccination by the mucosal route in animals (*Annales de Médecine Vétérinaire*, 2003, 147, 343-350). An adjuvant is a substance which, when it is administered at the same time as an antigen, increases the immune response to this antigen. The advantage of vaccination by the mucosal route is the introduction of an immune response at the point of entry of microbes. Vaccines administered alone by the mucosal route have a low bioavailability. They must be co-administered with substances that promote their penetration or with adjuvants.

Chitin is a linear heteropolymer of N-acetyl-D-glucosamine and D-glucosamine joined together at β (1-4) according to the formula:

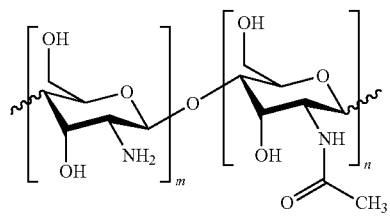

in which
m represents the number of D-glucosamine units,
n represents the number of N-acetyl-D-glucosamine units,
provided that the percentage of m relative to the total number of units is below 50%.

Chitin is a powerful hydrating agent, an effective scavenger of heavy metals, which are responsible for a great many contact allergies. It is used in the treatment of burns as it has wound-healing properties. Chitin is also used for filtering wastewater: it forms ionizable chains, allowing fixation of organic elements. It is also used in the food industry (manufacture of juice), as a processing aid.

One of the first steps in the colonization of biotic surfaces by microbes involves their interaction with receptors located at cellular level such as the glycosaminoglycans (GAGs), in particular heparin, heparan sulphate, hyaluronic acid, dermatan sulphate, keratan sulphate and chondroitin sulphate. Numerous viruses, bacteria, fungi and parasites are capable of binding to the GAGs present on the surface of the cells, thus facilitating their initial attachment and then entry into the cell followed by infection. Data from the literature indicate that the inhibitory effect of heparin, heparan sulphate, dermatan sulphate and chondroitin sulphate has been demonstrated on the human herpes simplex virus (HSV) (*Journal of Bacteriology*, 1964, 87(5), 1060-1066, *Virology.* 1995, 208(2), 531-539, *Journal of Virology.* 1989, 63(1), 52-58), whereas the binding of particles imitating the human papillomavirus (HPV) to cells was inhibited by heparin (*The Journal of Biological Chemistry.* 1999, 274(9), 5810-5822). Moreover, heparan sulphate has been found to play an important role in the prevention of infections by HPV-16 (*Journal of Virology.* 2009, 83(5), 2067-2074).

Heparin coating of abiotic surfaces has enabled bacterial adhesion to be reduced by 90% (*Journal of Urology.* 1987, 138, 423-426). GAGs and the sulphated polysaccharides have shown antibacterial activity against: *Staphylococcus aureus, Gardnerella vaginalis, Mycobacterium tuberculosis, Listeria monocytogenes, Neisseria gonorrhoeae, Helicobacter pylori, Yersinia enterocolitica, Mycoplasma pneumoniae, Streptococcus mutans, Chlamydia trachomatis, Staphylococcus aureus, Escherichia coli, Pseudomonas aeruginosa* (US 2005/0203055).

Heparin coating of abiotic surfaces has made it possible to reduce the adhesion of *Candida albicans* by approximately 50% (*Infection and Immunity.* 1993, 61(11), 4560-4568).

US patent 2005/0203055 has shown that cellulose sulphate has:
 antiviral properties against human immunodeficiency virus (HIV), HSV, HPV, bovine papillomavirus (BPV)
 antiparasitic properties against *Trichomonas vaginalis,*
 antifungal properties against *Aspergillus niger* and *Candida albicans.*

Other sulphated polysaccharides such as cellulose sulphate, carrageenan, dextran sulphate, and dextrin sulphate have shown antimicrobial activity.

Hyaluronic acid helps to protect the joints by increasing the viscosity of synovial fluid and by making cartilage more elastic. Hyaluronic acid is the only non-sulphated GAG. Hyaluronic acid is a natural constituent of the dermis and plays an important role in hydration, tonicity and elasticity of the skin.

Polysaccharides grafted with hydrophobic chains are amphiphilic systems capable of spontaneous self-association in an aqueous medium in the form of micelles of the core-corona type that can accommodate an active ingredient (*Drug Discovery Today*, 2012, 17, 623-629). However, their solubility in aqueous media decreases owing to the presence of the hydrophobic grafted chains.

The use of cyclic polysaccharides, such as cyclodextrins, leads to the formation of particles constituting inclusion systems that are soluble in aqueous media. These systems, of variable size and structure, ranging from nanoparticle to hydrogel, are capable of vectorization a substance of interest.

Gref et al. (US2005/004348A1) describe particles obtained by grafting one or more (for example two) cyclic polysaccharides, such as beta-cyclodextrin, onto a biodegradable polymer such as poly(ε-caprolactone) and use thereof as vectors of active substances. In this case, the cyclic polysaccharide is bound covalently to the biodegradable polymer. This same patent describes the formation of nanoparticles by mixing a dextran bearing lauryl chains and a beta-cyclodextrin polymer.

Bochot et al. (US2006/0188464A1; EP1590077B1; *International Journal of Pharmaceutics*, 2007, 339, 121) describe, in their publication and their applications, beads varying in size from 1 to 3 mm, obtained by mixing an oil and a solution of alpha-cyclodextrin. They do not use linear polysaccharides described above and, moreover, the particle size formed is in the millimeter range.

One of the aims of the invention is to supply inclusion complexes between a polysaccharide and a cyclodextrin.

Another aim of the invention is to propose microparticles or nanoparticles formed from the aforesaid inclusion complexes.

Another aim is to supply a simple method for the preparation of said particles without necessarily using surfactants or organic solvents.

In addition, the invention relates to the use of said particles as such, without necessarily adding substance(s) of interest.

The invention relates to the use of said particles for encapsulating one or more substance(s) of interest.

The invention relates to an inclusion complex formed between:
- a polysaccharide comprising hydrophobic groups bound covalently to said polysaccharide,
- a cyclodextrin (CD) in the form of monomer, the polysaccharide and the cyclodextrin being bound non-covalently.

According to another advantageous aspect, the invention relates to an inclusion complex formed by the interaction between:
- a polysaccharide comprising hydrophobic groups bound covalently to said polysaccharide,
- and a cyclodextrin (CD) in the form of monomer, the polysaccharide and the cyclodextrin being bound non-covalently.

The term "inclusion complex" denotes a system that results from the interaction of a "host" molecule that allows within its cavity one or more other "guest" molecules without any covalent bond being established.

The term "polysaccharide" denotes a carbohydrate macromolecule formed by the chain formation of a large number of elementary sugars. The majority of the polysaccharides are hydrophilic, they carry —OH and/or —NH$_2$, and/or —COOH, and/or —CH$_2$—OH, and/or —SO$_3^-$ groups, or groups derived from the latter. The nature of these groups allows them to be differentiated from a structural standpoint and from the standpoint of the physicochemical and biological properties. In this case the term "polysaccharide" denotes a linear or branched polysaccharide.

The expression "polysaccharide comprising hydrophobic groups" means that the polysaccharide has been "hydrophobized" by grafting, on the —OH and/or —NH$_2$, and/or —COOH, and/or —CH$_2$—OH, and/or —SO$_3^-$ groups, of alkyl chains that are naturally hydrophobic owing to their non-polar character. The "polysaccharide comprising hydrophobic groups" is therefore an amphiphilic polysaccharide. Under certain conditions, these polysaccharides are capable of self-association, forming micelles of the core-corona type in aqueous media (*Drug Discovery Today*, 2012, 623-629).

A "cyclodextrin" (or cycloamylose) is a cyclic oligosaccharide of β-D-glucopyranose joined together by α(1-4) bonds. It is a cage molecule of natural origin that makes it possible to encapsulate various molecules, in particular molecules of therapeutic interest. There are various sizes, each having the shape of a "lampshade". It bears hydrophilic groups (—OH) located on the outside, the assembly delimiting a relatively hydrophobic cavity. This amphiphilic character allows cyclodextrin to enclose hydrophobic molecules within its cavity, to form water-soluble inclusion complexes. Its biodegradable nature predisposes it to important applications in the areas of agri-food, cosmetics and pharmaceuticals. Encapsulation in cyclodextrins in fact makes it possible to protect fragile molecules or ensure slow and controlled release thereof.

Using alpha-cyclodextrin instead of a cyclodextrin polymer represents an obvious advantage from the economic and regulatory standpoint as this cyclodextrin is commercially available and is a recognized pharmaceutical excipient, accepted by the majority of pharmacopoeias.

The expression "the polysaccharide and the cyclodextrin being bound non-covalently" means that the interactions between these two molecules are van der Waals bonds and/or hydrogen bonds, and/or electrostatic bonds, and/or hydrophobic bonds, and not covalent bonds.

These inclusion complexes are thus formed exclusively by non-covalent bonds by simple mixing of alpha-cyclodextrin and polysaccharide grafted with hydrophobic groups. Thus, by using the same procedure and by varying the type of these non-covalent interactions, particles of varied size and structure may be formed.

The invention thus relates to an inclusion complex formed by the interaction between at least:
- a polysaccharide selected from chitosan, dextran, hyaluronic acid, amylose, amylopectin, pullulan, heparin, chitin, heparan sulphate, dermatan sulphate, keratan sulphate, chondroitin sulphate, cellulose sulphate, dextran sulphate, dextrin sulphate, starch, pectin, the alginates, the carrageenans, fucan, curdlan, xylan, polyguluronic acid, xanthan, arabinan, polymannuronic acid, and derivatives thereof, said polysaccharide comprising hydrophobic groups selected from linear or branched alkyl groups containing from 2 to 1000 carbon atoms, or linear or branched, in particular linear, alkenyl groups, which may contain at least one C═C double bond, said hydrophobic groups being bound covalently to said polysaccharide, and an α-cyclodextrin (CD) in the form of monomer, the polysaccharide and the cyclodextrin being bound non-covalently.

Advantageously, in the inclusion complex according to the invention, the polysaccharide is made up of at least 3 saccharide units, its molecular weight being in particular in the range from 100 Da to 1,000,000 kDa, and in particular is equal to 20 kDa, 145 kDa or 250 kDa.

According to another aspect, in the inclusion complex according to the invention, the polysaccharide is made up of at least 3 saccharide units, its molecular weight being in particular in the range from 5 kDa to 100,000 kDa, and in particular is equal to 20 kDa, 145 kDa or 250 kDa.

Advantageously, the ratio of the concentration of the cyclodextrin to the concentration of the polysaccharide is in the range from $10^{-6}$ to 900,000, in particular in the range from 4 to 15, and in particular is equal to 10.

According to another aspect, the ratio of the concentration of the cyclodextrin to the concentration of the polysaccharide is in the range from 0.01 to 1500, in particular in the range from 4 to 15, and in particular is equal to 10.

This parameter is very important as it makes it possible to modulate the particle size obtained from the aforesaid inclusion complex by altering the ratio of the concentration of the cyclodextrin to that of the polysaccharide.

The average particle size might increase when the ratio of the concentration of the cyclodextrin to the concentration of the polysaccharide decreases.

If the ratio is less than 0.01, no particles are formed. If the ratio is greater than 20, particles are formed. Above a concentration ratio of 1500, and in particular for a concentration above 50 g/L, alpha-cyclodextrin is no longer water-soluble.

The solubility of the polysaccharide is not a limiting factor in formation of the particles, as the latter form even if the polysaccharide is used in the form of a suspension in water. Being able to use a polysaccharide in the form of suspension for formulating nanoparticles and microparticles has the advantage that more-concentrated particles are obtained. With this new technology, polysaccharides that were difficult to formulate as nanoparticles or microparticles on account of their problems of solubility in water (in particular chitin) thus find new applications.

Advantageously, this method is simple, and it reduces pollution of the environment, because it is not essential to use solvents, surfactants or reagents. It also lowers energy consumption. It does not necessarily use a heating step if a purification step is carried out after their preparation.

Advantageously, the polysaccharides retain their properties, in particular antimicrobial, even after they are formulated as nanoparticles and microparticles.

The invention relates in particular to an inclusion complex in which the polysaccharide is selected from chitosan, dextran, hyaluronic acid, amylose, amylopectin, pullulan, heparin, chitin, cellulose derivatives, heparan sulphate, dermatan sulphate, keratan sulphate, chondroitin sulphate, cellulose sulphate, dextran sulphate, dextrin sulphate, starch, pectin, the alginates, the carrageenans, fucan, curdlan, xylan, polyguluronic acid, xanthan, arabinan, polymannuronic acid, and derivatives thereof, and is in particular chitosan.

They may be neutral (dextran for example), or may have an overall positive charge (chitosan for example) or negative charge (heparin, hyaluronic acid, pectin).

In a particular aspect of the invention, the polysaccharides have intrinsic properties even without adding active molecules. Chitosan has the advantage of being biocompatible and mucoadhesive, and may be used as adjuvant for vaccination by the mucosal route. Chitin has hydrating and wound-healing properties and is able to capture heavy metals and purify wastewater. The GAGs and the sulphated polysaccharides have activity for preventing, inhibiting and/or treating fungal, bacterial, viral and/or parasitic infections on biotic or abiotic surfaces. Hyaluronic acid is known to promote hydration, tonicity and elasticity of the skin and to protect the joints by increasing the viscosity of the synovial fluid and by making the cartilage more elastic.

These polysaccharides are able to prevent and inhibit the formation of biofilms. A biofilm is defined as an organized community of cells fixed to a biotic or abiotic surface, incorporated in extracellular material. The biofilms are the predominant form of life of microorganisms and constitute a means by which the latter display resistance to antimicrobial agents. They can colonize biotic surfaces such as the surface of cells, tissues or organs (for example the skin and the buccal, nasal, ocular, aural, vaginal, and rectal mucosae and/or the digestive system) or abiotic surfaces such as plastic, glass, metal or any other material on which microorganisms can develop.

According to another particular embodiment, in the inclusion complex of the invention, the degree of substitution of the polysaccharide with hydrophobic groups is from 0.001 to 100%, in particular from 0.05 to 50%.

According to another particular embodiment, in the inclusion complex of the invention, the degree of substitution of the polysaccharide with hydrophobic groups is from 0.1 to 70%, in particular equal to 2%, 13% or 17%.

The degree of substitution reflects the number of hydrophobic groups bound to 100 saccharide units of the polysaccharide chain. It is determined by the experimental conditions of grafting and can be measured by nuclear magnetic resonance (NMR) or by elemental analysis for example.

It is also a parameter allowing the average particle size formed from the inclusion complexes to be modulated. When the degree of substitution increases, their average size may decrease or increase, depending on the polysaccharide used.

According to a particular embodiment, in the inclusion complex of the invention, the hydrophobic groups are linear or branched, in particular linear, alkyl groups containing from 2 to 1000 carbon atoms, or linear or branched, in particular linear, alkenyl groups, which may contain at least one C═C double bond.

According to another particular embodiment, in the inclusion complex of the invention, the hydrophobic groups are linear or branched, in particular linear, alkyl groups containing from 2 to 20 carbon atoms, or linear or branched, in particular linear, alkenyl groups containing 2 to 20 carbon atoms and bearing from 1 to 4 C═C double bonds, conjugated or not.

According to a particular embodiment, the hydrophobic groups are not aromatic groups.

The fatty acids used for grafting the hydrophobic chains on the polysaccharide are in particular lauric acid, palmitic acid, oleic acid, stearic acid, linoleic acid, this list in no case being exhaustive and limiting.

| Fatty acid | Formula |
|---|---|
| | 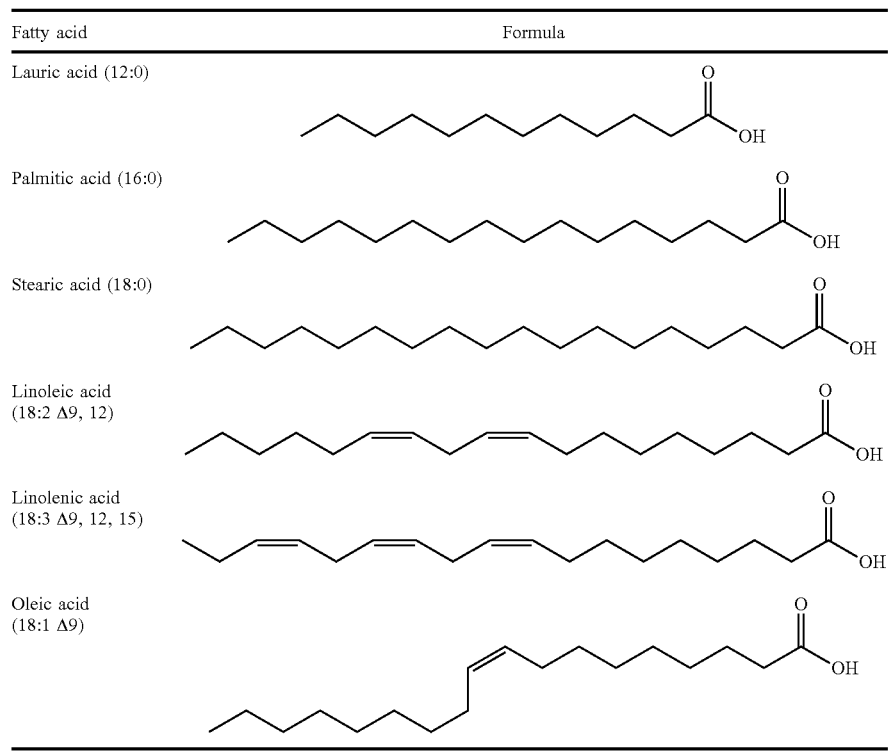 |

According to a particular embodiment, in the inclusion complex of the invention, the hydrophobic groups are fixed covalently to the polysaccharide by a nitrogen atom of said polysaccharide.

This applies to polysaccharides comprising amino groups, in particular chitosan and heparin. These amino groups may undergo a reaction of N-acylation by reaction with a fatty acid or a fatty acid derivative such as a fatty acid chloride or a fatty acid anhydride.

According to another particular embodiment, in the inclusion complex of the invention, the hydrophobic groups are fixed covalently to the polysaccharide by one or more oxygen atoms of said polysaccharide.

According to another particular embodiment, in the inclusion complex of the invention, the hydrophobic groups are fixed covalently to the polysaccharide by one or more oxygen atoms of said polysaccharide, and in particular at the level of the carboxyl function COOH, and/or of a group $CH_2$—OH and/or —$SO_3^-$ of said polysaccharide.

There are many —OH groups on the polysaccharides. They react with the fatty acids or fatty acid derivatives such as the acid chlorides and the acid anhydrides, to give esters. The hydrophobic group of the fatty acid or fatty acid derivative is therefore grafted to the polysaccharide by one of its oxygen atoms, in the form of an acyl group: this is an "O-acylation" reaction.

The O-acylation reaction leads to the formation of ester bonds that are easily degraded by esterases after administration in vivo.

According to another embodiment of the invention, in the inclusion complex of the invention, the hydrophobic groups are fixed covalently to the polysaccharide by a nitrogen, phosphorus or sulphur atom and by oxygen atoms of said polysaccharide in the proportions from 0.001 to 100%.

According to another embodiment of the invention, in the inclusion complex of the invention, the hydrophobic groups are fixed covalently to the polysaccharide by a nitrogen, phosphorus or sulphur atom and by oxygen atoms of said polysaccharide in the proportions from 0.5 to 20%.

When the polysaccharide contains amino groups and hydroxyl groups, by reaction with fatty acids or fatty acid derivatives such as acid chlorides and acid anhydrides, it may undergo both N-acylation and O-acylation. However, the amino groups are more reactive than the hydroxyl groups.

When methanesulphonate is used, O-acylation of chitosan is predominant.

According to another embodiment, in the inclusion complex of the invention, the cyclodextrin CD has the formula:

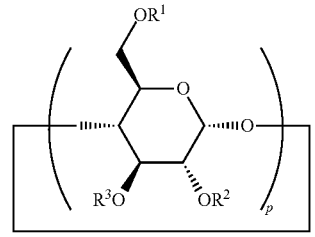

in which
  p is an integer equal to 6,
  $R^1$, $R^2$ and $R^3$, which may be identical or different, in particular identical, are hydrogen atoms, alkyl groups comprising 1 to 3 carbon atoms, selected from methyls, ethyls, propyls, isopropyls, —$NH_2$ amino groups, —$NH_3^+$ ammonium groups, or —$SO_4^{2-}$ sulphate groups, and are in particular hydrogen atoms or methyl groups, said CD being alpha-cyclodextrin (α-CD) in the form of monomer.

The "cyclodextrins" (CD) are cyclic oligomers of β-D-glucopyranoses joined together by α(1-4) bonds. Three families are mainly used. They are the α-, β- and γ-cyclodextrins formed respectively from 6, 7 or 8 glucopyranose subunits.

p=6 corresponds to α-cyclodextrin; p=7 corresponds to β-cyclodextrin and p=8 corresponds to γ-cyclodextrin. They are shown diagrammatically below:

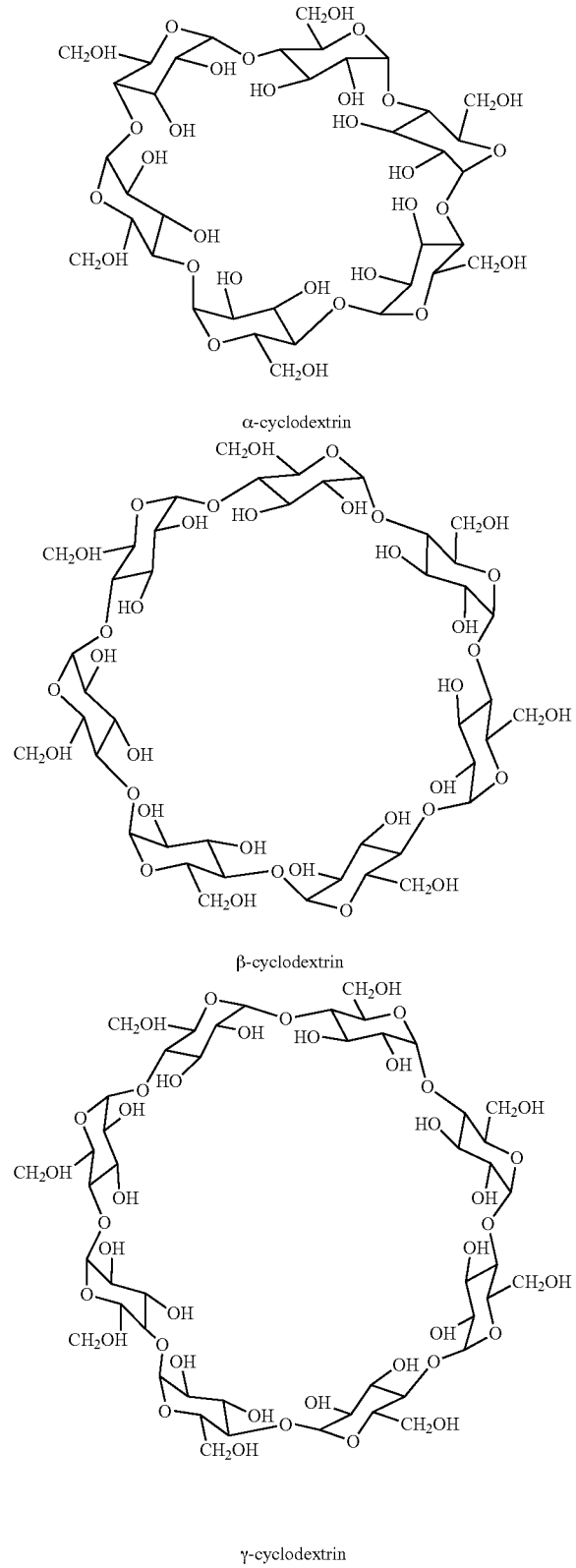

Their geometry is comparable to a truncated cone delimiting a cavity at its centre. It is described in FIG. 15.

There are therefore cage molecules, capable of receiving molecules by inclusion, species in particular of a hydrophobic nature. The size of the cavity depends on the nature of the cyclodextrin. The internal portion of the cavity is hydrophobic, and the external portion is hydrophilic.

The —OH groups may be substituted, in particular with methyl, hydroxypropyl or sulphobutyl groups. The substitutions may increase the solubility of the cyclodextrin.

The only cyclodextrin used in the invention is α-cyclodextrin. The advantage of this cyclodextrin is connected with its small size, which allows it to interact with the hydrophobic chains bound to the polysaccharide.

According to a particular embodiment, in the inclusion complex of the invention, the cyclodextrin is functionalized with a ligand selected from antibodies, antibody fragments, receptors, lectins, biotin or derivatives thereof.

The term "ligand" denotes a molecule capable of binding covalently to CD.

The ligand is selected from proteinaceous compounds in particular involved in the recognition and/or neutralization of pathogenic agents (antibodies or antibody fragments, receptors, lectins), involved in the metabolism of fatty acids (biotin and derivatives).

According to another particular aspect, in the inclusion complex of the invention, the cyclodextrin is charged or uncharged.

According to yet another aspect, in the inclusion complex of the invention, the cyclodextrin is substituted or unsubstituted.

By "substituted cyclodextrin" is meant for example a cyclodextrin substituted with an alkyl group, for example a methylated cyclodextrin, with a hydroxyalkyl group, with a maltosyl group, with a galactosyl group, or with any other molecules.

According to another particular embodiment of the invention, in the inclusion complex:
the polysaccharide is a chitosan bearing hydrophobic groups,
the cyclodextrin is α-CD.

Chitosan, a linear polysaccharide of natural origin, composed randomly of D-glucosamine deacetylated units bound at β-(1-4) to N-acetyl-D-glucosamine acetylated units, is produced by chemical or enzymatic deacetylation of chitin. Chitosan is biocompatible and biodegradable. It is non-toxic, and bio-adhesive owing to interaction between the positive charges in acid medium (pH<6.0-6.5) carried by the amine functions and the negative charges carried by the biological membranes. It also displays antibacterial and antiviral activity.

Chitosan is soluble in an aqueous solution of acetic acid at low concentration by protonation of the amino groups present. The glucoside chain of chitosan is essentially hydrophilic. However, it is possible to graft groups, in particular hydrophobic groups, on the amino and hydroxyl groups. The polysaccharide then becomes amphiphilic and can form micelles, nanoparticles but also hydrogels at higher concentration by self-association in aqueous media. It is therefore possible to encapsulate active ingredients in the objects that it forms. It may be used for encapsulating active ingredients (paclitaxel, ibuprofen, etc.).

According to another embodiment, in the inclusion complex of the invention, chitosan bears hydrophobic groups grafted at the level of certain nitrogen atoms and has the formula:

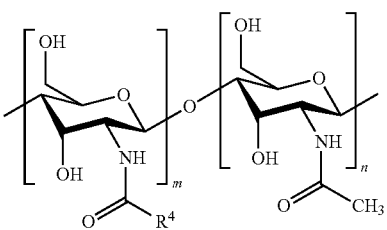

in which
m represents the number of deacetylated units,
n represents the number of acetylated units,
provided that the degree of deacetylation (DDA) representing the percentage of m relative to the total number of units is greater than 50%,
$R^4$ represents the hydrophobic group and is selected from:
- a linear or branched alkyl group containing from 1 to 20 carbon atoms, in particular the $-(CH_2)_{14}-CH_3$ or $-(CH_2)_{16}-CH_3$ groups,
- a linear or branched alkenyl group containing 2 to 20 carbon atoms and bearing from 1 to 4 C=C double bonds, conjugated or not, in particular the $-(CH_2)_7-CH=CH-CH_2-(CH_2)_7-CH_3$ or $-(CH_2)_7-CH=CH-(CH_2)_7-CH_3$ groups.

According to another embodiment, in the inclusion complex of the invention, chitosan bears hydrophobic groups grafted at the level of certain nitrogen atoms and has the formula

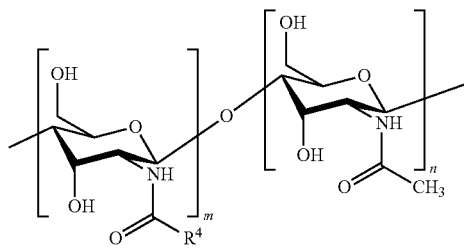

in which
m represents the number of D-glucosamine units,
n represents the number of N-acetyl-D-glucosamine units,
provided that the degree of deacetylation (DDA) representing the percentage of m relative to the total number of units is greater than 50%,
$R^4$ represents the hydrophobic group and is selected from:
- a linear or branched alkyl group containing from 1 to 1000 carbon atoms, in particular the $-(CH_2)_{14}-CH_3$ or $-(CH_2)_{16}-CH_3$ groups,
- a linear or branched alkenyl group containing 2 to 1000 carbon atoms and containing at least one C=C double bond, in particular the $-(CH_2)_7-CH=CH-CH_2-(CH_2)_7-CH_3$ or $-(CH_2)_7-CH=CH-(CH_2)_7-CH_3$ groups.

DDA of 50% denotes the boundary between chitin and chitosan: when the DDA is below 50%, it is called chitin, otherwise it is called chitosan.

The $-(CH_2)_{14}-CH_3$ group is derived from palmitic acid, $-(CH_2)_{16}-CH_3$ is derived from stearic acid, $-(CH_2)_7-CH=CH-CH_2-(CH_2)_7-CH_3$ is derived from linoleic acid, $-(CH_2)_7-CH=CH-(CH_2)_7-CH_3$ is derived from oleic acid.

The N-acylated chitosan is obtained from a reaction of the N-acylation type in the presence of a coupling agent, EDCI (1-ethyl-3-(3-dimethylaminopropyl)carbodiimide), which reacts with the carboxyl groups of the fatty acid (oleic or palmitic for example) to form an intermediate ester capable of binding to the free amino functions of the chitosan (Lee, K. Y., et al., *Structural Determination and Interior Polarity of Self-Aggregates Prepared from Deoxycholic Acid-Modified Chitosan in Water*, Macromolecules, 1998, 31, 2, 378-383). The following diagram shows the succession of reactions carried out in order to obtain an N-acylated chitosan, grafted with chains derived from oleic acid. The same procedure is followed with the other fatty acids such as palmitic acid for example.

Scheme: N-acylation of chitosan with oleic acid in the presence of EDCI.

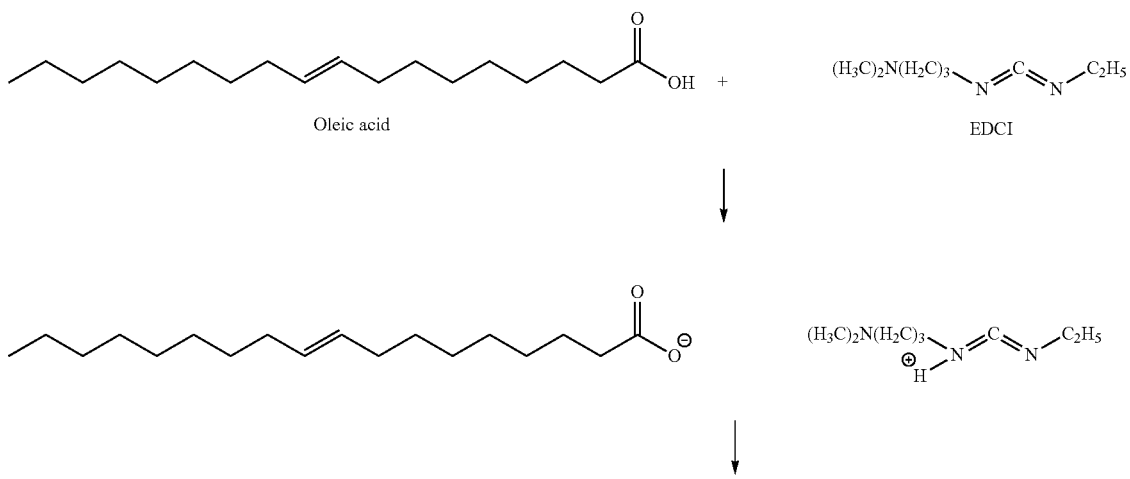

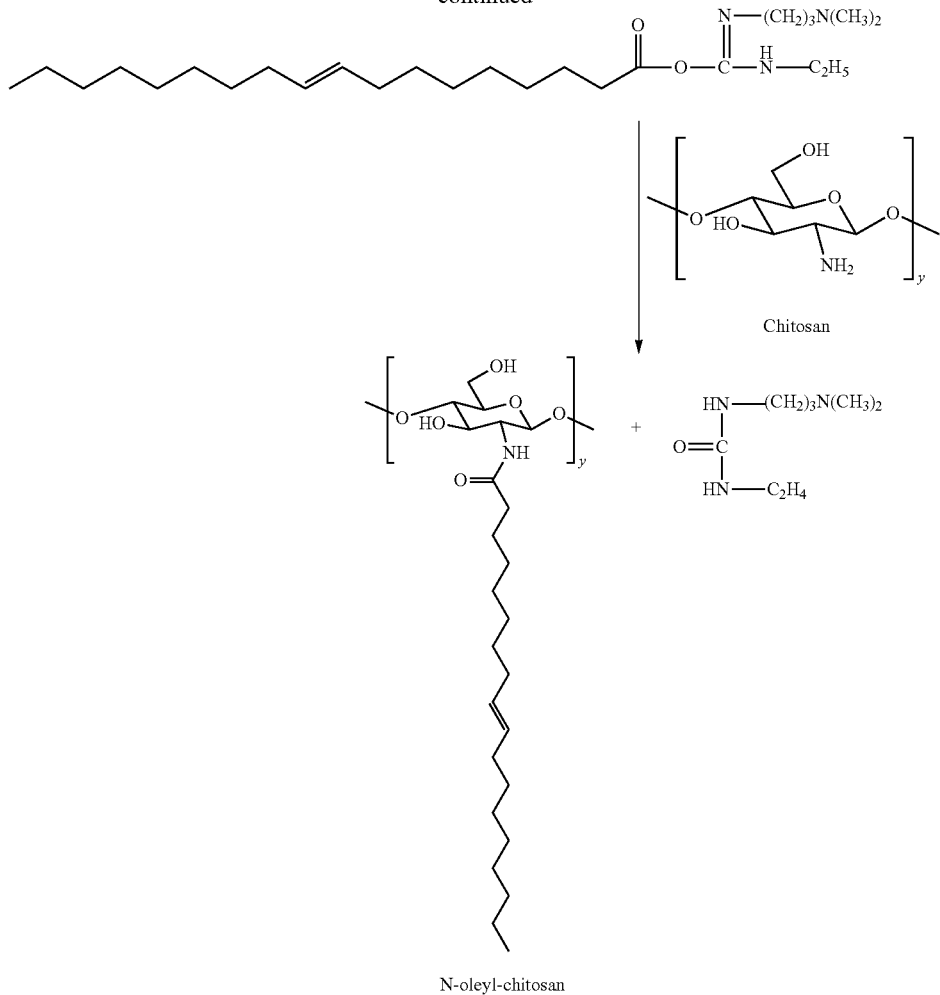

N-oleyl-chitosan

The IR and NMR spectra of the grafted chitosans reveal the secondary amine function obtained after N-acylation and the presence of the grafted alkyl chains.

According to another embodiment of the invention, in the inclusion complex, chitosan bears hydrophobic groups grafted at the level of oxygen atoms originating from the —OH groups and/or the —CH$_2$OH groups fixed to the chitosan ring, and having the formula:

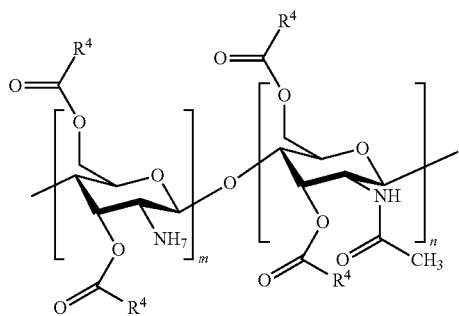

in which n, m and R$^4$ have the meanings designated above.

According to another embodiment of the invention, in the inclusion complex, chitosan bears hydrophobic groups grafted at the level of oxygen atoms originating from the —OH groups and/or the —CH$_2$OH groups fixed to the chitosan ring, and having the formula:

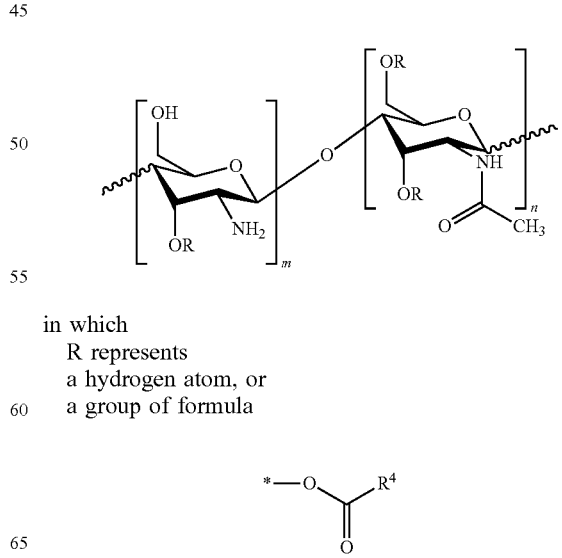

in which
R represents
a hydrogen atom, or
a group of formula in which n, m and R⁴ have the meanings designated above, and provided that R represents at least one group of formula

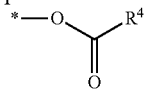

In "*Biomacromolecules* 2002, 3, 1126-1128", Sashiwa et al. describe the "one-pot" reaction of O-acylation of chitosan. Methyl sulphonate, MeSO₃H, makes it possible to protect the —NH₂ from the N-acylation to give predominantly compounds grafted at the level of the oxygen atoms of the chitosan, and more particularly at the level of the primary —OH function of the chitosan (—CH₂OH).

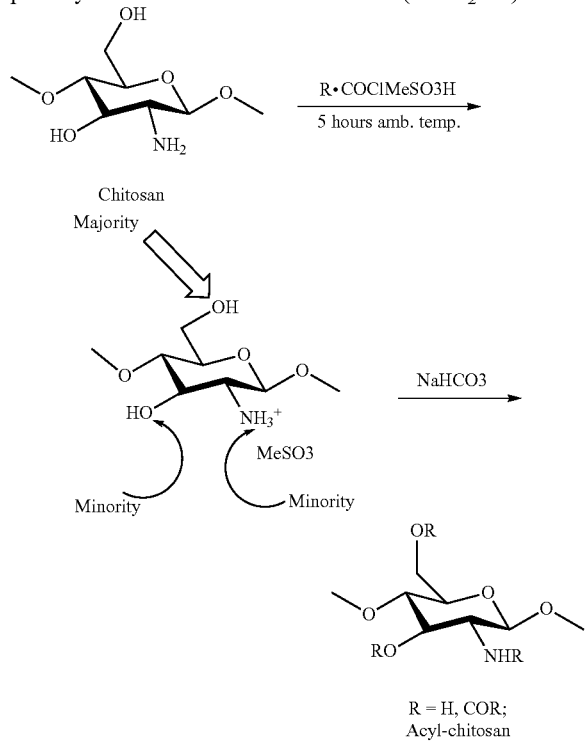

The infrared (IR) spectra of the products obtained show a characteristic band of an ester bond at 1700 cm⁻¹. Moreover, the proton NMR spectra compared with that of native chitosan confirm the presence of the alkyl chains.

According to another particular embodiment, in the inclusion complex of the invention, chitosan bears hydrophobic groups grafted at the level of certain oxygen atoms and of certain nitrogen atoms, and has the formula:

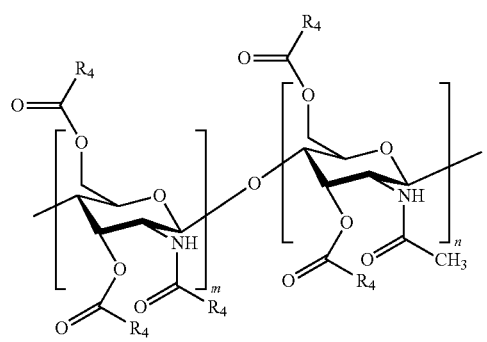

in which n, m and R⁴ have the meanings designated above.

According to another particular embodiment, in the inclusion complex of the invention, chitosan bears hydrophobic groups grafted at the level of certain oxygen atoms and of certain nitrogen atoms, and has the formula:

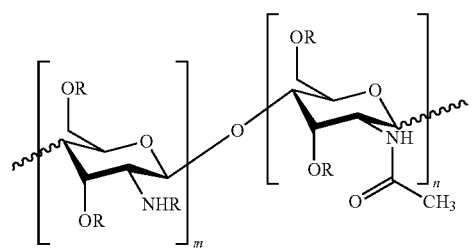

in which
R represents
  a hydrogen atom, or
  a group of formula

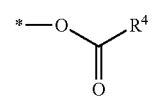

in which n, m and R⁴ have the meanings designated above, and provided that R represents at least one group of formula

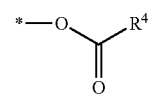

According to yet another embodiment, in the inclusion complex
the polysaccharide is a dextran bearing hydrophobic groups, fixed by oxygen atoms of said dextran and representing groups of formula

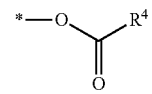

in which
R⁴ has the meanings designated above,
* represents dextran,
the cyclodextrin is α-CD.
Dextran is a polymer of dextrose.
The IR spectrum of O-palmitoyl-dextran shows an absorption band corresponding to the carbonyl of the ester group.
According to another embodiment, in the inclusion complex
the polysaccharide is hyaluronic acid bearing hydrophobic groups, fixed by oxygen atoms of said hyaluronic acid and representing groups of formula

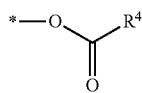

in which
R$^4$ has the meanings designated above,
* represents hyaluronic acid,
the cyclodextrin is α-CD.

According to yet another embodiment, in the inclusion complex of the invention
the polysaccharide is an amylopectin bearing hydrophobic groups fixed by oxygen atoms of said amylopectin and representing groups of formula

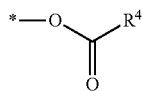

in which
R$^4$ has the meanings designated above,
* represents hyaluronic acid,
the cyclodextrin is α-CD.

Comparison of the IR spectra of O-palmitoyl-amylopectin and native amylopectin confirms the presence of the carbonyl of the ester group in the product obtained.

According to another embodiment, in the inclusion complex of the invention
the polysaccharide is a pullulan bearing hydrophobic groups fixed by oxygen atoms of said pullulan and representing groups of formula

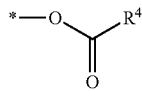

in which
R$^4$ has the meanings designated above,
* represents pullulan,
the cyclodextrin is α-CD.

Pullulan consists of maltotriose units. The three units of glucose that make up maltotriose are joined together by a glycosidic bond of the α-1,4 type, whereas the maltotrioses are joined together by glycosidic bonds of the α-1,6 type. It is grafted, in particular with palmitic acid. Comparison of the IR spectra of O-palmitoyl-pullulan and of native pullulan confirms the presence of the carbonyl of the ester group in the product obtained.

According to another embodiment, in the inclusion complex of the invention
the polysaccharide is a heparin bearing hydrophobic groups fixed by nitrogen atoms of said heparin and representing groups of formula

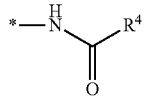

in which
R$^4$ has the meanings designated above,
* represents heparin,
or the polysaccharide is a heparin bearing hydrophobic groups fixed by oxygen atoms of said heparin, these oxygens possibly originating from the hydroxyl or carboxyl groups of the heparin, and representing groups of formula

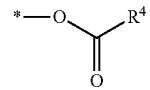

in which
R$^4$ has the meanings designated above,
* represents heparin,
and the cyclodextrin is α-CD.

According to another advantageous aspect, in the inclusion complex of the invention
the polysaccharide is a carrageenan bearing hydrophobic groups fixed by nitrogen atoms of said carrageenan sulphate and representing groups of formula

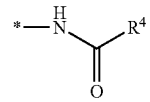

in which
R$^4$ has the meanings designated above,
* represents carrageenan,
or the polysaccharide is a carrageenan bearing hydrophobic groups fixed by oxygen atoms of said carrageenan, these oxygens possibly originating from the hydroxyl or carboxyl groups of carrageenan, and representing groups of formula

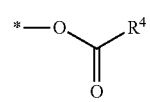

in which
R$^4$ has the meanings designated above,
* represents carrageenan,
and the cyclodextrin is α-CD.

According to another advantageous aspect, in the inclusion complex of the invention
the polysaccharide is a hyaluronic acid bearing hydrophobic groups fixed by nitrogen atoms of said hyaluronic acid and representing groups of formula

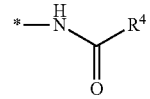

in which
R$^4$ has the meanings designated above,
* represents hyaluronic acid,
or the polysaccharide is a hyaluronic acid bearing hydrophobic groups fixed by oxygen atoms of said hyaluronic acid, these oxygens possibly originating from the hydroxyl or carboxyl groups of the hyaluronic acid, and representing groups of formula

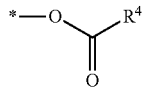

in which
R$^4$ has the meanings designated above,
* represents hyaluronic acid,
and the cyclodextrin is α-CD.

According to another advantageous aspect, in the inclusion complex of the invention
the polysaccharide is a glycosaminoglycan bearing hydrophobic groups fixed by nitrogen atoms of said glycosaminoglycan and representing groups of formula

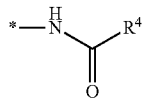

in which
R$^4$ has the meanings designated above,
* represents glycosaminoglycan,
or the polysaccharide is a glycosaminoglycan bearing hydrophobic groups fixed by oxygen atoms of said glycosaminoglycan, these oxygens possibly originating from the hydroxyl or carboxyl groups of glycosaminoglycan, and representing groups of formula

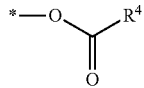

in which
R$^4$ has the meanings designated above,
* represents glycosaminoglycan,
and the cyclodextrin is α-CD.

According to another advantageous aspect, in the inclusion complex of the invention
the polysaccharide is a carrageenan sulphate bearing hydrophobic groups fixed by nitrogen atoms of said carrageenan sulphate and representing groups of formula

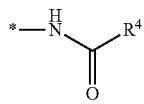

in which
R$^4$ has the meanings designated above,
* represents carrageenan sulphate,
or the polysaccharide is a carrageenan sulphate bearing hydrophobic groups fixed by oxygen atoms of said carrageenan sulphate, these oxygens possibly originating from the hydroxyl or carboxyl groups of carrageenan sulphate, and representing groups of formula

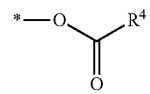

in which
R$^4$ has the meanings designated above,
* represents carrageenan sulphate,
and the cyclodextrin is α-CD.

According to another advantageous aspect, in the inclusion complex of the invention
the polysaccharide is a dextran sulphate bearing hydrophobic groups fixed by nitrogen atoms of said dextran sulphate and representing groups of formula

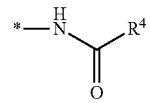

in which
R$^4$ has the meanings designated above,
* represents dextran sulphate,
or the polysaccharide is a dextran sulphate bearing hydrophobic groups fixed by oxygen atoms of said dextran sulphate, these oxygens possibly originating from the hydroxyl or carboxyl groups of dextran sulphate, and representing groups of formula

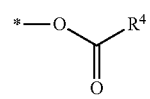

in which
R$^4$ has the meanings designated above,
* represents dextran sulphate,
and the cyclodextrin is α-CD.

According to another advantageous aspect, in the inclusion complex of the invention
the polysaccharide is a cellulose sulphate bearing hydrophobic groups fixed by nitrogen atoms of said cellulose sulphate and representing groups of formula

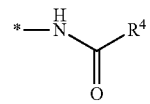

in which
R$^4$ has the meanings designated above,
* represents cellulose sulphate,
or the polysaccharide is a cellulose sulphate bearing hydrophobic groups fixed by oxygen atoms of said cellulose sulphate, these oxygens possibly originating from the hydroxyl or carboxyl groups of cellulose sulphate, and representing groups of formula

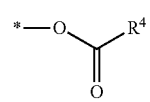

in which
- $R^4$ has the meanings designated above,
- * represents cellulose sulphate,
- and the cyclodextrin is α-CD.

According to another advantageous aspect, in the inclusion complex of the invention
- the polysaccharide is a heparan sulphate bearing hydrophobic groups fixed by nitrogen atoms of said heparan sulphate and representing groups of formula

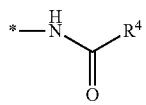

in which
- $R^4$ has the meanings designated above,
- * represents heparan sulphate,
- or the polysaccharide is a heparan sulphate bearing hydrophobic groups fixed by oxygen atoms of said heparan sulphate, these oxygens possibly originating from the hydroxyl or carboxyl groups of the heparan sulphate, and representing groups of formula

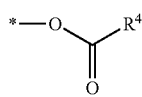

in which
- $R^4$ has the meanings designated above,
- * represents heparan sulphate,
- and the cyclodextrin is α-CD.

According to another advantageous aspect, in the inclusion complex of the invention
- the polysaccharide is a keratan sulphate bearing hydrophobic groups fixed by nitrogen atoms of said keratan sulphate and representing groups of formula

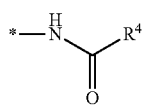

in which
- $R^4$ has the meanings designated above,
- * represents keratan sulphate,
- or the polysaccharide is a keratan sulphate bearing hydrophobic groups fixed by oxygen atoms of said keratan sulphate, these oxygens possibly originating from the hydroxyl or carboxyl groups of keratan sulphate, and representing groups of formula

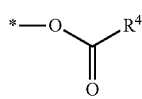

in which
- $R^4$ has the meanings designated above,
- * represents keratan sulphate,
- and the cyclodextrin is α-CD.

According to another advantageous aspect, in the inclusion complex of the invention
- the polysaccharide is a chondroitin sulphate bearing hydrophobic groups fixed by nitrogen atoms of said chondroitin sulphate and representing groups of formula

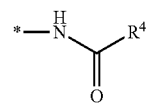

in which
- $R^4$ has the meanings designated above,
- * represents chondroitin sulphate,
- or the polysaccharide is a chondroitin sulphate bearing hydrophobic groups fixed by oxygen atoms of said chondroitin sulphate, these oxygens possibly originating from the hydroxyl or carboxyl groups of chondroitin sulphate, and representing groups of formula

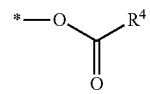

in which
- $R^4$ has the meanings designated above,
- * represents chondroitin sulphate,
- and the cyclodextrin is α-CD.

According to another advantageous aspect, in the inclusion complex of the invention
- the polysaccharide is a dextrin sulphate bearing hydrophobic groups fixed by nitrogen atoms of said dextrin sulphate and representing groups of formula

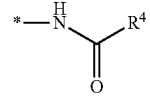

in which
- $R^4$ has the meanings designated above,
- * represents dextrin sulphate,
- or the polysaccharide is a dextrin sulphate bearing hydrophobic groups fixed by oxygen atoms of said dextrin sulphate, these oxygens possibly originating from the hydroxyl or carboxyl groups of dextrin sulphate, and representing groups of formula

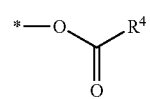

in which

R⁴ has the meanings designated above,

* represents dextrin sulphate, and the cyclodextrin is α-CD.

According to an advantageous embodiment, the invention also relates to a particle with a size in the range from 10 nm to 100,000 nm containing inclusion complexes formed by interaction between at least a polysaccharide comprising hydrophobic groups bound covalently to said polysaccharide, optionally functionalized with a ligand selected from antibodies, antibody fragments, receptors, lectins or biotin or derivatives thereof, a cyclodextrin in the form of monomer, optionally functionalized with a ligand selected from antibodies, antibody fragments, receptors, lectins or biotin or derivatives thereof.

The invention also relates to a particle of a size in the range from 50 nm to 10,000 nm containing inclusion complexes between:

a polysaccharide comprising hydrophobic groups bound covalently to said polysaccharide, optionally functionalized with a ligand selected from antibodies, antibody fragments, receptors, lectins or biotin or derivatives thereof, and a cyclodextrin in the form of monomer, optionally functionalized with a ligand selected from antibodies, antibody fragments, receptors, lectins or biotin or derivatives thereof.

According to an advantageous embodiment, the invention relates to nanometric particles, of a size in the range from 10 nm to 1000 nm and micrometric particles of a size in the range from 1000 nm to 100,000 nm.

The invention relates to nanometric particles, of a size in the range from 50 nm to 1000 nm and micrometric particles of a size in the range from 1000 nm to 10,000 nm.

According to an advantageous aspect, the invention relates to a particle of a size in the range from 10 nm to 100,000 nm containing inclusion complexes according to the invention formed by interaction between at least:

one polysaccharide selected from chitosan, dextran, hyaluronic acid, amylose, amylopectin, pullulan, heparin, chitin, cellulose derivatives, heparan sulphate, dermatan sulphate, keratan sulphate, chondroitin sulphate, cellulose sulphate, dextran sulphate, dextrin sulphate, starch, pectin, the alginates, the carrageenans, fucan, curdlan, xylan, polyguluronic acid, xanthan, arabinan, polymannuronic acid, and derivatives thereof, comprising hydrophobic groups selected from linear or branched alkyl groups or linear or branched alkenyl groups bearing from 1 to 4 C=C double bonds, conjugated or not, said hydrophobic groups being bound covalently to said polysaccharide, optionally functionalized with a ligand selected from antibodies, antibody fragments, receptors, lectins or biotin or derivatives thereof, and one α-cyclodextrin in the form of monomer, optionally functionalized with a ligand selected from antibodies, antibody fragments, receptors, lectins or biotin or derivatives thereof.

The particle sizes formed were evaluated by quasi-elastic light scattering (QELS) on the one hand and by transmission electron microscopy (TEM) on the other hand.

Size plays a very important role in connection with the quantity of active ingredient encapsulated, the applications envisaged, and the route of administration of the active ingredient.

The invention also relates to a particle of a size in the range from 10 nm to 100,000 nm containing inclusion complexes formed by interaction between at least:

one polysaccharide selected from chitosan, dextran, hyaluronic acid, amylose, amylopectin, pullulan, heparin, chitin, cellulose derivatives, heparan sulphate, dermatan sulphate, keratan sulphate, chondroitin sulphate, cellulose sulphate, dextran sulphate, dextrin sulphate, starch, pectin, the alginates, the carrageenans, fucan, curdlan, xylan, polyguluronic acid, xanthan, arabinan, polymannuronic acid, and derivatives thereof, comprising hydrophobic groups selected from linear or branched alkyl groups containing from 2 to 1000 carbon atoms, or linear or branched, in particular linear, alkenyl groups, which may contain at least one C=C double bond, said hydrophobic groups being bound covalently to said polysaccharide, optionally functionalized with a ligand selected from antibodies, antibody fragments, receptors, lectins or biotin or derivatives thereof, and one α-cyclodextrin in the form of monomer, optionally functionalized with a ligand selected from antibodies, antibody fragments, receptors, lectins or biotin or derivatives thereof.

According to a particular embodiment, the invention also relates to particles of a size in the range from 10 nm to 100,000 nm containing inclusion complexes formed by interaction between:

a mixture of at least two polysaccharides selected from chitosan, dextran, hyaluronic acid, amylose, amylopectin, pullulan, heparin, chitin, cellulose derivatives, heparan sulphate, dermatan sulphate, keratan sulphate, chondroitin sulphate, cellulose sulphate, dextran sulphate, dextrin sulphate, starch, pectin, the alginates, the carrageenans, fucan, curdlan, xylan, polyguluronic acid, xanthan, arabinan, polymannuronic acid, and derivatives thereof, comprising hydrophobic groups selected from linear or branched alkyl groups containing from 2 to 1000 carbon atoms, or linear or branched, in particular linear, alkenyl groups, which may contain at least one C=C double bond, said hydrophobic groups being bound covalently to said polysaccharide, optionally functionalized with a ligand selected from antibodies, antibody fragments, receptors, lectins or biotin or derivatives thereof, and at least one α-cyclodextrin in the form of monomer, optionally functionalized with a ligand selected from antibodies, antibody fragments, receptors, lectins or biotin or derivatives thereof.

The invention also relates to an encapsulation system containing one or more particles defined above, and a substance used for its properties in the pharmaceutical, paramedical, medical device, animal-feed, agrochemical, medical, cosmetic, veterinary, agri-food, pesticide, cosmetotextile, perfumery, and environmental fields (water purification for example) or in the paint, building and/or car industry.

A medical device is an instrument, apparatus, equipment or software intended to be used for humans or animals for the purposes of: diagnosis, prevention, control, treatment or attenuation of a disease, diagnosis, control, treatment, attenuation or compensation of a wound or of a handicap, investigation or replacement or modification of the anatomy or of a physiological process, or control of conception.

According to an advantageous aspect, the substance has pharmaceutical properties and is selected from inorganic compounds and organic compounds, synthetic or natural.

The encapsulation system defined above according to the invention may be used for preparing suitable compositions in the pharmaceutical, medical, paramedical, medical device, animal-feed, cosmetic, veterinary, agri-food, pesticide, cosmetotextile, perfumery, and environmental fields (water purification for example) or in the paint, packaging, building and/or car industry.

The substance encapsulated may have pharmaceutical properties and may be an active ingredient for therapeutic use. It may belong to the following list, the latter in no case being limiting, to the group of compounds with vitamin properties, in particular vitamin A, vitamin E, vitamin C, the K vitamins, the B vitamins, vitamin D, antitumour compounds, in particular paclitaxel, docetaxel, tamoxifen, doxorubicin, analgesics, in particular paracetamol, anti-inflammatories, in particular diclofenac, ibuprofen, ketoprofen, antibiotics, in particular the penicillins, the tetracyclines, antifungals, in particular ketoconazole, clotrimazole, nystatin, chlorhexidine and derivatives thereof, antiparasitic agents, in particular albendazole, metronidazole, enzymatic compounds, in particular alkaline phosphatase, acetylcholinesterase, alcohol dehydrogenase, hormonal compounds, in particular testosterone, levonorgestrel, anxiolytics, in particular the benzodiazepines, antidiabetic agents, in particular glicazide, anti-hypertensives, in particular nifedipine, or vaccines, antivirals, in particular AZT, analgesics or combinations of analgesics, in particular paracetamol, antiepileptics in particular the barbiturates and derivatives, local and general anaesthetics, in particular atropine, but also hypnotics, sedatives, antipsychotics, neuroleptics, antidepressants, anxiolytics, in particular antagonists, nerve blocking agents, anticholinergics, cholinomimetics, antimuscarinics, muscarinics, in particular anti-adrenergics, antiarrhythmics, antiarthritics, antiasthmatics, anticonvulsives, antihistamines, anti-nausea agents, antineoplastics, antipyretics, antipruritics, antispasmodics, diuretics, vasodilators, central nervous system stimulants, in particular preparations against coughs and colds, decongestants, bone growth stimulants, inhibitors of bone resorption, immunosuppressants, muscle relaxants, psychostimulants, sedatives, tranquillizers, proteins, peptides or fragments thereof, said proteins, peptides or fragments being natural, recombinant or produced chemically, nucleic acids (ribonucleotides or deoxyribonucleotides), in particular single- and double-stranded molecules, gene constructs, expression vectors, antisense molecules and others of the same kind.

This substance for therapeutic use may be used in humans and in animals.

The substance encapsulated may also have cosmetic properties and belong to the group of compounds with anti-inflammatory, anti-ageing, anti-ultraviolet (anti-UV), depigmenting, wound-healing, hydrating, perfuming, deodorizing, antibacterial, antiperspirant, cleaning, colouring, and preserving properties.

In a particular encapsulation system, the substance has nutritional properties and belongs to the group of compounds with vitamin, enzymatic, and sweetening properties. It may also be an essential oil, a colorant, a preservative, an antioxidant, or a probiotic.

Some molecules or families of molecules that may be encapsulated are: molsidomine, ketoconazole, gliclazide, diclofenac, levonorgestrel, paclitaxel, docetaxel, tamoxifen, hydrocortisone, pancratistatin, ketoprofen, diazepam, ibuprofen, nifedipine, testosterone, tamoxifen, furosemide, tolbutamide, chloramphenicol, the benzodiazepines, naproxen, dexamethasone, diflunisal, anadamide, pilocarpine, daunorubicin, doxorubicin, the essential oils, the terpenes, the terpenoids.

To improve the solubility of the molecules of interest, the use of a solvent or a mixture of solvents may be envisaged, in particular: alkyl acetate (ethyl acetate, butyl acetate, methyl acetate), acetone, acetonitrile, acetic acid, methanoic acid, ammonia, acetic anhydride, aniline, anisole, benzene, butanol, butanone, chlorobenzene, chloroform, cyclohexane, cyclopentane, dichloroethane, dichloromethane, diisopropyl ether, dimethylformamide, dimethylsulphoxide, dioxane, water, ethanol, glycol ether, diethyl ether, ethylene glycol, heptane, hexamethylphosphoramide, hexane, methanol, methyl ethyl ketone, nitrobenzene, pentane, perchloroethylene, propanol, propoxypropane, pyridine, carbon disulphide, tetrachloroethane, tetrahydrofuran, toluene, trichloroethane, trichloroethylene, tremethylpentane, xylene. The fields of use of the compositions containing the encapsulation system with the active ingredient are therefore the medical, veterinary, cosmetic, and cosmetotextile fields, the environmental field in particular connected with water purification, the paint, building or car sector, and perfumery.

The invention also relates to the use of the particles defined above.

The invention thus relates to the use of said particles as medicaments, in particular as adjuvants for vaccination, treatment of burns, and/or for wound-healing.

The invention also relates to the use of said particles in the preparation of medicaments having at least one activity for preventing, inhibiting and/or treating fungal, bacterial, viral and/or parasitic infections on biotic or abiotic surfaces.

The invention also relates to the use of said particles as veterinary medicaments, in particular as adjuvants for vaccination.

The invention also relates to the use of the particles as a cosmetic agent, in particular as anti-ageing, depigmenting, wound-healing, hydrating, perfuming, deodorizing, antiperspirant, cleaning, colouring, or preserving agent.

The invention also relates to the use of the particles for carrying out a method for preparing devices, in particular wound-healing dressings, said devices comprising said particles, and being able to release said particles or one or more active substance(s) of interest contained in said particles.

The invention also relates to a pharmaceutical composition containing, as active substance, the substance encapsulated in the particles, in solid form, or in the form of solution or suspension in a physiological medium, optionally enriched with an excipient such as glucose, sucrose or any other pharmaceutically acceptable excipient, usable for the following routes:

parenteral, oral, cutaneous, subcutaneous, nasal, pulmonary or ocular, and for any administration at the level of a mucous membrane, or at the level of a precise site (tumour, lumen of certain blood vessels), in the form of pills (tablets), soft capsules, hard capsules (gelatin capsules), powders, granules, soluble or dispersible tablets, patches, implants, suppositories, solutions, suspension, syrup, pastes, creams, gels, emulsions, sprays, lotions, ointments, shampoos.

The invention also relates to a pharmaceutical composition containing, as active substance, a substance encapsulated in inclusion complexes or in particles defined above, together with a pharmaceutically acceptable vehicle, in solid form, or in the form of solution or suspension in a physiological medium, usable by the following routes:

parenteral, oral, cutaneous, subcutaneous, nasal, pulmonary or ocular, and for any administration at the level of a mucous membrane, in particular in the form of pills (tablets), soft capsules, hard capsules (gelatin capsules), powders, granules, soluble or dispersible tablets, patches, implants, suppositories, solutions, suspension, syrup, pastes, creams, gels, emulsions, sprays, lotions, or ointments.

The forms that are advantageous in the pharmaceutical field are tablets, soft capsules, hard capsules (gelatin capsules), powders, granules, patches, implants, suppositories, solutions, suspensions, syrups, pastes, creams, gels, emulsions, sprays, lotions and ointments.

The forms that are advantageous in the paramedical field are dressings, catheters, compresses, gauze, hydrophilic cotton, normal saline, spray etc.

The forms that are advantageous in the field of medical devices are implants, prostheses, equipment for washing and disinfecting instruments, compresses, dressings (in particular wound-healing dressings), sprays, gauzes, hydrophilic cotton etc.

The forms that are advantageous in the veterinary field are the oral forms (tablets, powders, soft capsules, hard capsules (gelatin capsules), granules, pastes, solutions, suspensions), injectable forms (solutions, suspensions) and topical forms the action of which may be local or systemic (sprays, collars, ear tags, powders, lotions, ointments, shampoos, patches, emulsions, milk, gel, cream).

The forms that are advantageous in the food sector are solutions, emulsions, pastes, gels, powders used alone or incorporated in food preparations; in the field of food supplements: mainly the oral forms (powders, tablets, hard capsules (gelatin capsules), granules, soft capsules, pastes, solutions, suspensions, infusions).

The invention also relates to a cosmetic composition containing, as active substance, the substance encapsulated in the particles, and containing cosmetically acceptable excipients, usable in the form of gels, pastes, ointments, lotions, creams, milks, sticks, shampoos, powders, aerosols, and patches.

The invention also relates to a method for preparing an inclusion complex comprising a step of mixing:
  a polysaccharide comprising hydrophobic groups bound covalently by a nitrogen atom or by one or more oxygen atoms to said polysaccharide,
  and a cyclodextrin (CD) in the form of monomer,
to obtain an inclusion complex in which said polysaccharide and said cyclodextrin are bound non-covalently.

According to a particular embodiment, the method for the preparation, according to the invention, of an inclusion complex comprises a step of mixing:
  a polysaccharide comprising hydrophobic groups bound covalently to the polysaccharide by a nitrogen atom of said polysaccharide,
  and a cyclodextrin (CD) in the form of monomer,
to obtain an inclusion complex in which said polysaccharide and said cyclodextrin are bound non-covalently.

According to a particular embodiment, the method for the preparation, according to the invention, of an inclusion complex comprises a step of mixing at least:
  one polysaccharide comprising hydrophobic groups bound covalently to the polysaccharide by a nitrogen atom of said polysaccharide, and
  one cyclodextrin (CD) in the form of monomer,
to obtain an inclusion complex in which said polysaccharide and said cyclodextrin are bound non-covalently.

The invention also relates to a method for preparing an inclusion complex as defined above, comprising a step of mixing at least one polysaccharide in the form of suspension in a solvent, in particular water comprising hydrophobic groups bound covalently to the polysaccharide by oxygen atoms of said polysaccharide, and
one α-cyclodextrin (CD) in the form of monomer,
to obtain an inclusion complex in which said polysaccharide and said cyclodextrin are bound non-covalently,
and in particular comprising a step of mixing:
  a polysaccharide selected from chitosan, dextran, hyaluronic acid, amylose, amylopectin, pullulan, heparin, chitin, heparan sulphate, dermatan sulphate, keratan sulphate, chondroitin sulphate, cellulose sulphate, dextran sulphate, dextrin sulphate, starch, pectin, the alginates, the carrageenans, fucan, curdlan, xylan, polyguluronic acid, xanthan, arabinan, polymannuronic acid, and derivatives thereof,
said polysaccharide comprising hydrophobic groups of formula:

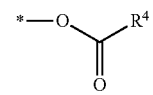

in which
  * represents the polysaccharide,
  $R^4$ represents
    a linear or branched alkyl group containing from 1 to 1000 carbon atoms, in particular the $-(CH_2)_{14}-CH_3$ or $-(CH_2)_{16}-CH_3$ groups,
    a linear or branched alkenyl group containing 2 to 1000 carbon atoms and bearing at least one C=C double bond, in particular the $-(CH_2)_7-CH=CH-CH_2-(CH_2)_7-CH_3$ or $-(CH_2)_7-CH=CH-(CH_2)_7-CH_3$ groups,
and an α-cyclodextrin (CD) having the formula:

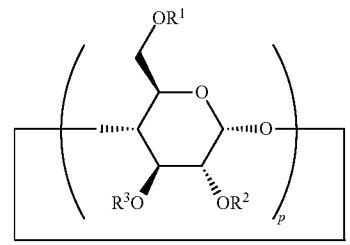

in which
  p is equal to 6,
  $R^1$, $R^2$ and $R^3$, which may be identical or different, in particular identical, are hydrogen atoms, alkyl groups comprising 1 to 3 carbon atoms, selected from methyls, ethyls, propyls, isopropyls, $-NH_2$ amino groups, $-NH_3^+$ ammonium groups, or $-SO_4^{2-}$ sulphate groups and are in particular hydrogen atoms or methyl groups,
said CD being alpha-cyclodextrin (α-CD) in the form of monomer,
to obtain an inclusion complex in which said polysaccharide and said cyclodextrin are bound non-covalently.

In another aspect, the invention also relates to a method for preparing an inclusion complex as defined above, comprising a step of mixing at least:

a polysaccharide comprising hydrophobic groups bound covalently to the polysaccharide by oxygen atoms of said polysaccharide, and an α-cyclodextrin (CD) in the form of monomer in suspension in a solvent, in particular water, to obtain an inclusion complex in which said polysaccharide and said cyclodextrin are bound non-covalently, and in particular comprising a step of mixing:

a polysaccharide selected from chitosan, dextran, hyaluronic acid, amylose, amylopectin, pullulan, heparin, chitin, heparan sulphate, dermatan sulphate, keratan sulphate, chondroitin sulphate, cellulose sulphate, dextran sulphate, dextrin sulphate, starch, pectin, the alginates, the carrageenans, fucan, curdlan, xylan, polyguluronic acid, xanthan, arabinan, polymannuronic acid, and derivatives thereof, said polysaccharide comprising hydrophobic groups of formula:

$$*-O-\underset{O}{\overset{}{C}}-R^4$$

in which
* represents the polysaccharide,
$R^4$ represents
a linear or branched alkyl group containing from 1 to 1000 carbon atoms, in particular the $-(CH_2)_{14}-CH_3$ or $-(CH_2)_{16}-CH_3$ groups,
a linear or branched alkenyl group containing 2 to 1000 carbon atoms and bearing at least one C=C double bond, in particular the $-(CH_2)_7-CH=CH-CH_2-(CH_2)_7-CH_3$ or $-(CH_2)_7-CH=CH-(CH_2)_7-CH_3$ groups, and an α-cyclodextrin (CD) having the formula:

$$\left[\begin{array}{c}OR^1\\ \diagup\\ \cdots O-\\ R^3O\quad OR^2\end{array}\right]_p$$

in which
p is equal to 6,
$R^1$, $R^2$ and $R^3$, which may be identical or different, in particular identical, are hydrogen atoms, alkyl groups comprising 1 to 3 carbon atoms, selected from methyls, ethyls, propyls, isopropyls, $-NH_2$ amino groups, $-NH_3^+$ ammonium groups, or $-SO_4^{2-}$ sulphate groups, and are in particular hydrogen atoms or methyl groups,
said CD being alpha-cyclodextrin (α-CD) in the form of monomer,
to obtain an inclusion complex in which said polysaccharide and said cyclodextrin are bound non-covalently.

In yet another particular embodiment, the invention also relates to a method for preparing an inclusion complex as defined above, comprising a step of mixing at least:

one polysaccharide in the form of suspension in a solvent, in particular water comprising hydrophobic groups bound covalently to the polysaccharide by oxygen atoms of said polysaccharide, and one α-cyclodextrin (CD) in the form of monomer, preferably in suspension in a solvent, in particular water, to obtain an inclusion complex in which said polysaccharide and said cyclodextrin are bound non-covalently, and in particular comprising a step of mixing:

a polysaccharide selected from chitosan, dextran, hyaluronic acid, amylose, amylopectin, pullulan, heparin, chitin, heparan sulphate, dermatan sulphate, keratan sulphate, chondroitin sulphate, cellulose sulphate, dextran sulphate, dextrin sulphate, starch, pectin, the alginates, the carrageenans, fucan, curdlan, xylan, polyguluronic acid, xanthan, arabinan, polymannuronic acid, and derivatives thereof, said polysaccharide comprising hydrophobic groups of formula:

$$*-O-\underset{O}{\overset{}{C}}-R^4$$

in which
* represents the polysaccharide,
$R^4$ represents
a linear or branched alkyl group containing from 1 to 1000 carbon atoms, in particular the $-(CH_2)_{14}-CH_3$ or $-(CH_2)_{16}-CH_3$ groups,
a linear or branched alkenyl group containing 2 to 1000 carbon atoms and bearing at least one C=C double bond, in particular the $-(CH_2)_7-CH=CH-CH_2-(CH_2)_7-CH_3$ or $-(CH_2)_7-CH=CH-(CH_2)_7-CH_3$ groups, and an α-cyclodextrin (CD) having the formula:

$$\left[\begin{array}{c}OR^1\\ \diagup\\ \cdots O-\\ R^3O\quad OR^2\end{array}\right]_p$$

in which
p is equal to 6,
$R^1$, $R^2$ and $R^3$, which may be identical or different, in particular identical, are hydrogen atoms, alkyl groups comprising 1 to 3 carbon atoms, selected from methyls, ethyls, propyls, isopropyls, $-NH_2$ amino groups, $-NH_3^+$ ammonium groups, or $-SO_4^{2-}$ sulphate groups, and are in particular hydrogen atoms or methyl groups,
said CD being alpha-cyclodextrin (α-CD) in the form of monomer,
to obtain an inclusion complex in which said polysaccharide and said cyclodextrin are bound non-covalently.

According to another embodiment, the method for preparing an inclusion complex comprises a step of mixing a polysaccharide comprising hydrophobic groups bound covalently to the polysaccharide by oxygen atoms of said polysaccharide, and a cyclodextrin (CD) in the form of monomer, to obtain an inclusion complex in which said polysaccharide and said cyclodextrin are bound non-covalently.

According to another advantageous embodiment, the method for preparing an inclusion complex comprises a step of mixing at least:

one polysaccharide comprising hydrophobic groups bound covalently to the polysaccharide by oxygen atoms of said polysaccharide, and one cyclodextrin (CD) in the form of monomer, to obtain an inclusion complex in which said polysaccharide and said cyclodextrin are bound non-covalently.

The invention also relates to a method for preparing an inclusion complex comprising a step of mixing:

a chitosan comprising hydrophobic groups fixed covalently to the chitosan by one or more oxygen atoms of said chitosan, and an α-cyclodextrin (CD), and in particular comprising a step of mixing between a chitosan of formula I:

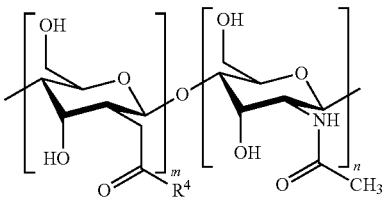

I or a chitosan of formula II:

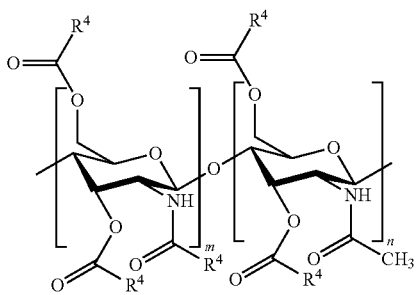

II in which m represents the number of D-glucosamine units, n represents the number of N-acetyl-D-glucosamine units, provided that the degree of deacetylation representing the percentage of m relative to the total number of units is greater than 50%, $R^4$ represents a hydrophobic group and is selected from:

a linear or branched alkyl group containing from 1 to 1000 carbon atoms, in particular the $-(CH_2)_{14}-CH_3$ or $-(CH_2)_{16}-CH_3$ groups, a linear or branched alkenyl group containing 2 to 1000 carbon atoms and bearing from 1 to 4 C=C double bonds, conjugated or not, in particular the $-(CH_2)_7-CH=CH-CH_2-(CH_2)_7-CH_3$ or $-(CH_2)_7-CH=CH-(CH_2)_7-CH_3$ groups, and an α-cyclodextrin (CD) of formula:

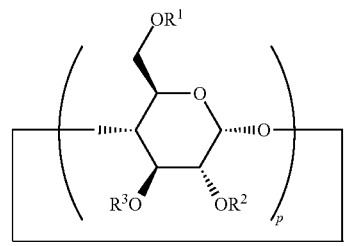

in which p is equal to 6, $R^1$, $R^2$ and $R^3$, which may be identical or different, in particular identical, are hydrogen atoms, alkyl groups comprising 1 to 3 carbon atoms, selected from methyls, ethyls, propyls, isopropyls, $-NH_2$ amino groups, $-NH_3^+$ ammonium groups, or $-SO_4^-$ sulphate groups, and are in particular hydrogen atoms or methyl groups, said CD being alpha-cyclodextrin (α-CD) in the form of monomer, at a concentration in the range from 0.01 to 9000 g/L of aqueous medium, in particular in the range from 1 to 300 g/L of aqueous medium, and in particular equal to approximately 200 g/L of aqueous medium, to obtain an inclusion complex in which the chitosan of formula I and the cyclodextrin are bound non-covalently.

According to a particular embodiment, the method for preparing an inclusion complex comprises a step of mixing:

several polysaccharides comprising hydrophobic groups fixed covalently to the aforesaid polysaccharides by a nitrogen atom and/or by one or more oxygen atoms of said polysaccharides, the polysaccharides being chitosan, dextran, hyaluronic acid, amylose, amylopectin, pullulan, heparin, chitin, cellulose derivatives, heparan sulphate, dermatan sulphate, keratan sulphate, chondroitin sulphate, cellulose sulphate, dextran sulphate, dextrin sulphate, starch, pectin, the alginates, the carrageenans, fucan, curdlan, xylan, polyguluronic acid, xanthan, arabinan, polymannuronic acid, and derivatives thereof, a cyclodextrin (CD), to obtain an inclusion complex in which the polysaccharides and the cyclodextrin are bound non-covalently. The use of several polysaccharides may offer the advantage of modulating the properties of the particles by altering the ratio of the polysaccharides. Thus, it is expected that the size, the overall charge and the intended applications of these particles may be modulated.

According to a particular embodiment, the method for preparing an inclusion complex comprises a step of mixing:

a polysaccharide selected from chitosan, dextran, hyaluronic acid, amylose, amylopectin, pullulan, heparin, chitin, cellulose derivatives, heparan sulphate, dermatan sulphate, keratan sulphate, chondroitin sulphate, cellulose sulphate, dextran sulphate, dextrin sulphate, starch, pectin, the alginates, the carrageenans, fucan, curdlan, xylan, polyguluronic acid, xanthan, arabinan, polymannuronic acid, and derivatives thereof, and is in particular chitosan, said polysaccharide comprising hydrophobic groups of formula:

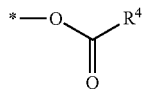

in which
* represents the polysaccharide,
R$^4$ represents:
  a linear or branched alkyl group containing from 1 to 20 carbon atoms, in particular the —(CH$_2$)$_{14}$—CH$_3$ or —(CH$_2$)$_{16}$—CH$_3$ groups,
  a linear or branched alkenyl group containing 2 to 20 carbon atoms and bearing from 1 to 4 C=C double bonds, conjugated or not, in particular the —(CH$_2$)$_7$—CH=CH—CH$_2$—(CH$_2$)$_7$—CH$_3$ or —(CH$_2$)$_7$—CH=CH—(CH$_2$)$_7$—CH$_3$ groups, and
a cyclodextrin (CD) having the formula:

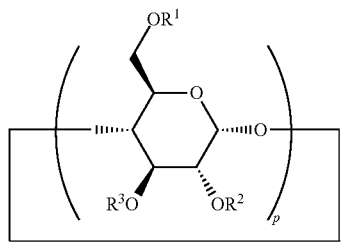

in which
p is an integer equal to 6,
R$^1$, R$^2$ and R$^3$, which may be identical or different, in particular identical, are hydrogen atoms, alkyl groups comprising 1 to 3 carbon atoms, selected from methyls, ethyls, propyls, isopropyls, —NH$_2$ amino groups, —NH$_3^-$ ammonium groups, or —SO$_4^{2-}$ sulphate groups, and are in particular hydrogen atoms or methyl groups,
said CD being alpha-cyclodextrin (α-CD) in the form of monomer,
to obtain an inclusion complex in which said polysaccharide and said cyclodextrin are bound non-covalently.

According to a particular embodiment, the method for preparing an inclusion complex comprises a step of mixing at least
  one polysaccharide selected from chitosan, dextran, hyaluronic acid, amylose, amylopectin, pullulan, heparin, chitin, cellulose derivatives, heparan sulphate, dermatan sulphate, keratan sulphate, chondroitin sulphate, cellulose sulphate, dextran sulphate, dextrin sulphate, starch, pectin, the alginates, the carrageenans, fucan, curdlan, xylan, polyguluronic acid, xanthan, arabinan, polymannuronic acid, and derivatives thereof, and is in particular chitosan,
said polysaccharide comprising hydrophobic groups of formula:

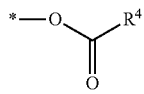

in which
* represents the polysaccharide,
R$^4$ represents:
  a linear or branched alkyl group containing from 1 to 20 carbon atoms, in particular the —(CH$_2$)$_{14}$—CH$_3$ or —(CH$_2$)$_{16}$—CH$_3$ groups,
  a linear or branched alkenyl group containing 2 to 20 carbon atoms and bearing from 1 to 4 C=C double bonds, conjugated or not, in particular the —(CH$_2$)$_7$—CH=CH—CH$_2$—(CH$_2$)$_7$—CH$_3$ or —(CH$_2$)$_7$—CH=CH—(CH$_2$)$_7$—CH$_3$ groups,
and a cyclodextrin (CD) having the formula:

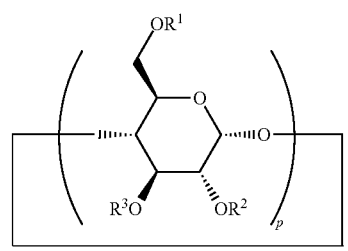

in which
p is an integer equal to 6,
R$^1$, R$^2$ and R$^3$, which may be identical or different, in particular identical, are hydrogen atoms, alkyl groups comprising 1 to 3 carbon atoms, selected from methyls, ethyls, propyls, isopropyls, —NH$_2$ amino groups, —NH$_3^+$ ammonium groups, or —SO$_4^{2-}$ sulphate groups, and are in particular hydrogen atoms or methyl groups,
said CD being alpha-cyclodextrin (α-CD) in the form of monomer,
to obtain an inclusion complex in which said polysaccharide and said cyclodextrin are bound non-covalently.

According to a particular aspect, the method for preparing an inclusion complex comprises a step of mixing the polysaccharide:
  in aqueous solution at a concentration in the range from 0.01 to 9000 g/L, in particular in the range from 1 to 600 g/L, and in particular equal to approximately 10 g/L, the aqueous solvent being selected from pure water, an aqueous solution with pH in the range from 1 to 7 or from 7 to 14, in particular in the range from 5 to 7, or a physiological serum solution optionally enriched with glucose or containing any other excipient for pharmaceutical, medical, paramedical, medical-device, animal-feed, cosmetic, veterinary, agri-food, pesticide, cosmetotextile, perfumery, and environmental use (water purification for example) or in the paint, packaging, building and/or car industry,
  or in dispersion in an aqueous medium selected from pure water, an aqueous solution with pH in the range from 1 to 7 or from 7 to 14, in particular in the range from 5 to 7, or a physiological serum solution optionally enriched with glucose or containing any other excipient for pharmaceutical, medical, paramedical, medical-device, animal-feed, cosmetic, veterinary, agri-food, pesticide, cosmetotextile, perfumery, and environmental use (water purification for example) or in the paint, packaging, building and/or car industry, with a cyclodextrin, α-CD.

The method for preparing an inclusion complex comprises a step of mixing the polysaccharide in aqueous solution at a concentration in the range from 1 to 150 g/L, in particular in the range from 5 to 50 g/L, and in particular equal to approximately 10 g/L, the aqueous solvent being selected from pure water, an aqueous solution with pH in the range from 1 to 7 or from 7 to 12, in particular in the range from 5 to 7, or a physiological serum solution optionally enriched with glucose or containing any other excipient for pharmaceutical, cosmetic, agri-food or veterinary use, or in dispersion in an aqueous medium selected from pure water, an aqueous solution with pH in the range from 1 to 7 or from 7 to 12, in particular in the range from 5 to 7, or a physiological serum solution optionally enriched with glucose or containing any other excipient for pharmaceutical, cosmetic, agri-food or veterinary use, with a cyclodextrin, α-CD.

In the method for preparing an inclusion complex, the step of mixing the polysaccharide in aqueous solution or dispersion is carried out at a concentration in the range from 0.01 to 9000 g/L, in particular in the range from 1 to 600 g/L, and in particular equal to approximately 10 g/L, with a cyclodextrin, in particular α-CD, at a concentration in the range from 0.01 to 9000 g/L, in particular in the range from 1 to 300 g/L, and in particular equal to approximately 200 g/L.

In the method for preparing an inclusion complex, the step of mixing the polysaccharide in aqueous solution or dispersion is carried out at a concentration in the range from 1 to 150 g/L, in particular in the range from 5 to 50 g/L, and in particular equal to approximately 10 g/L, with a cyclodextrin, α-CD, at a concentration in the range from 1 to 150 g/L, in particular in the range from 5 to 50 g/L, and in particular equal to approximately 10 g/L.

According to another embodiment, the method for preparing an inclusion complex comprises a step of mixing the polysaccharide in dispersion in an aqueous medium, the concentration of said polysaccharide being in the range from 0.01 to 9000 g/L of aqueous medium, in particular being in the range from 1 to 600 g/L of aqueous medium, and in particular being equal to approximately 1 g/L or equal to approximately 10 g/L of aqueous medium, with a cyclodextrin, α-CD, at a concentration in the range from 0.01 to 9000 g/L of aqueous medium, in particular in the range from 0.01 to 300 g/L of aqueous medium, and in particular equal to approximately 10 g/L of aqueous medium.

According to another embodiment, the method for preparing an inclusion complex comprises a step of mixing the polysaccharide in dispersion in an aqueous medium, the weight of said polysaccharide being in the range from 1 to 150 g/L of aqueous medium, in particular being in the range from 1 to 10 g/L of aqueous medium, and in particular being equal to approximately 1 g/L or equal to approximately 10 g/L of aqueous medium, with a cyclodextrin, α-CD, at a concentration in the range from 1 to 150 g/L of aqueous medium, in particular in the range from 1 to 50 g/L of aqueous medium, and in particular equal to approximately 10 g/L of aqueous medium.

The complexes also form when the polysaccharide is used in the form of a suspension.

The method for preparing an inclusion complex comprises a step of mixing the polysaccharide with a cyclodextrin, α-CD, the percentage by weight of said polysaccharide being in the range from 0.01% to 90%, and in particular from 0.5% to 50%, the percentage by weight of the cyclodextrin being in the range from 0.01% to 90%, and in particular from 0.5% to 50%, the percentage by weight of water or of aqueous medium being in the range from 10% to 99.99%, and in particular from 50% to 99.5%.

The method for preparing an inclusion complex comprises a step of mixing the polysaccharide with a cyclodextrin, α-CD, the percentage by weight of said polysaccharide being in the range from 0.1% to 15%, and in particular from 0.5% to 5%, the percentage by weight of the cyclodextrin being in the range from 0.1% to 15%, and in particular from 0.5% to 5%, the percentage by weight of water or of aqueous medium being in the range from 70% to 99.9%, and in particular from 90% to 99%.

According to a particular embodiment of the method for preparing an inclusion complex, the step of mixing the polysaccharide with a cyclodextrin, α-CD, is carried out with stirring, in particular magnetic, at a stirring speed in the range from 10 to 1000 rpm, in particular at a stirring speed in the range from 100 to 500 rpm, and in particular at a stirring speed equal to approximately 200 rpm, at a temperature in the range from 1 to 100° C., in particular at a temperature in the range from 10 to 35° C., and in particular at a temperature equal to approximately 20° C., the duration of stirring being in the range from 6 hours to 15 days, in particular from 24 hours to 96 hours, and in particular equal to approximately 72 hours.

According to a particular embodiment of the method for preparing an inclusion complex, the step of mixing the polysaccharide with a cyclodextrin, α-CD, is carried out with stirring, in particular magnetic, at a stirring speed in the range from 50 to 1000 rpm, in particular at a stirring speed in the range from 100 to 500 rpm, and in particular at a stirring speed equal to approximately 200 rpm, at a temperature in the range from 4 to 60° C., in particular at a temperature in the range from 10 to 35° C., and in particular at a temperature equal to approximately 20° C., the duration of stirring being in the range from 24 hours to 15 days, in particular in the range from 24 hours to 48 hours, and in particular equal to approximately 36 hours.

The method for preparing an inclusion complex also comprises a step of preparing a polysaccharide bearing hydrophobic groups, by a reaction of N-acylation a between the polysaccharide and an acid chloride of formula $R^4$—C(O)Cl, in which $R^4$ represents:

a linear or branched alkyl group containing from 1 to 1000 carbon atoms, in particular the —$(CH_2)_{14}$—$CH_3$ or —$(CH_2)_{16}$—$CH_3$ groups, a linear or branched alkenyl group containing 2 to 1000 carbon atoms and bearing at least one C=C double bond, in particular the —$(CH_2)_7$—CH=CH—$CH_2$—$(CH_2)_7$—$CH_3$ or —$(CH_2)_7$—CH=CH—$(CH_2)_7$—$CH_3$ groups, or between the polysaccharide and a fatty acid of formula $R^4$—$CO_2H$, in which $R^4$ has the meanings designated above, in the presence of a coupling agent such as the N-(3-dimethylaminopropyl)-N-ethylcarbodiimide chloride (EDCI) at ambient temperature for 24 hours, or between the polysaccharide and a cyclic acid anhydride of formula $R^4$—CO—O—CO—$R^4$, in which $R^4$ has the meanings designated above, to give a polysaccharide bearing hydrophobic groups fixed covalently to the polysaccharide by a nitrogen atom of said polysaccharide.

The method for preparing an inclusion complex also comprises a step of preparing a polysaccharide bearing hydrophobic groups, by a reaction of N-acylation between the polysaccharide and an acid chloride of formula $R^4$—C(O)Cl, in which $R^4$ represents:

a linear or branched alkyl group containing from 1 to 20 carbon atoms, in particular the —(CH$_2$)$_{14}$—CH$_3$ or —(CH$_2$)$_{16}$—CH$_3$ groups, a linear or branched alkenyl group containing 2 to 20 carbon atoms and bearing from 1 to 4 C=C double bonds, conjugated or not, in particular the —(CH$_2$)$_7$—CH=CH—CH$_2$—(CH$_2$)$_7$—CH$_3$ or —(CH$_2$)$_7$—CH=CH—(CH$_2$)$_7$—CH$_3$ groups, or between the polysaccharide and a fatty acid of formula $R^4$—CO$_2$H, in which $R^4$ has the meanings designated above, in the presence of a coupling agent such as N-(3-dimethylaminopropyl)-N-ethylcarbodiimide chloride (EDCI) at ambient temperature for 24 hours, or between the polysaccharide and a cyclic acid anhydride of formula $R^4$—CO—O—CO—$R^4$, in which $R^4$ has the meanings designated above, to give a polysaccharide bearing hydrophobic groups fixed covalently to the polysaccharide by a nitrogen atom of said polysaccharide.

The reaction of N-acylation relates in particular to chitosan. It is carried out by the action of an acid chloride (Li, Y-Y. et al., 2006, *J. Appl. Polym. Sci.* 102, 1968-1973), of a carboxylic acid, less reactive than the acid chloride, in the presence of the coupling agent EDCI, or by the action of acid anhydrides (Lee, K. Y. et al., 1995, *Biomaterials* 16, 1211-1216; Lee, M. Y. et al., 2005, *Int. J. Biol. Macromol.*, 36, 152-158; Mourya, V. K. and Inamdar, N. N. (2008). *React. Funct. Polym.* 68 (6), 1013-1051).

Another embodiment of the method for preparing an inclusion complex comprises a step of preparing a polysaccharide bearing hydrophobic groups, by a reaction of O-acylation between said polysaccharide dissolved in methanesulphonate and 1 to 20 equivalents per unit of polysaccharide, of fatty acid chloride, the reaction being carried out at ambient temperature, said polysaccharide and acid chloride being as designated above, to give a polysaccharide bearing hydrophobic groups fixed covalently to the polysaccharide by one or more oxygen atoms of said polysaccharide.

Another embodiment of the method for preparing an inclusion complex comprises a step of mixing at least:

one chitosan comprising hydrophobic groups fixed covalently to the chitosan by a nitrogen atom and/or by one or more oxygen atoms of said chitosan, and one cyclodextrin (CD), to obtain an inclusion complex in which the chitosan and the cyclodextrin are bound non-covalently.

Another embodiment of the method for preparing an inclusion complex comprises a step of mixing at least:

one chitosan comprising hydrophobic groups fixed covalently to the chitosan by a nitrogen atom and/or by one or more oxygen atoms of said chitosan, and one cyclodextrin (CD), to obtain an inclusion complex in which the chitosan and the cyclodextrin are bound non-covalently.

According to a particular embodiment, the method for preparing an inclusion complex comprises a step of mixing between

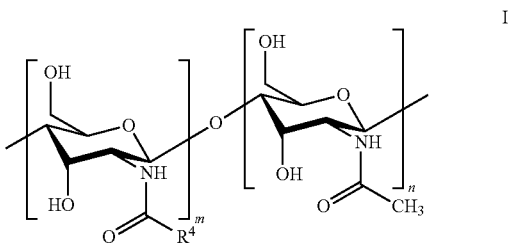

a chitosan of formula:

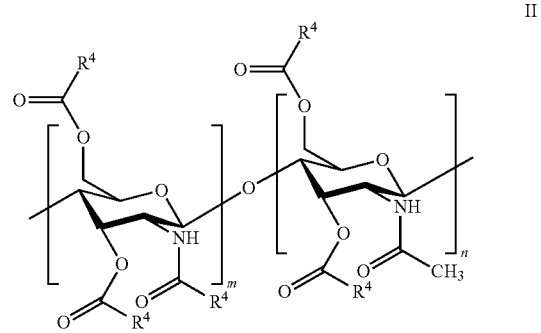

in which m represents the number of deacetylated units, n represents the number of acetylated units, provided that the degree of deacetylation representing the percentage of m relative to the total number of units is greater than 50%, $R^4$ represents a hydrophobic group and is selected from:

a linear or branched alkyl group containing from 1 to 20 carbon atoms, in particular the —(CH$_2$)$_{14}$—CH$_3$ or —(CH$_2$)$_{16}$—CH$_3$ groups, a linear or branched alkenyl group containing 2 to 20 carbon atoms and bearing from 1 to 4 C=C double bonds, conjugated or not, in particular the —(CH$_2$)$_7$—CH=CH—CH$_2$—(CH$_2$)$_7$—CH$_3$ or —(CH$_2$)$_7$—CH=CH—(CH$_2$)$_7$—CH$_3$ groups, and a cyclodextrin (CD) of formula:

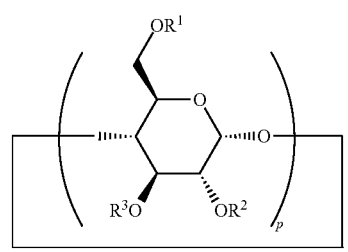

in which p is an integer equal to 6,

R$^1$, R$^2$ and R$^3$, which may be identical or different, in particular identical, are hydrogen atoms, alkyl groups comprising 1 to 3 carbon atoms, selected from methyls, ethyls, propyls, isopropyls, —NH$_2$ amino groups, —NH$_3^+$ ammonium groups, or —SO$_4^{2-}$ sulphate groups, and are in particular hydrogen atoms or methyl groups, said CD being alpha-cyclodextrin (α-CD) in the form of monomer, at a concentration in the range from 1 to 150 g/L of aqueous medium, in particular in the range from 1 to 50 g/L of aqueous medium, and in particular equal to approximately 10 g/L of aqueous medium, said chitosans of formula I or II being in aqueous solution at a concentration in the range from 1 to 150 g/L, in particular being in the range from 1 to 10 g/L, and in particular being equal to approximately 1 or equal to approximately 10 g/L, the aqueous solvent being selected from pure water, an aqueous solution with pH in the range from 1 to 7 or from 7 to 12, in particular in the range from 5 to 7, or a physiological serum solution optionally enriched with glucose or containing any other excipient for pharmaceutical, cosmetic, agri-food or veterinary use, or in dispersion in an aqueous medium selected from pure water, an aqueous solution with pH in the range from 1 to 7 or from 7 to 12, in particular in the range from 5 to 7, or a physiological serum solution optionally enriched with glucose or containing any other excipient for pharmaceutical, cosmetic, agri-food or veterinary use, the weight of said polysaccharide being in the range from 1 to 150 g/L of aqueous medium, in particular being in the range from 1 to 10 g/L of aqueous medium, and in particular being equal to 1 g/L or 10 g/L of aqueous medium, the percentage by weight of said polysaccharide being in the range from 0.1% to 15%, and in particular from 0.5% to 5%, the percentage by weight of the cyclodextrin being in the range from 0.1% to 15%, and in particular from 0.5% to 5%, the percentage by weight of water or of aqueous medium being in the range from 70% to 99.9%, and in particular from 90% to 99%, said mixing being carried out with stirring, in particular magnetic, at a stirring speed in the range from 50 to 1000 rpm, in particular at a stirring speed in the range from 100 to 500 rpm, and in particular at a stirring speed equal to approximately 200 rpm, at a temperature in the range from 4 to 60° C., in particular at a temperature in the range from 10 to 35° C., and in particular at a temperature equal to approximately 20° C., the duration of stirring being in the range from 24 hours to 15 days, in particular in the range from 24 hours to 48 hours, and in particular equal to approximately 36 hours, to obtain an inclusion complex in which the chitosan of formula I or II and the cyclodextrin are bound non-covalently.

According to a particular embodiment, the method for preparing an inclusion complex comprises a step of mixing between a chitosan of formula:

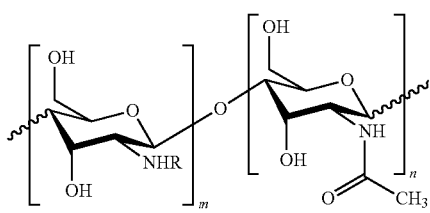

or a chitosan of formula:

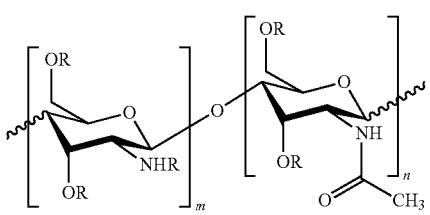

in which

R represents a hydrogen atom, or a group of formula

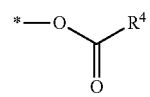

in which

R$^4$ represents a hydrophobic group and is selected from:

a linear or branched alkyl group containing from 1 to 1000 carbon atoms, in particular the —(CH$_2$)$_{14}$—CH$_3$ or —(CH$_2$)$_{16}$—CH$_3$ groups, a linear or branched alkenyl group containing 2 to 1000 carbon atoms and bearing at least one C=C double bond, in particular the —(CH$_2$)$_7$—CH=CH—CH$_2$—(CH$_2$)$_7$—CH$_3$ or —(CH$_2$)$_7$—CH=CH—(CH$_2$)$_7$—CH$_3$ groups, provided that R represents at least one group of formula

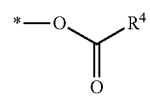

m represents the number of D-glucosamine units, n represents the number of N-acetyl-D-glucosamine units, provided that the percentage of m relative to the total number of units is greater than 50%, and a cyclodextrin (CD) of formula:

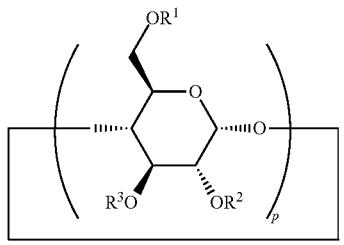

in which p is an integer equal to 6, $R^1$, $R^2$ and $R^3$, which may be identical or different, in particular identical, are hydrogen atoms, alkyl groups comprising 1 to 3 carbon atoms, selected from methyls, ethyls, propyls, isopropyls, —$NH_2$ amino groups, —$NH_3^+$ ammonium groups, or —$SO_4^{2-}$ sulphate groups, and are in particular hydrogen atoms or methyl groups, said CD being alpha-cyclodextrin (α-CD) in the form of monomer, at a concentration in the range from 0.01 to 9000 g/L of aqueous medium, in particular in the range from 1 to 300 g/L of aqueous medium, and in particular equal to approximately 200 g/L of aqueous medium, said chitosans of formula I or II being in aqueous solution at a concentration in the range from 0.01 to 9000 g/L, in particular being in the range from 1 to 300 g/L, and in particular being equal to approximately 200 g/L, the aqueous solvent being selected from pure water, an aqueous solution with pH in the range from 1 to 7 or from 7 to 14, in particular in the range from 5 to 7, or a physiological serum solution optionally enriched with glucose or containing any other excipient for pharmaceutical, medical, paramedical, medical-device, animal-feed, cosmetic, veterinary, agri-food, pesticide, cosmetotextile, perfumery, and environmental use (water purification for example) or in the paint, packaging, building and/or car industry, or in dispersion in an aqueous medium selected from pure water, an aqueous solution with pH in the range from 0 to 7 or from 7 to 14, in particular in the range from 5 to 7, or a physiological serum solution optionally enriched with glucose or containing any other excipient for pharmaceutical, medical, paramedical, medical-device, animal-feed, cosmetic, veterinary, agri-food, pesticide, cosmetotextile, perfumery, and environmental use (water purification for example) or in the paint, packaging, building and/or car industry, the weight of said polysaccharide being in the range from 0.01 to 9000 g/L of aqueous medium, in particular being in the range from 1 to 60 g/L of aqueous medium, and in particular being equal to 1 g/L or 10 g/L of aqueous medium, the percentage by weight of said polysaccharide being in the range from 0.01% to 90%, and in particular from 0.5% to 5%, the percentage by weight of the cyclodextrin being in the range from 0.01% to 90%, and in particular from 0.5% to 5%, the percentage by weight of water or of aqueous medium being in the range from 10% to 99.99%, and in particular from 50% to 99.5%, said mixing being carried out with stirring, in particular magnetic, at a stirring speed in the range from 10 to 1000 rpm, in particular at a stirring speed in the range from 100 to 500 rpm, and in particular at a stirring speed equal to approximately 200 rpm, at a temperature in the range from 1 to 100° C., in particular at a temperature in the range from 10 to 35° C., and in particular at a temperature equal to approximately 20° C., the duration of stirring being in the range from 12 hours to 15 days, in particular in the range from 24 hours to 96 hours, and in particular equal to approximately 72 hours, to obtain an inclusion complex in which the chitosan of formula I or II and the cyclodextrin are bound non-covalently.

In another aspect, the invention also relates to the particles obtained by the methods described above.

The invention also relates to a chitosan bearing hydrophobic groups having as formula II:

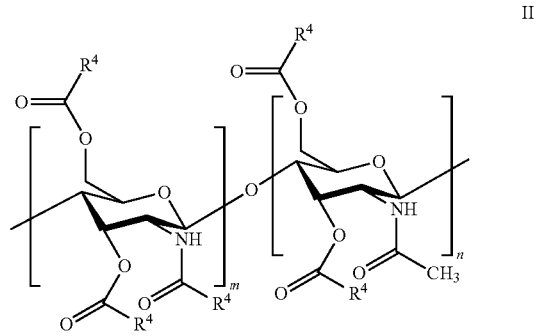

in which $R^4$ represents a linear or branched alkyl group containing from 1 to 20 carbon atoms, in particular the —$(CH_2)_{14}$—$CH_3$ or —$(CH_2)_{16}$—$CH_3$ groups, a linear or branched alkenyl group containing 2 to 20 carbon atoms and bearing from 1 to 4 C=C double bonds, conjugated or not, in particular the —$(CH_2)_7$—CH=CH—$CH_2$—$(CH_2)_7$—$CH_3$ or —$(CH_2)_7$—CH=CH—$(CH_2)_7$—$CH_3$ groups, m represents the number of deacetylated units, n represents the number of acetylated units, provided that the degree of deacetylation representing the percentage of m relative to the total number of units is greater than 50%.

The invention also relates to a chitosan bearing hydrophobic groups having formula II:

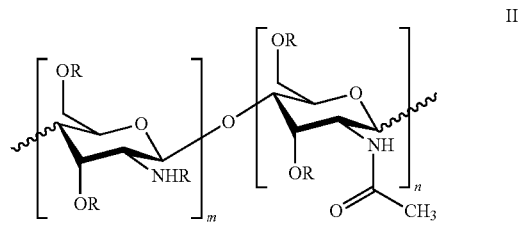

in which
R represents
a hydrogen atom, or
a group of formula

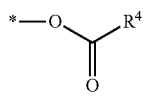

in which
R⁴ represents
a linear or branched alkyl group containing from 1 to 1000 carbon atoms, in particular the —(CH$_2$)$_{14}$—CH$_3$ or —(CH$_2$)$_{16}$—CH$_3$ groups,
a linear or branched alkenyl group containing 2 to 1000 carbon atoms and bearing at least one C=C double bond, in particular the —(CH$_2$)$_7$—CH=CH—CH$_2$—(CH$_2$)$_7$—CH$_3$ or —(CH$_2$)$_7$—CH=CH—(CH$_2$)$_7$—CH$_3$ groups,
provided that R represents at least one group of formula

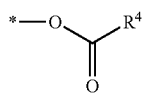

m represents the number of D-glucosamine units,
n represents the number of N-acetyl-D-glucosamine units,
provided that the degree of deacetylation (DDA) representing the percentage of m relative to the total number of units is greater than 50%.

The invention also relates to a carrageenan bearing hydrophobic groups having formula I and/or II:

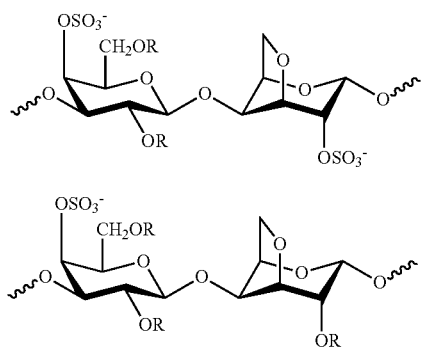

R represents
a hydrogen atom, or
a group of formula

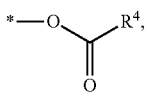

in which
R⁴ represents
a linear or branched alkyl group containing from 1 to 1000 carbon atoms, in particular the —(CH$_2$)$_{14}$—CH$_3$ or —(CH$_2$)$_{16}$—CH$_3$ groups,
a linear or branched alkenyl group containing 2 to 1000 carbon atoms and bearing at least one C=C double bond, in particular the —(CH$_2$)$_7$—CH=CH—CH$_2$—(CH$_2$)$_7$—CH$_3$ or —(CH$_2$)$_7$—CH=CH—(CH$_2$)$_7$—CH$_3$ groups,
provided that R represents at least one group of formula

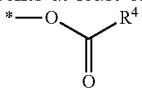

The invention also relates to a heparin bearing hydrophobic groups having the formula:

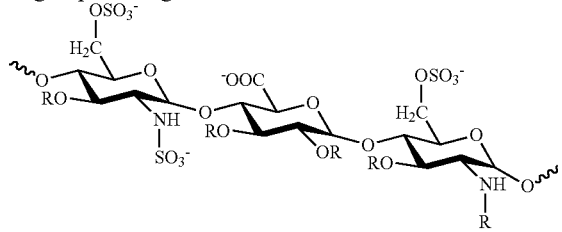

in which
R represents
a hydrogen atom, or
a group of formula

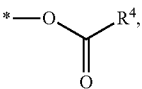

R⁴ represents
a linear or branched alkyl group containing from 1 to 1000 carbon atoms, in particular the —(CH$_2$)$_{14}$—CH$_3$ or —(CH$_2$)$_{16}$—CH$_3$ groups,
a linear or branched alkenyl group containing 2 to 1000 carbon atoms and bearing at least one C=C double bond, in particular the —(CH$_2$)$_7$—CH=CH—CH$_2$—(CH$_2$)$_7$—CH$_3$ or —(CH$_2$)$_7$—CH=CH—(CH$_2$)$_7$—CH$_3$ groups,
provided that R represents at least one group of formula

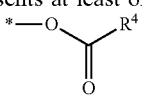

The invention also relates to an amylopectin bearing hydrophobic groups having the formula:

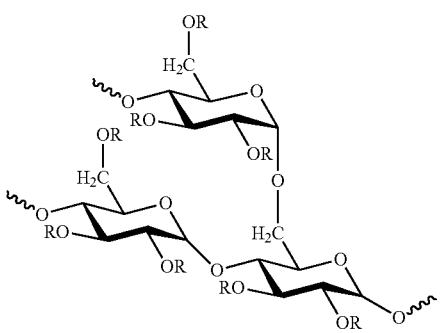

R represents
a hydrogen atom, or
a group of formula

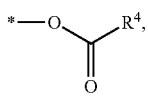

in which
R$^4$ represents
a linear or branched alkyl group containing from 1 to 1000 carbon atoms, in particular the —(CH$_2$)$_{14}$—CH$_3$ or —(CH$_2$)$_{16}$—CH$_3$ groups,
a linear or branched alkenyl group containing 2 to 1000 carbon atoms and bearing at least one C=C double bond, in particular the —(CH$_2$)$_7$—CH=CH—CH$_2$—(CH$_2$)$_7$—CH$_3$ or —(CH$_2$)$_7$—CH=CH—(CH$_2$)$_7$—CH$_3$ groups,
provided that R represents at least one group of formula

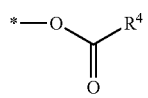

The invention also relates to a pullulan bearing hydrophobic groups having the formula:

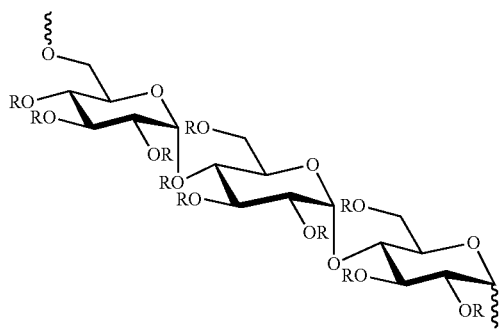

R represents
a hydrogen atom, or
a group of formula

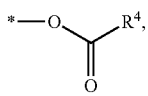

in which
R$^4$ represents
a linear or branched alkyl group containing from 1 to 1000 carbon atoms, in particular the —(CH$_2$)$_{14}$—CH$_3$ or —(CH$_2$)$_{16}$—CH$_3$ groups,
a linear or branched alkenyl group containing 2 to 1000 carbon atoms and bearing at least one C=C double bond, in particular the —(CH$_2$)—CH=CH—CH$_2$—(CH$_2$)$_7$—CH$_3$ or —(CH$_2$)$_7$—CH=CH—(CH$_2$)$_7$—CH$_3$ groups, provided that R represents at least one group of formula

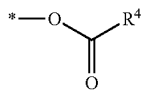

The invention also relates to a dextran bearing hydrophobic groups having the formula:

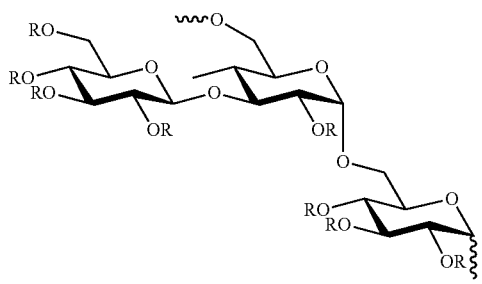

in which
R represents
a hydrogen atom, or
a group of formula

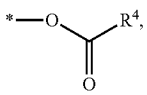

in which
R$^4$ represents
a linear or branched alkyl group containing from 1 to 20 carbon atoms, in particular the —(CH$_2$)$_{14}$—CH$_3$ or —(CH$_2$)$_{16}$—CH$_3$ groups,
a linear or branched alkenyl group containing 2 to 20 carbon atoms and bearing from 1 to 4 C=C double bonds, conjugated or not, in particular the —(CH$_2$)$_7$—CH=CH—CH$_2$—(CH$_2$)$_7$—CH$_3$ or —(CH$_2$)$_7$—CH=CH—(CH$_2$)$_7$—CH$_3$ groups,
provided that R represents at least one group of formula

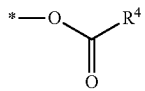

The invention also relates to a pectin bearing hydrophobic groups having the formula:

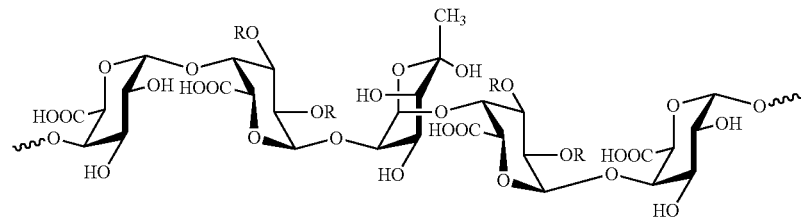

in which
R represents
a hydrogen atom, or
a group of formula

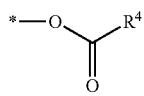

$R^4$ represents
a linear or branched alkyl group containing from 1 to 20 carbon atoms, in particular the $-(CH_2)_{14}-CH_3$ or $-(CH_2)_{16}-CH_3$ groups,
a linear or branched alkenyl group containing 2 to 20 carbon atoms and bearing from 1 to 4 C=C double bonds, conjugated or not, the $-(CH_2)_7-CH=CH-CH_2-(CH_2)_7-CH_3$ or $-(CH_2)_7-CH=CH-(CH_2)_7-CH_3$ groups.
provided that R represents at least one group of formula

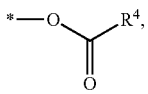

The invention also relates to hyaluronic acid bearing hydrophobic groups having the formula:

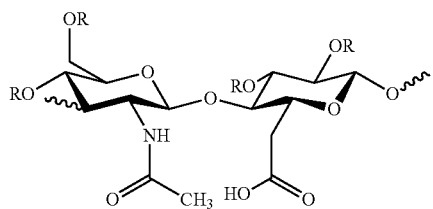

in which
R represents
a hydrogen atom, or
a group of formula

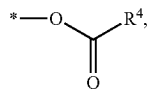

$R^4$ represents
a linear or branched alkyl group containing from 1 to 1000 carbon atoms, in particular the $-(CH_2)_{14}-CH_3$ or $-(CH_2)_{16}-CH_3$ groups,
a linear or branched alkenyl group containing 2 to 1000 carbon atoms and bearing at least one C=C double bond, in particular the $-(CH_2)_7-CH=CH-CH_2-(CH_2)_7-CH_3$ or $-(CH_2)_7-CH=CH-(CH_2)_7-CH_3$ groups,
provided that R represents at least one group of formula

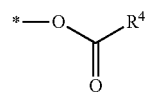

The invention also relates to a chitin bearing hydrophobic groups having the formula:

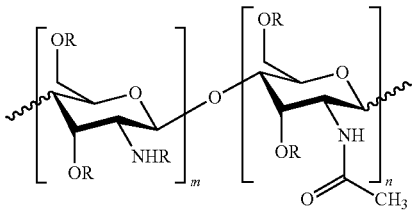

R represents
a hydrogen atom, or
a group of formula

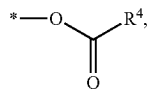

in which
$R^4$ represents
a linear or branched alkyl group containing from 1 to 1000 carbon atoms, in particular the $-(CH_2)_{14}-CH_3$ or $-(CH_2)_{16}-CH_3$ groups,
a linear or branched alkenyl group containing 2 to 1000 carbon atoms and bearing at least one C=C double bond, in particular the $-(CH_2)_7-CH=CH-CH_2-(CH_2)_7-CH_3$ or $-(CH_2)_7-CH=CH-(CH_2)_7-CH_3$ groups, provided that R represents at least one group of formula

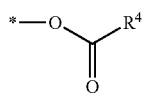

m represents the number of N-glucosamine units, n represents the number of N-acetyl-glucosamine units, provided that the percentage of units n relative to the total number of units is greater than 50%.

In a preferred embodiment, the linear or branched alkyl group containing from 1 to 20 carbon atoms and the linear or branched alkenyl group containing 2 to 20 carbon atoms and bearing from 1 to 4 C═C double bonds, conjugated or not, are selected from the fatty acids.

The invention also relates to a method for preparing an encapsulation system comprising a step of mixing particles containing inclusion complexes according to the invention, with a substance used for its properties in the pharmaceutical, medical, paramedical, medical-device, animal-feed, cosmetic, veterinary, agri-food, pesticide, cosmetotextile, perfumery, and environmental fields (water purification for example) or in the paint, packaging, building and/or car industry, said substance being dissolved beforehand in an aqueous medium such as water, physiological serum, said medium optionally being enriched with glucose or containing any other excipient for pharmaceutical, medical, paramedical, medical-device, animal-feed, cosmetic, veterinary, agri-food, pesticide, cosmetotextile, perfumery, and environmental use (water purification for example) or in the paint, packaging, building and/or car industry, said medium optionally containing a co-solvent selected from ethanol or acetone, or a surfactant selected from the polysorbate derivatives, in particular Tween 80 or Tween 40, to obtain particles containing inclusion complexes containing said substance.

According to a particular embodiment, the method for preparing an encapsulation system according to the invention comprises a step of mixing:
  a polysaccharide comprising hydrophobic groups fixed covalently to the polysaccharide by a nitrogen atom and by oxygen atoms of said polysaccharide,
said polysaccharide being selected from chitosan, dextran, hyaluronic acid, amylose, amylopectin, pullulan, heparin, chitin, cellulose derivatives, heparan sulphate, dermatan sulphate, keratan sulphate, chondroitin sulphate, cellulose sulphate, dextran sulphate, dextrin sulphate, starch, pectin, the alginates, the carrageenans, fucan, curdlan, xylan, polyguluronic acid, xanthan, arabinan, polymannuronic acid, and derivatives thereof, and is in particular chitosan,
  a cyclodextrin designated above,
  a substance used for its properties in the pharmaceutical, medical, paramedical, medical-device, animal-feed, cosmetic, veterinary, agri-food, pesticide, cosmetotextile, perfumery, and environmental fields (water purification for example) or in the paint, packaging, building and/or car industry,
  the percentage by weight of said solvent being in the range from 0 to 50% and in particular equal to approximately 25%,
  the percentage by weight of said polysaccharide being in the range from 0.1% to 15%, and in particular from 0.5% to 5%,
  the percentage by weight of the cyclodextrin being in the range from 0.1% to 15%, and in particular from 0.5% to 5%,
  the percentage by weight of water or of aqueous medium being in the range from 30% to 99.9%, and in particular from 90% to 99%,
to obtain an inclusion complex containing said substance.

The mixing step in the method for preparing an encapsulation system comprises a step of dissolving the active ingredient in an aqueous medium, followed by addition of the amphiphilic polysaccharide and α-cyclodextrin to the medium. The mixture is stirred magnetically for 3 days. In practice, however, it is possible to mix all the components at the same time.

The particles may then be isolated
  either by sedimentation, or by centrifugation if they are microparticles (hydrodynamic diameter greater than a micrometer),
  or by ultracentrifugation or by membrane separation methods such as ultrafiltration and microfiltration, if they are nanoparticles (hydrodynamic diameter less than a micrometer).

DESCRIPTION OF THE FIGURES

FIG. 23 (1) shows an image of the preparation α-cyclodextrin/native chitosan/water (10/1/89)% indicating absence of formation of nanoparticles or microparticles, obtained by transmission electron microscopy.

FIG. 23 (2) shows nanoparticles consisting of α-cyclodextrin/MC6/water (10/1/89)%.

FIG. 24 (1) shows an image of the nanoparticles at the laboratory scale, obtained by transmission electron microscopy.

FIG. 24 (2) shows an image of the nanoparticles at the pilot scale, obtained in transmission electron microscopy.

EXAMPLES

Figure 1:
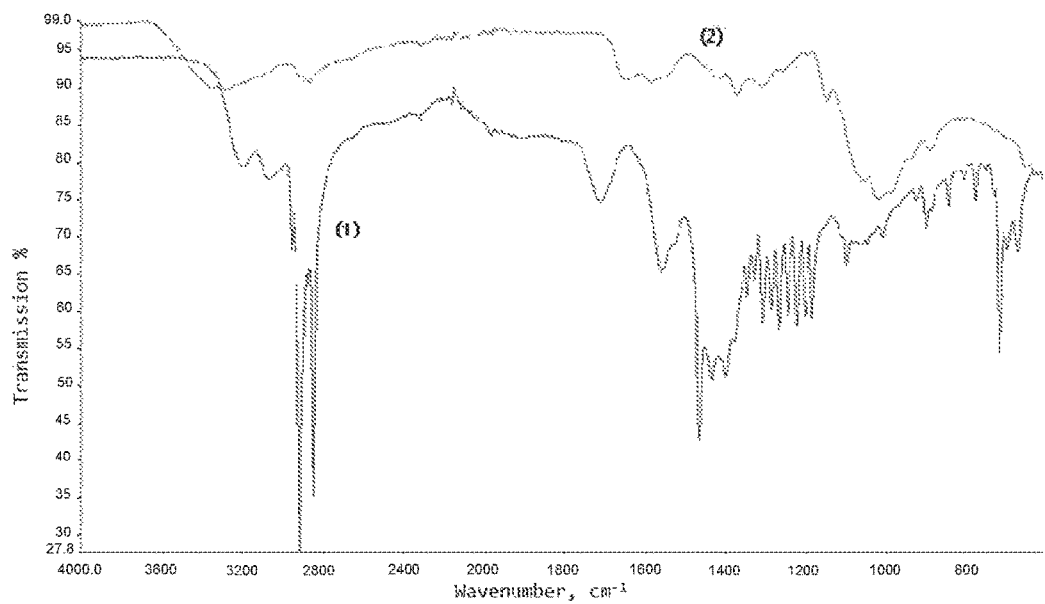
FIG. 1 shows the IR spectrum characteristic of chitosan N-acylated with oleic acid (1) in comparison with that of native chitosan (2).

Meanings of the Abbreviations Used:
CD: cyclodextrin
$CDCl_3$: deuterated chloroform
MC: modified chitosan
$D_2O$: deuterated water
Da: unit of molecular weight in daltons, which corresponds to g/L
DCl: deuterated hydrochloric acid
DDA: degree of deacetylation
$D_h$: hydrodynamic diameter
DMF: dimethylformamide
DMSO-d6: deuterated dimethylsulphoxide
DS: degree of substitution
EDCI: 1-ethyl-3-(3-dimethylaminopropyl)carbodiimide
HSV: human herpes simplex virus
HPV: human papillomavirus
IR: infrared
kDa: kilodalton
kHz: kilohertz
TEM: transmission electron microscopy
MW: molecular weight
MHz: megahertz
$NaNO_2$: sodium nitrite
Q.S.: sufficient quantity
NMR: nuclear magnetic resonance
rpm: revolutions per minute
RSV: respiratory syncytial virus
δ: proton shift, expressed in ppm
MW: molecular weight
PA: palmitic acid
OA: oleic acid
Characteristics/Types of Analytical Equipment Used:
$^1$H-NMR (Bruker ARX, 300 MHz or 500 MHz):

All the N- or O-acylated chitosan compounds obtained were analysed by proton NMR. Depending on the solubility of the acylated polysaccharides, various solvents may be used, such as deuterated water ($D_2O$) with 1% v/v of DCl, deuterated chloroform ($CDCl_3$), deuterated dimethylsulphoxide (DMSO-d6). The spectra are recorded at ambient temperature. If the acylated polysaccharide is sparingly soluble or if the viscosity is high, the samples are heated to 85° C. and an electromagnetic field of 500 MHz is used.

Characterization of the Solid by $^{13}$C-NMR:

The spectra were recorded on an AVANCE II BRUKER spectrometer, using specialized techniques for NMR of solids, in particular magic angle spinning (MAS) and transfer of polarization from $^1$H to $^{13}$C (CP) to avoid the drawbacks connected with the sometimes very long relaxation times in the solid state.

The work was carried out at ωL=500 MHz ($^1$H) and 125.77 MHz ($^{13}$C); the $^1$H/$^{13}$C contact time was fixed at 1.5 ms. These samples were rotated at the magic angle at a frequency of 10 kHz, using a 4-mm rotor.

IR Spectra (ATR-FTIR, FT/IR-4100 Spectrometer, JASCO):

the principle consists of bringing a crystal (diamond) into contact with the sample to be analysed, before the infrared beam is passed through.

Measurements of Particle Size:

The particle sizes were evaluated from the hydrodynamic diameter. The average hydrodynamic diameters of the nanoparticles and microparticles were measured with a Zetasizer nanoseries Nano-ZS90 from the company Malvern instruments SA (Orsay, France) by quasi-elastic light scattering. The samples were diluted beforehand, taking 30 μL of suspension of nanoparticles or microparticles and diluting it in 1 mL of MilliQ® water. The measurements of the hydrodynamic diameters of the microparticles were repeated with a laser granulometer (MasterSizer 2000) from the company Malvern instruments SA (Orsay, France).

Transmission electron microscopy (TEM) was used for observing the microparticles and nanoparticles using a Jeol 1400 60 kV microscope and a camera.

Lyophilization of the Polysaccharides Grafted with Hydrophobic Groups:

Certain derivatives of synthesized polysaccharides were lyophilized using an Alpha 1-2 lyophilizer (Avantec, France) for 48 hours after the solutions had been frozen for at least 12 hours.

Details of the Products Used:

The active ingredients, vitamin B6, paracetamol, ketoprofen, indometacin, caffeine were obtained from the company INRESA, Bartenheim, France. Parsol 1789 is from the company DSM Nutritional Products, Germany.

All the solvents: anhydrous dimethylformamide, dichloromethane, diethyl ether, ethanol, methanol, ammonia, glacial acetic acid (98% (w/w)) were obtained from VWR, France.

Chitosan (of medium viscosity, with molecular weight MW=250 kDa), pullulan, amylopectin, dextran, ɩ-carrageenan, heparin, hyaluronic acid, N-(3-dimethylaminopropyl)-N-ethylcarbodiimide chloride (EDCI), palmitic acid (99% (w/w)), oleic acid (>98% (w/w)), sodium bicarbonate, sodium hydroxide, sodium chloride, sodium nitrite ($NaNO_2$), methanesulphonic acid, palmitoyl chloride, oleoyl chloride, deuterated water, deuterated hydrochloric acid (DCl), deuterated chloroform ($CDCl_3$), deuterated dimethylsulphoxide (DMSO-$d_6$), anhydrous pyridine, triethylamine, Sudan III, hydroxypropyl-β-cyclodextrin (HP-β-CD) were supplied by Sigma-Aldrich Chemical Co, Saint Quentin Fallavier, France. The castor oil was obtained from the company Croda, France. α-Cyclodextrin (α-CD), methyl-β-cyclodextrin (Me-β-CD) Rameb®, degree of substitution ~1.8, MW=1320 g/mol, was purchased from Cyclolab (Budapest, Hungary).

The other chitosans (20 and 145 kDa) were obtained after depolymerization of the commercial chitosan MW=250 kDa according to the technique developed by Huang et al. (*Pharmaceutical Research*, 2004, 21(2), 344): 2 g of commercial chitosan is solubilized overnight in 100 mL of acetic acid (6% v/v), this chitosan solution is then depolymerized by chemical reaction for 1 h with 10 mL of $NaNO_2$ (85 mg/mL). The depolymerized chitosan is then precipitated by increasing the pH to 9 using sodium hydroxide solution (4 mol/L) and recovered by filtration (sintered glass filter No. 4, under vacuum). It is then dissolved in 20 mL of acetic acid (0.1 mol/L) and dialysed (dialysis membrane Spectra/Por, MWCO 3500, batch 3228543, Spectrum laboratories Inc®) against 1 L of distilled water twice for 1.5 h and then overnight, and then lyophilized.

The molecular weight of the depolymerized chitosan is determined by capillary viscosimetry. The flow time (t), in a μ-Ubbelohde microtube (type 53710/I, No. 1016187, R=0.01022 $mm^2/s^2$, Schott Geräte), of solutions of chitosan in a mixture of acetic acid 0.1 mol/L and NaCl 0.2 mol/L at different concentrations (c=0.25/0.50/1.00/1.50/2.00 g/L) is measured at 20° C. (bath CT1450 Schott Geräte and cooling system CK100 Schott Geräte) using an AVS400 viscosimeter (Schott Geräte). For each concentration, the equilibration time is 5 min and five successive measurements are performed. Based on the results obtained, the intrinsic viscosity [η] is deduced, taking the ordinate at the origin of the straight line $t-t_0/t_0C=f(C)$ with $t_0$ the flow time of the mixture of acetic acid 0.1 mol/L and NaCl 0.2 mol/L. The molecular weight is then calculated using the Mark-Houwink-Sakurada equation $\eta=KM_w^a$, with $K=1.81\times10^{-6}$ and a=0.93.

Synthesis of the Polysaccharides Bearing Hydrophobic Groups

Example 1: Synthesis and Characterization of N-Acylated Chitosan

The protocol consists of dissolving 1 g of chitosan (MW=20, 145, 250 kDa), the degree of deacetylation (DDA) of which is equal to 85%, in an aqueous solution of acetic acid at 1% v/v (100 mL) diluted with methanol (75 mL). Oleic acid or palmitic acid is dissolved in 10 mL of methanol and is added to the chitosan solution. A number of moles of EDCI equal to that of the fatty acid is added dropwise to the mixture of fatty acid and chitosan, under continuous magnetic stirring. After reaction for 24 hours, the product is precipitated from a methanol/ammonia mixture, 7/3 v/v. The precipitate is filtered on a sintered glass filter and washed successively with water, methanol and then diethyl ether. Finally, the product is dried under vacuum for 48 hours.

During this reaction, several parameters were varied. In this way it is possible to obtain several types of N-acylated chitosans depending on the type of grafted fatty acid, the degree of grafting (degree of substitution) and the molecular weight of the chitosan.

The IR spectra of the grafted chitosans obtained were recorded. The two curves in FIG. 1 reveal a very wide band between 3430 $cm^{-1}$ and 3440 $cm^{-1}$ corresponding to the OH groups (FIG. 1). The native chitosan has weak absorption at the level of the vibration of the NH groups around 1578 $cm^{-1}$. After N-acylation, it is to be noted that there is weak absorption of its derivatives at bands 3000 $cm^{-1}$ and 3600 $cm^{-1}$ and the appearance of two bands 1636 $cm^{-1}$ and 1657 $cm^{-1}$, characteristic of the carbonyl groups and secondary amides respectively and providing good confirmation of the formation of the amide bond. As for the bands at 2922 $cm^{-1}$, 2853 $cm^{-1}$, 1457 $cm^{-1}$ and 1198 $cm^{-1}$, they correspond to the alkyl chains of the fatty acid.

Comparison of the proton NMR spectra (FIGS. 2 and 3) shows an additional signal with respect to the spectrum of the unmodified chitosan at δ=1.017 ppm. It corresponds to the signal of the methyl group at the end of the fatty acid chain.

Example 2: Characteristics of the Modified Chitosans MC1-MC9

The characteristics of the modified chitosans MC1-MC9 are presented in Table 1 below. The degree of substitution was calculated from the results of elemental analysis of the N-acylated chitosan and of native chitosan.

TABLE 1

| Characteristics of the N-acylated chitosans | | | |
|---|---|---|---|
| Modified chitosan | Grafted hydrophobic group | MW of chitosan used (kDa) | Degree of substitution (%) |
| MC1 | Oleic acid | 250 | 1.19 |
| MC2 | Oleic acid | 250 | 1.67 |
| MC3 | Oleic acid | 250 | 7.43 |
| MC4 | Oleic acid | 145 | 13.47 |
| MC5 | Oleic acid | 20 | 5.61 |
| MC6 | Oleic acid | 20 | 6.35 |
| MC7 | Palmitic acid | 250 | 0.55 |
| MC8 | Palmitic acid | 250 | 13.12 |
| MC9 | Palmitic acid | 250 | 17.01 |

Example 3: Preparation of the Samples of Modified Chitosans, MC1-MC9

Characterization by Proton NMR

For characterization of the N-acylated chitosan by proton NMR, a solution of polymer at a concentration equal to 5 g/L is prepared in deuterated water ($D_2O$) in the presence of deuterated hydrochloric acid (DCl). This step allows exchange of the labile protons of the hydroxyl groups with deuterium atoms. Since the labile protons of the hydroxyl groups all resonate at the same frequency, exchanging them with deuterium atoms makes it possible to remove the residual signal of light water. In order to lower the viscosity, the experiments were recorded at a temperature of 85° C. with an acquisition number and a relaxation delay of 5 and 1 seconds respectively.

Figure 2:
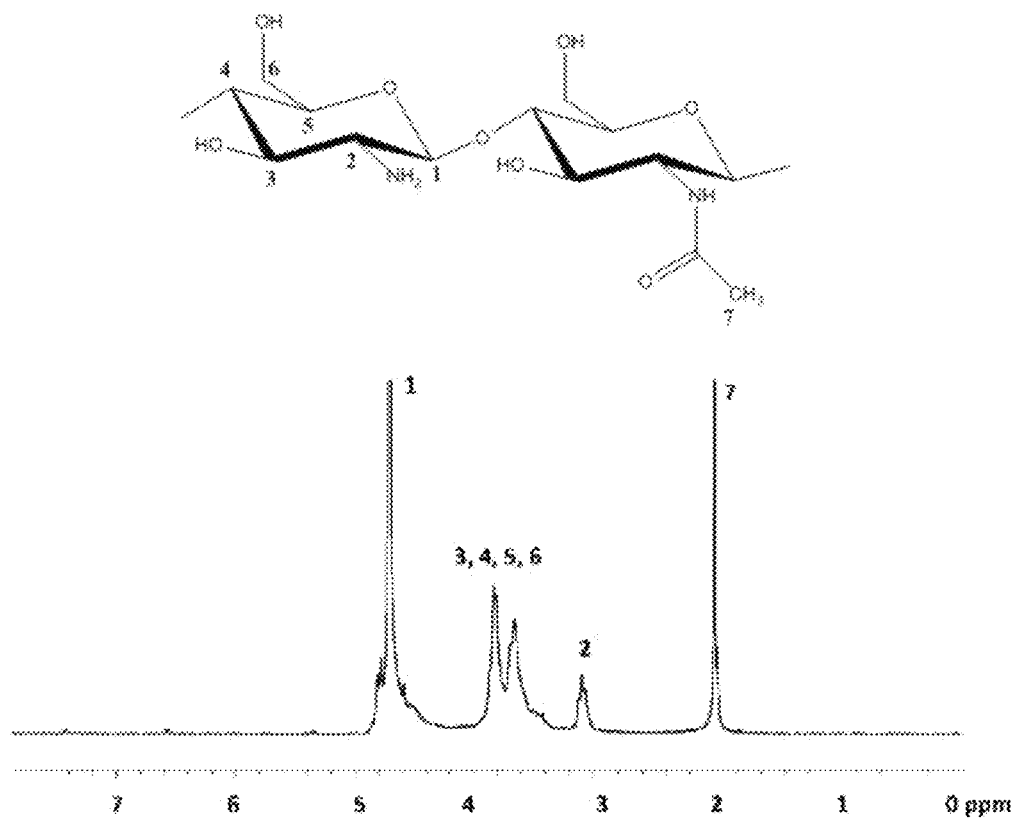
FIG. 2 shows the formula of unmodified chitosan and its $^1$H-NMR spectrum (300 MHz) in DCl at 1% v/v in $D_2O$. The hydrogen atoms are numbered on the formula of the compound, these numbers being shown on the peaks of the NMR spectrum.

$^1$H-NMR (300 MHz) unmodified chitosan: the correspondence of each proton shift is indicated in FIG. 2.

Figure 3:
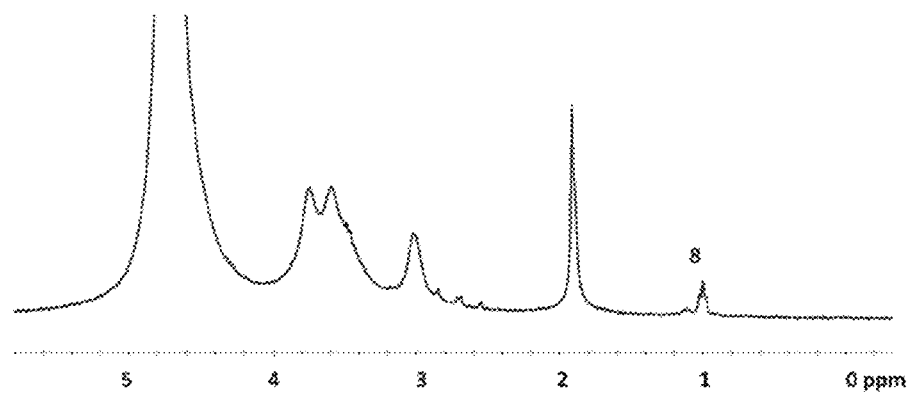
FIG. 3 shows the $^1$H-NMR spectrum (300 MHz) of chitosan after N-acylation with oleic acid dissolved in DCl at 1% v/v in $D_2O$.

$^1$H-NMR (300 MHz) modified chitosan: an additional peak relative to the spectrum of unmodified chitosan appears for a chemical shift equal to $δ_8$=1.017 ppm (FIG. 3). It corresponds to the signal of the fatty acid chain.

Example 4: Synthesis and Characterization of O-Acylated Chitosan

Chitosan (250 kDa, 2 g) is dissolved in 20 mL of methanesulphonic acid, at ambient temperature under continuous magnetic stirring for one hour. The acid chloride (oleic or palmitic) is then added to the reaction mixture. After 5 hours, the mixture is cooled down in an ice bath to stop the reaction; a precipitate forms. The precipitate is dialysed for 12 hours, and then neutralized with sodium bicarbonate. It is then dialysed for 48 hours and lyophilized.

Figure 4:
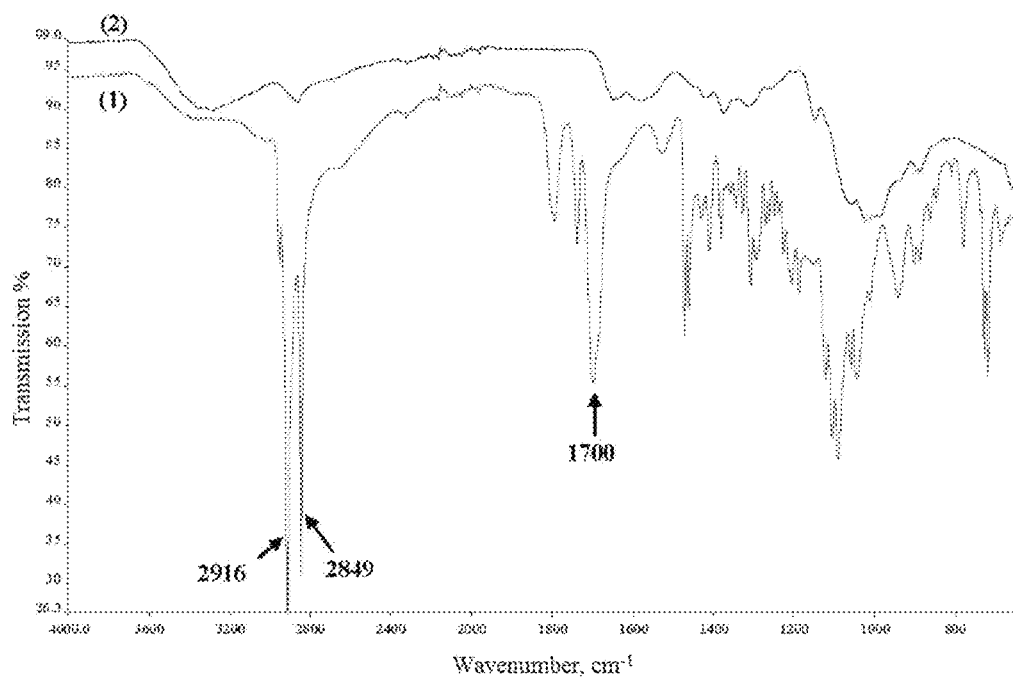
FIG. 4 shows the IR spectrum of O-palmitoyl-chitosan (1) in comparison with native chitosan (2).
Figure 5:
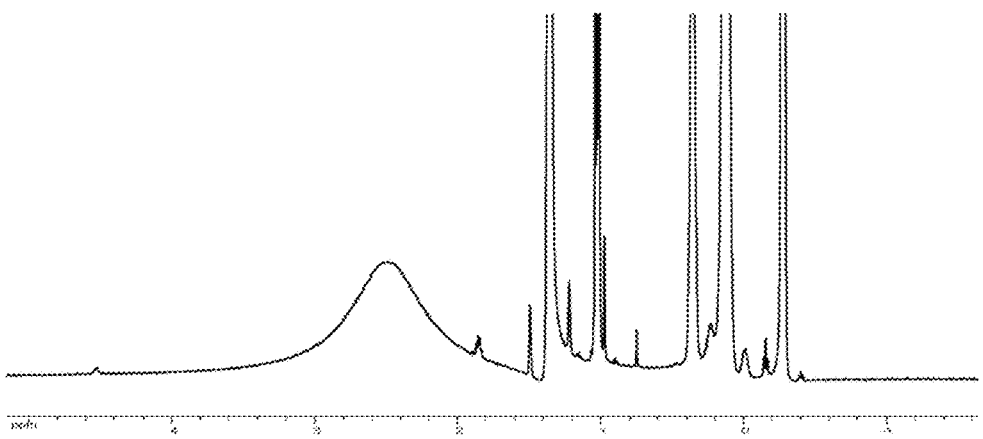
FIG. 5 shows the proton NMR spectrum in DMSO-$d_6$, of O-palmitoyl-chitosan.

The IR spectrum (FIG. 4) of O-palmitoyl-chitosan shows a band characteristic of the carbonyls of an ester group at 1700 cm$^{-1}$, and bands at 2916 cm$^{-1}$, 2849 cm$^{-1}$ corresponding to the alkyl chains of the fatty acid. The proton NMR spectrum (FIG. 5) compared with the spectrum of native chitosan (FIG. 2), shows the appearance of new peaks including those characteristic of the CH$_3$ group at the end of the chain at 0.88 ppm and of the proton of the methylene groups CH$_2$ close to the CO function at 2.8 ppm.

Example 5: Table 2, Characteristics of the Modified Chitosans MC10-MC12

The characteristics of the modified chitosans MC10-MC12 are presented in Table 2 below. The degree of substitution was calculated from the results of elemental analysis of the O-acylated chitosan and of native chitosan.

TABLE 2

Characteristics of the O-acylated chitosans

| Modified chitosan | Grafted hydrophobic group | MW of chitosan used (kDa) | Degree of substitution (%) |
| --- | --- | --- | --- |
| MC10 | Oleic acid | 250 | 1.41 |
| MC11 | Palmitic acid | 250 | 2.25 |
| MC12 | Palmitic acid | 250 | 4.64 |

Example 6: Synthesis and Characterization of Pullulan Grafted with Palmitic Acid O-Palmitoyl-pullulan was prepared according to the reference of Sunamoto et al. (Sunamoto J., Sato T., Taguchi T., Hamazaki H., Naturally occurring polysaccharide derivatives which behave as an artificial cell wall on an artificial liposome, *Macromolecules,* 1992, 25, 5665-5670). Pullulan (5 g) is dissolved in anhydrous dimethylformamide (55 mL) at 60° C. 5 mL of anhydrous pyridine and palmitoyl chloride (5 equivalents per unit of glucose triholoside) are added to the solution obtained. The reaction mixture is stirred at 60° C. for 2 h and then for 1 h at ambient temperature. The mixture is poured into ethanol (350 mL). The precipitate obtained is extracted and washed with ethanol and then with diethyl ether. The white solid obtained is dried under vacuum.

Figure 6:
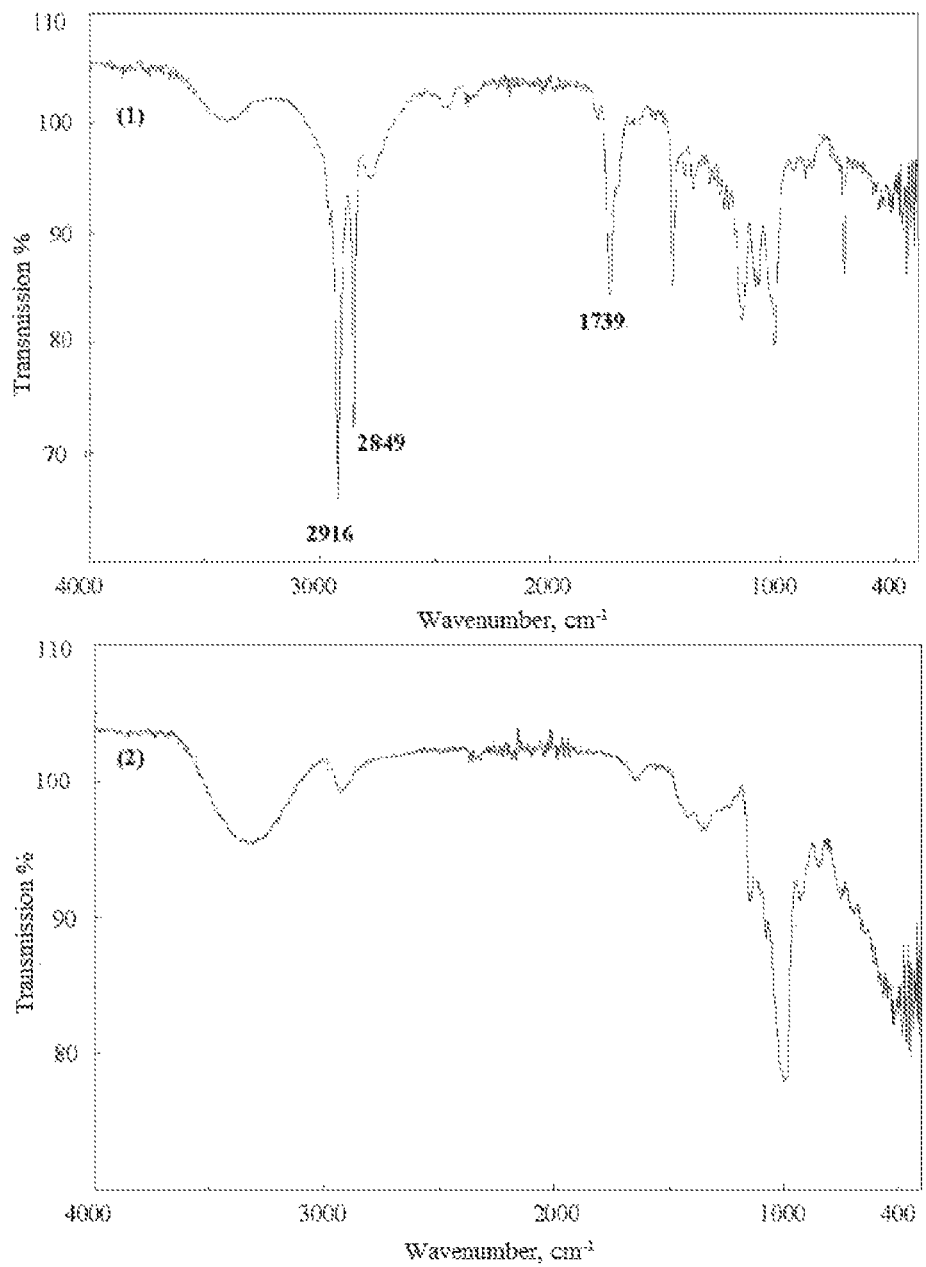
FIG. 6 shows the IR spectrum of O-palmitoyl-pullulan (1) in comparison with that of native pullulan (2).

IR spectrum of O-palmitoyl-pullulan: band at 1739 cm$^{-1}$ corresponding to the carbonyl of the ester group (FIG. 6) and bands at 2916 cm$^{-1}$, 2849 cm$^{-1}$, 1467 cm$^{-1}$ and 1197 cm$^{-1}$, corresponding to the alkyl chains of the fatty acid.

Example 7: Synthesis and Characterization of Derivatives of Amylopectin Grafted with Palmitic Acid Amylopectin (5 g) is mixed with anhydrous dimethylformamide. The mixture is stirred at 70° C. until the polysaccharide has completely dissolved. Then anhydrous triethylamine and palmitoyl chloride are added and then heated under stirring for 2 h. The solution is then diluted in methanol, resulting in precipitation of O-palmitoyl-amylopectin. The white solid obtained is filtered and then dried under vacuum.

Figure 7:
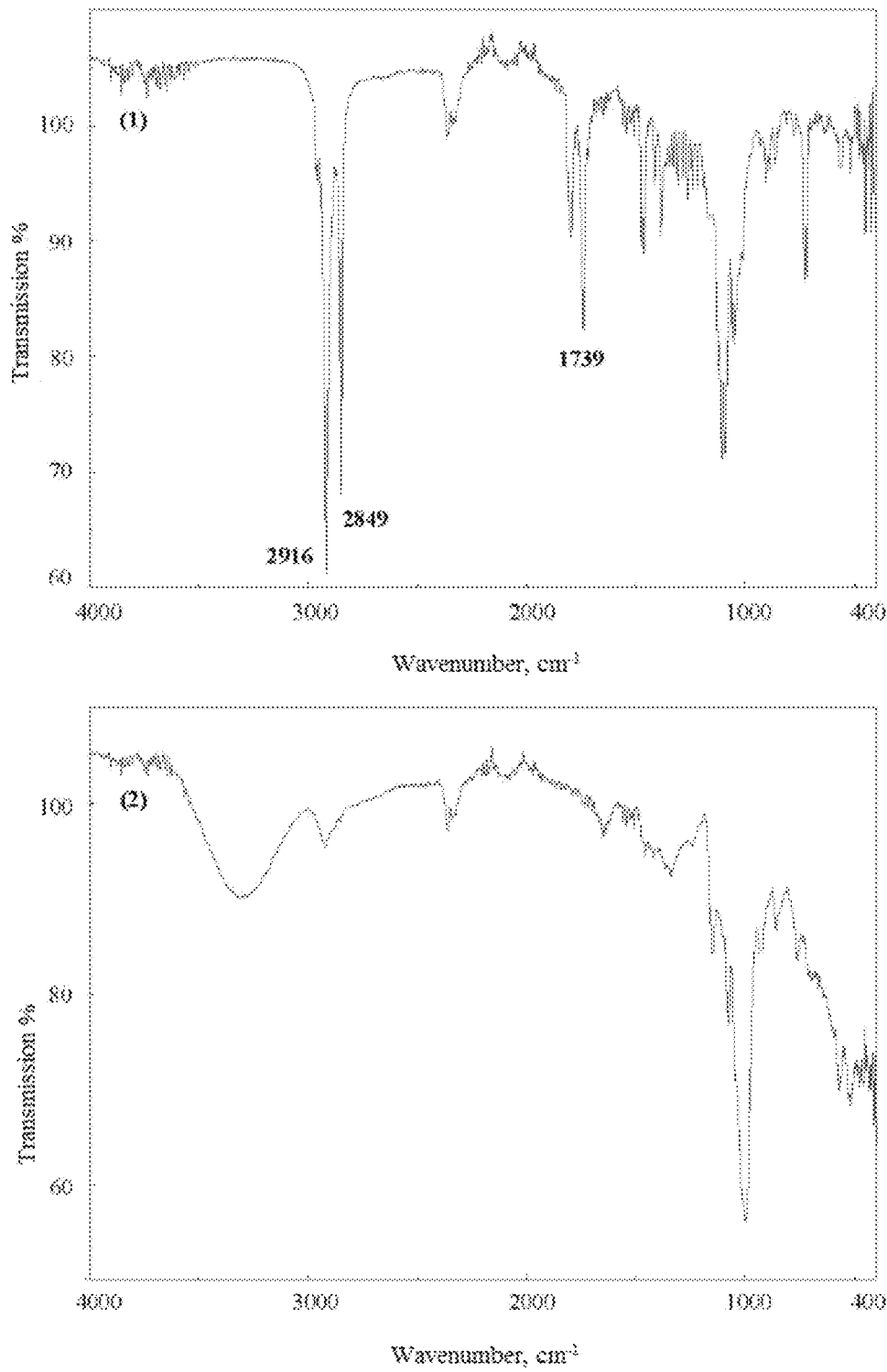
FIG. 7 shows the IR spectrum of O-palmitoyl-amylopectin (1) in comparison with that of native amylopectin (2).

IR spectrum of O-palmitoyl-amylopectin: band at 1739 cm$^{-1}$ corresponding to the carbonyl of the ester group (FIG. 7) and in particular bands at 2916 cm$^{-1}$, 2849 cm$^{-1}$, 1462 cm$^{-1}$ corresponding to the alkyl chains of the fatty acid.

Example 7a: Synthesis and Characterization of Derivatives of Amylopectin Grafted with Palmitic Acid O-Palmitoyl-amylopectin was prepared according to the reference of Sunamoto et al. (Sunamoto J., Sato T., Taguchi T., Hamazaki H., Naturally occurring polysaccharide derivatives which behave as an artificial cell wall on an artificial liposome, *Macromolecules,* 1992, 25, 5665-5670). Amylopectin (5 g) is mixed with 55 mL of anhydrous dimethylformamide at 60° C., under continuous magnetic stirring. 5 mL of anhydrous pyridine, and 1.2 mL of anhydrous DMF containing palmitoyl chloride are added to the solution obtained. The quantity of palmitoyl chloride was varied according to the desired degree of substitution. The reaction mixture is stirred at 60° C. for 2 h and then for 1 h at ambient temperature. The mixture is poured into 350 mL of ethanol. The white solid obtained is dried under vacuum.

Example 8: Synthesis and Characterization of Derivatives of Dextran Grafted with Palmitic Acid Dextran is suspended in anhydrous dimethylformamide. The mixture is stirred at 70° C. until the polysaccharide has completely dissolved. Then anhydrous triethylamine and palmitoyl chloride are added and then heated under stirring for 2 h. The solution is then diluted in methanol, resulting in the precipitation of O-palmitoyl-dextran. The white solid obtained is filtered and then dried under vacuum.

Figure 8:
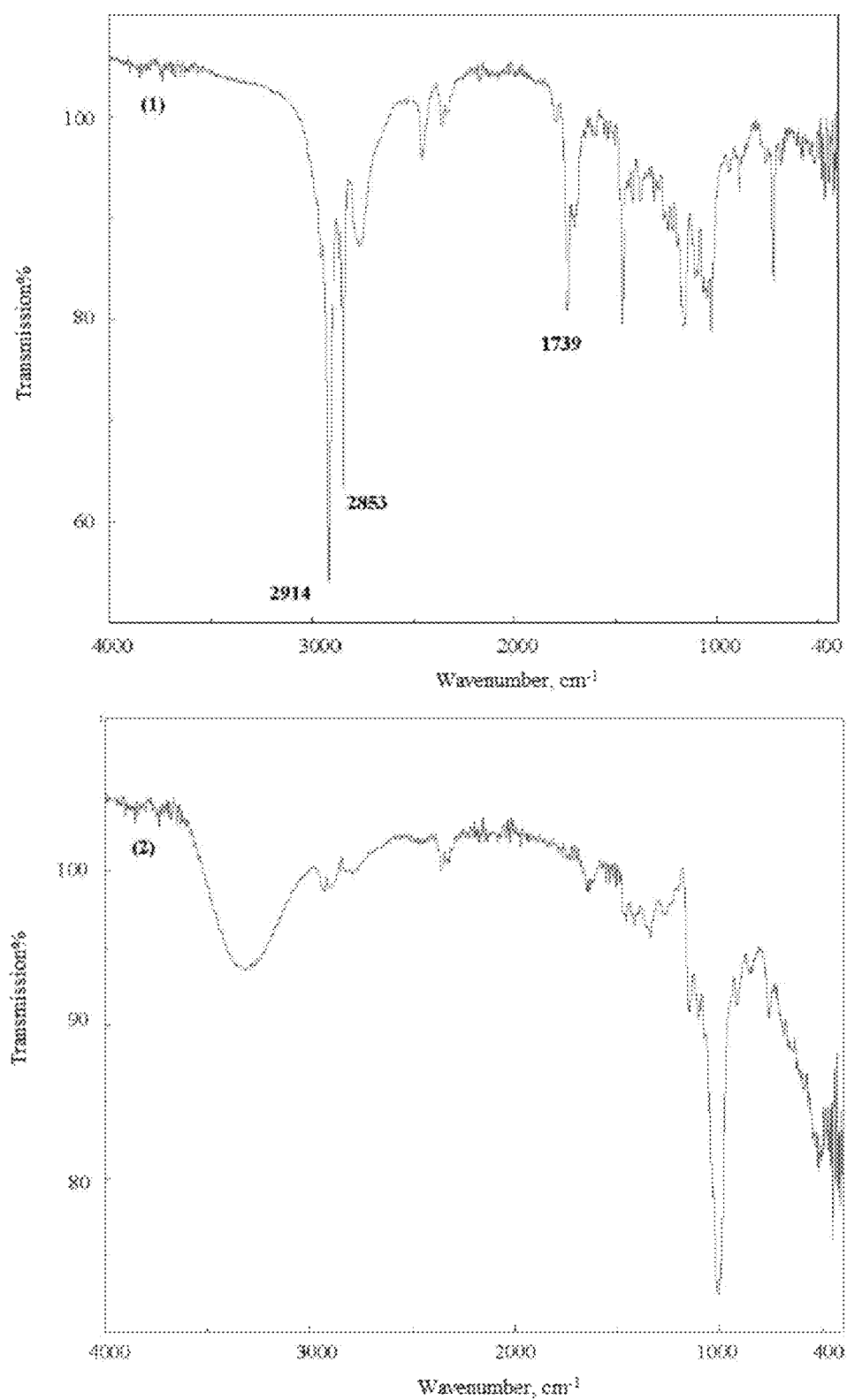
FIG. 8 shows the IR spectrum of O-palmitoyl-dextran (1) in comparison with that of native dextran (2).

IR spectrum of O-palmitoyl-dextran: band at 1739 cm$^{-1}$ corresponding to the carbonyl of the ester group (FIG. 8) and in particular bands at 2914 cm$^{-1}$, 2853 cm$^{-1}$ corresponding to the alkyl chains of the fatty acid.

Example 8a: Synthesis and Characterization of Derivatives of Dextran Grafted with Palmitic Acid O-Palmitoyl-dextran was prepared according to the protocol described by Sunamoto et al. (Sunamoto J., Sato T., Taguchi T., Hamazaki H., Naturally occurring polysaccharide derivatives which behave as an artificial cell wall on an artificial liposome, *Macromolecules,* 1992, 25, 5665-5670). Dextran (5 g) is mixed with 55 mL of anhydrous dimethylformamide at 60° C. 5 mL of anhydrous pyridine and palmitoyl chloride are added to the solution obtained. The reaction mixture is stirred at 60° C. for 2 hours and then for 1 hour at ambient temperature. The mixture is poured into 350 mL of ethanol. The precipitate obtained is extracted and washed with ethanol and then with diethyl ether. The white solid obtained is dried under vacuum.

Figure 8A:
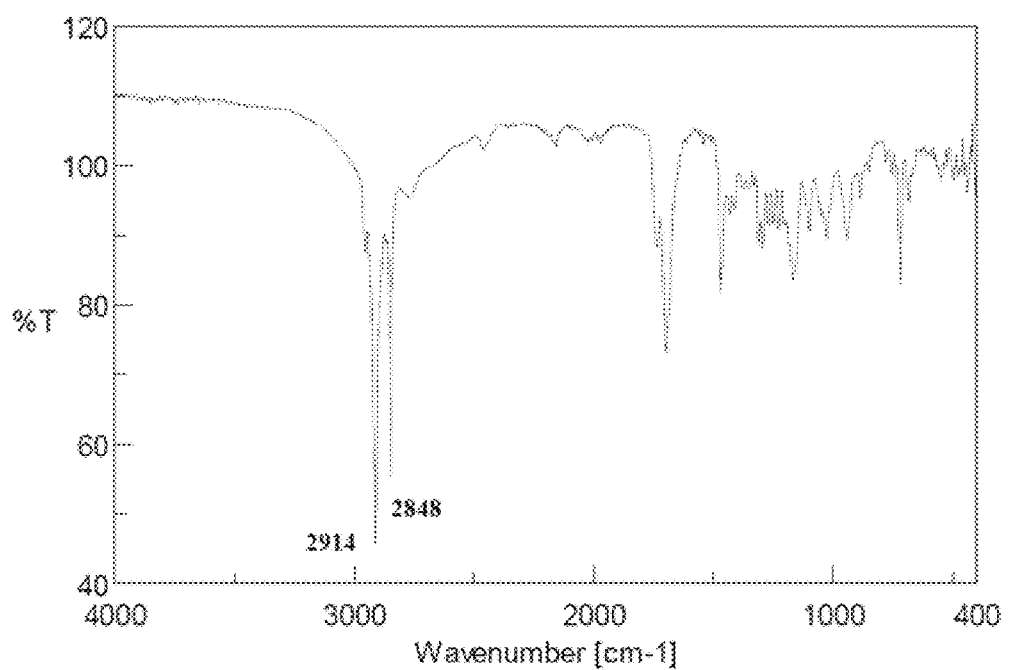
FIG. 8a shows the IR spectrum of O-palmitoyl-dextran.

IR spectrum of O-palmitoyl-dextran (FIG. 8a): bands at 2914 cm$^{-1}$ and at 2848 cm$^{-1}$ corresponding to the alkyl chains of the fatty acid.

Example 9: Synthesis and Characterization of O-Oleoyl-Chitin and O-Palmitoyl-Chitin Synthesis: Chitin was esterified with oleic acid by the method described in the reference (Yang B. Y., Ding Q., Montgomery R., Preparation and physical properties of chitin fatty acids esters, *Carbohydrate Research,* 2009, 344 (3), 336-342). Chitin (7.5 g), dried beforehand under vacuum at 60° C. for 16 hours, is introduced into a mixture of trifluoroacetic acid (75 mL) and palmitic acid or oleic acid (28 g). The mixture is then heated at 70° C. under continuous stirring for 30 min, and then cooled down to ambient temperature. Next, 300 mL of cold absolute ethanol (−20° C.) is added, and the mixture is concentrated in a rotary evaporator at a temperature of 20° C. under vacuum. The product obtained is dispersed in absolute ethanol and heated to 80° C. After decanting and removing the supernatant, the end product is dried and dissolved in 30 mL of DMF and then centrifuged at 3600 g.

Esterification of chitin with palmitic acid or oleic acid is carried out in the presence of trifluoroacetic acid, which is known to be a promoter of esterification for other polysaccharides, in particular starch cited in the reference (Yang B. Y., Montgomery R., Acylation of Starch using Trifluoroacetic Anhydride Promoter, *Starch—Stärke*, 2006, 58 (10), 520-526). In fact, trifluoroacetic acid leads to the formation of the acid anhydride, which is much more reactive than the carboxylic acid itself. Being strongly electronegative and highly acidic, trifluoroacetic acid leads to the protonation of the amine functions, thus permitting preferential esterification on the alcohol functions.

Figure 9:
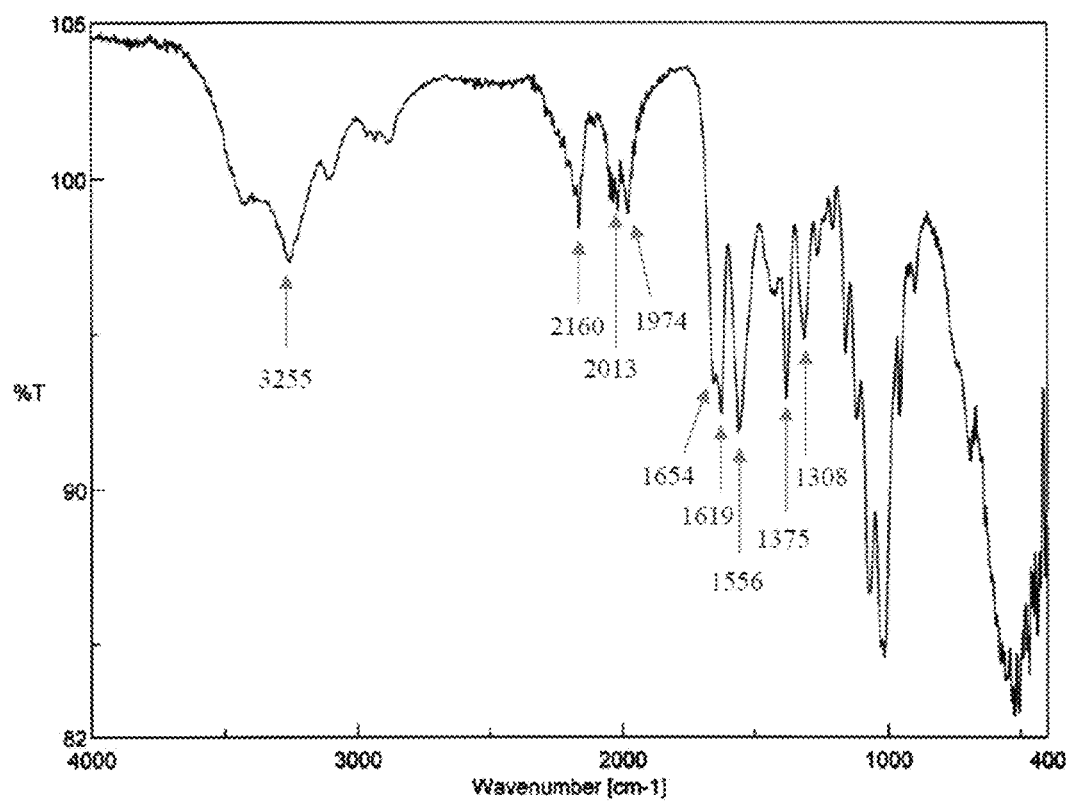
FIG. 9 shows the IR spectrum of chitin esterified with palmitic acid (1) in comparison with that of native chitin (2).

Characterization of O-oleoyl-chitin and O-palmitoyl-chitin: Analysis by infrared spectroscopy is a quick and efficient method for identifying the chemical groups of the esterified chitin in comparison with the spectrum of native chitin. The spectrum shown in FIG. 9 is typical of chitin; the frequency of the carbonyl regions (CO) of the amides between 1600 $cm^{-1}$ and 1500 $cm^{-1}$ is of high intensity. The band corresponding to amide I is divided into two peaks at 1654 $cm^{-1}$ and 1619 $cm^{-1}$. The band corresponding to amide II is single and is at 1556 $cm^1$.

Figure 9A:
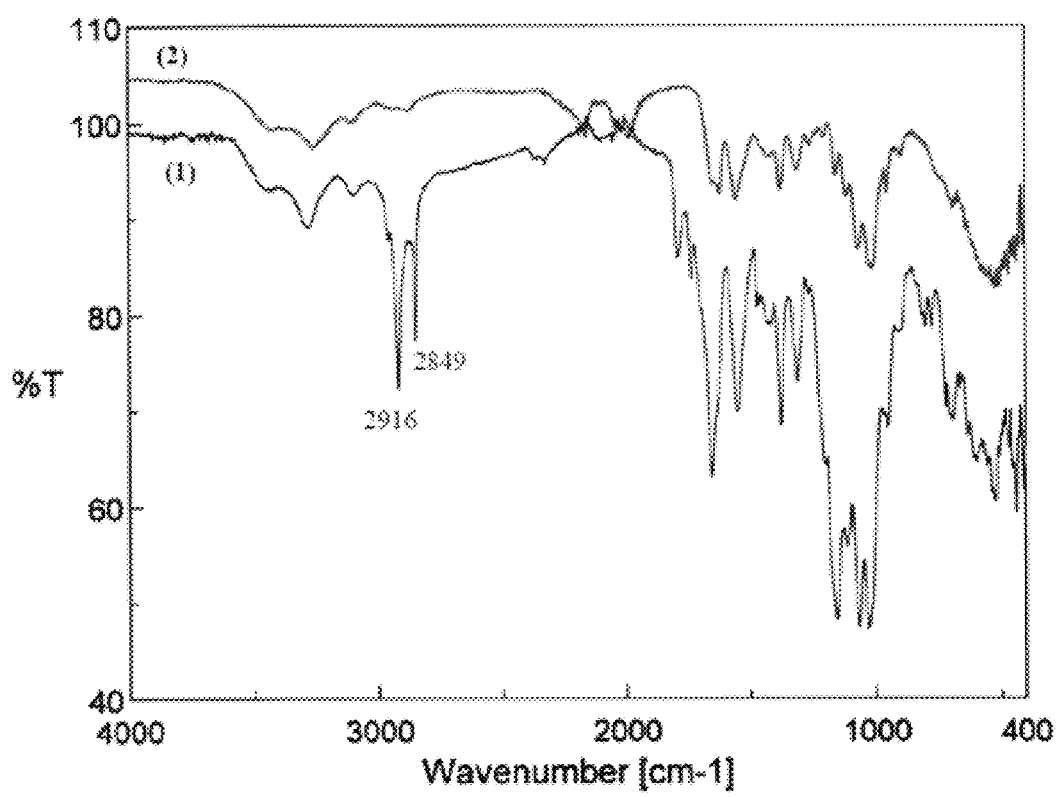
FIG. 9a shows the IR spectrum of O-palmitoyl-chitin.

Regarding the spectrum obtained for O-palmitoyl-chitin (FIG. 9a), greater absorption is observed for the bands at 1649 $cm^{-1}$ and 1554 $cm^{-1}$, which explains the presence of the carbonyl groups CO and amide II, thus demonstrating N-acylation of the free amine functions of the chitin. FIG. 9a (1) also shows bands at 2916 $cm^{-1}$ and at 2849 $cm^{-1}$ corresponding to the alkyl chains of the fatty acid.

Figure 10:
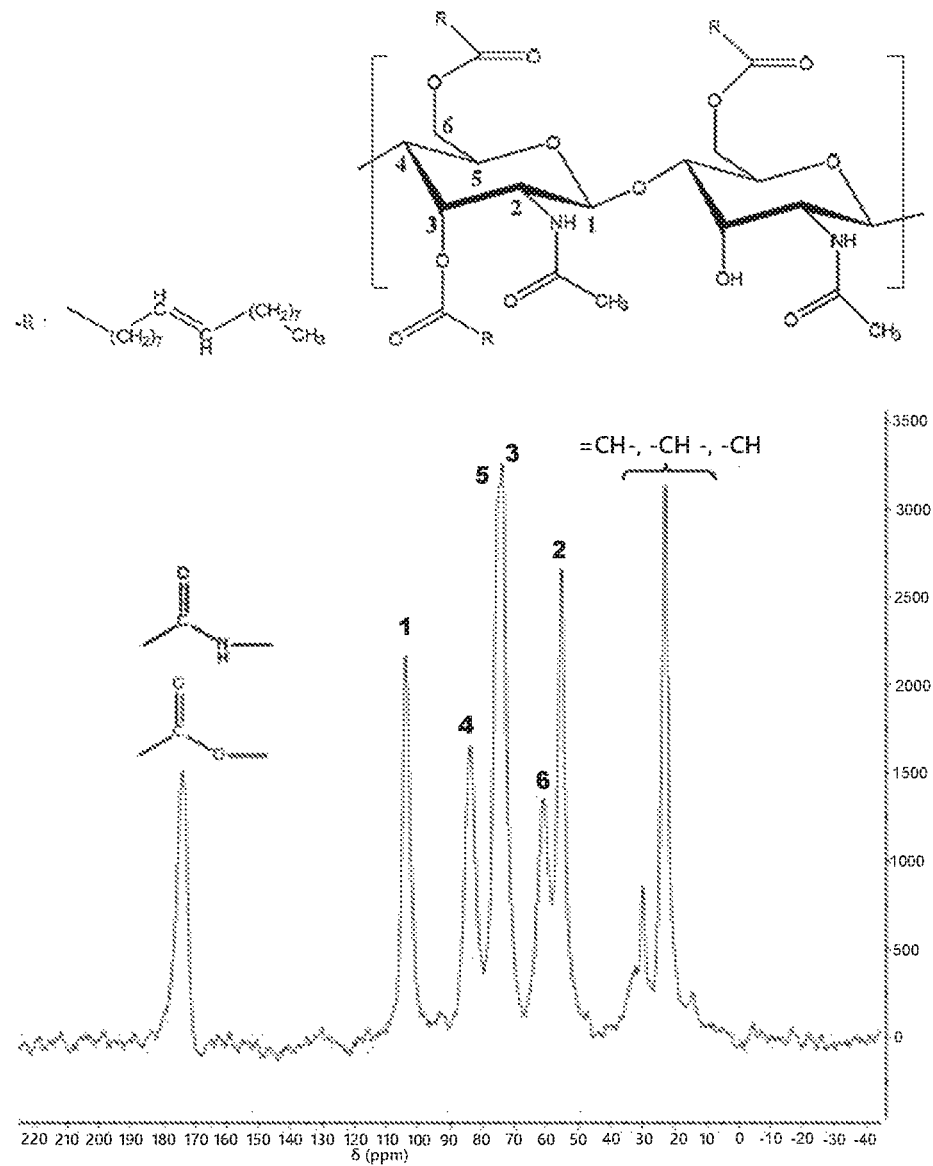
FIG. 10 shows the $^{13}$C-NMR spectrum in the solid state of O-oleoyl-chitin.

Characterization by $^{13}C$-NMR of the solid of the chitin esterified with oleic acid is particularly suitable for characterization of this derivative, which is insoluble in water and in the majority of organic solvents. The spectrum presented in FIG. 10 shows the presence of 9 resonance peaks with the values presented in Table 3 below.

TABLE 3

Shifts obtained in NMR of the solid carbon of O-oleoyl-chitin expressed in ppm and the corresponding functions

| Function | Shift (ppm) |
| --- | --- |
| =CH—, —$CH_2$—, —$CH_3$ | 14.29, 22.93, 29.81 |
| C2 | 55.35 |
| C6 | 60.96 |
| C3-C5 | 73.87 |
| C4 | 83.85 |
| C1 | 104.03 |
| C=O amide and ester | 173.79 |

Example 10: Synthesis of Heparin Grafted with Palmitic Acid DS1

Introduce 1 g of heparin into 11 mL of anhydrous DMF. Heat gradually at 60° C. under magnetic stirring. Add 5 mL of anhydrous pyridine and then 2.5 g of palmitoyl chloride in 6 mL of anhydrous DMF. Stir the mixture under magnetic stirring for 2 h at 60° C. and then for 1 h at ambient temperature. Pour the mixture into 100 mL of cold ethanol in order to obtain a precipitate. Extract and wash the precipitate with 100 mL of ethanol and then 100 mL of diethyl ether.

Example 10a: Synthesis and Characterization of Heparin Grafted with Palmitic Acid DS2

Synthesis: Heparin (2 g) is dissolved in 10 mL of dichloromethane and 2 mL of palmitic acid chloride contained in a flask. The flask is placed under reflux under continuous magnetic stirring for 72 h at ambient temperature. Next, 20 mL of a solution of sodium acetate in methanol is added to the reaction mixture. The precipitate formed is recovered on a sintered glass filter of porosity No. 4, then washed with 100 mL of methanol and then 100 mL of acetone. The solid is dried under vacuum at ambient temperature. The heparin esterified with palmitic acid is purified by dissolving in 10 mL of distilled water and the addition of NaCl until a concentration of NaCl of 10% w/v is reached. Next, 20 mL of methanol is added and the precipitate formed is recovered on a sintered glass filter and then washed with 100 mL of ethanol and then 100 mL of acetone. The solid is dried under vacuum at ambient temperature.

Figure 11:
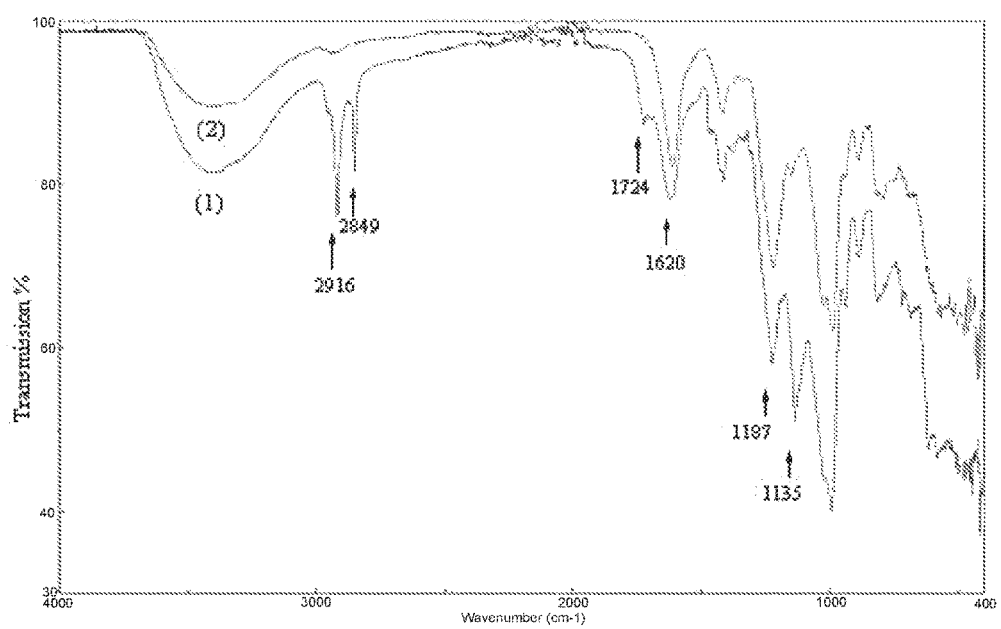
FIG. 11 shows the IR spectrum characteristic of O-palmitoyl-heparin (1) in comparison with native heparin (2).

Characterization of O-palmitoyl-heparin: Analysis by infrared spectroscopy (FIG. 11) showed the presence of bands at 1620 and 1724 $cm^{-1}$, which correspond to the carbonyl groups of the ester function. The bands at 1135 and 1187 $cm^{-1}$ correspond to the C—O groups of the ester function. The spectrum of O-palmitoyl-heparin also showed bands at 2849 and 2916 $cm^{-1}$ corresponding to the alkyl groups of palmitic acid.

Example 11: Synthesis and Characterization of Carrageenan Grafted with Palmitic Acid Synthesis: Carrageenan (2 g) is suspended in 10 mL of dichloromethane and 1, 2 or 3 mL of palmitic acid chloride contained in a flask. The O-palmitoyl-carrageenans obtained are designated DS1, DS2 and DS3 according to the quantity of acid chloride used in the reaction. The flask is placed under reflux under continuous magnetic stirring for 72 h at 30° C. Next, the solid is recovered on a sintered glass filter and then washed twice with 100 mL of ethanol. The solid is dried under vacuum at ambient temperature for 12 h.

Figure 12:
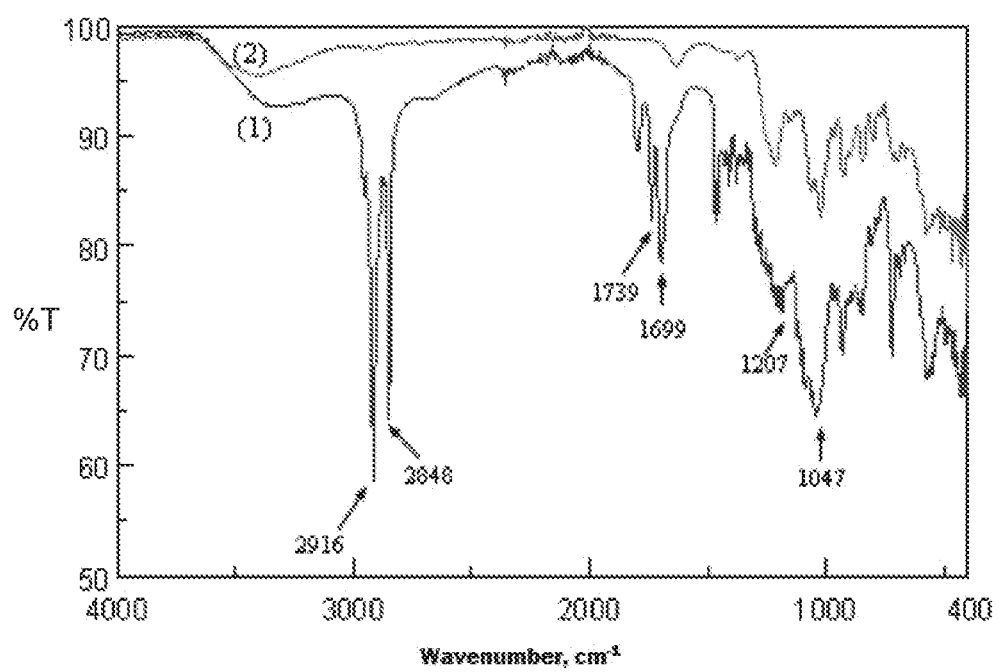
FIG. 12 shows the IR spectrum characteristic of O-palmitoyl-carrageenan (1) in comparison with native carrageenan (2).

Infrared characterization (FIG. 12): Characterization of O-palmitoyl-carrageenan by infrared spectroscopy showed the presence of bands at 1699 $cm^{-1}$ and 1739 $cm^{-1}$, which correspond to the carbonyl groups of the ester function. The bands at 1047 $cm^{-1}$ and 1207 $cm^{-1}$ correspond to the C—O groups of the ester function. The spectrum of O-palmitoyl-carrageenan also showed bands at 2848 $cm^{-1}$ and 2916 $cm^{-1}$ corresponding to the alkyl groups of palmitic acid.

Example 12: Synthesis and Characterization of Hyaluronic Acid Grafted with Palmitic Acid Hyaluronic acid (2 g) is mixed with 10 mL of dichloromethane and 2 mL of palmitic acid chloride contained in a flask. The flask is placed under reflux under continuous magnetic stirring for 5 days at 30° C. Next, the solid is recovered on a sintered glass filter and then washed twice with 100 mL of acetone. The solid is dried under vacuum at ambient temperature for 12 h.

Figure 13:
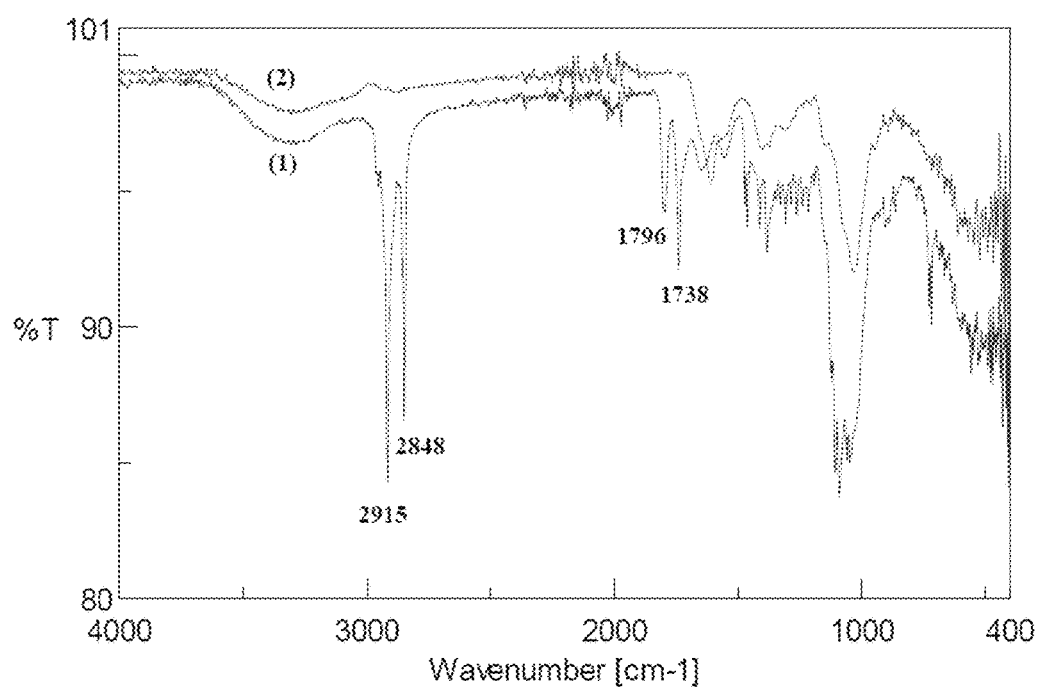
FIG. 13 shows the IR spectrum characteristic of O-palmitoyl-hyaluronic acid (1) in comparison with native hyaluronic acid (2).

Infrared characterization (FIG. 13): Characterization of O-palmitoyl-hyaluronic acid by infrared spectroscopy showed the presence of bands corresponding to the carbonyl groups of the ester function. The bands at 1048 and 1207 cm$^{-1}$ correspond to the C—O groups of the ester function. The spectrum of O-palmitoyl-hyaluronic acid also showed bands at 2848 and 2915 cm$^{-1}$ corresponding to the alkyl groups of palmitic acid.

Example 13: Formation of Microparticles and Nanoparticles from α-Cyclodextrin and Acylated Polysaccharides: N-Palmitoyl-Chitosan and O-Oleoyl-Chitosan The microparticles and nanoparticles were formed from α-cyclodextrin and polysaccharide grafted with fatty acids. The examples of the polysaccharides used are presented in the table below. The protocol consists of weighing the α-cyclodextrin and the O- or N-acylated polysaccharide in a small flask. Next, distilled water is added to the mixture of α-cyclodextrin and the O- or N-acylated polysaccharide. The mixture is magnetically stirred for 3 days.

TABLE 4

Sizes of the particles obtained from N-acylated or O-acylated chitosan

| polysaccharide | Molecular weight (kDa) | Fatty acid | DS (%) | Percentage by weight of amphiphilic polysaccharide | Percentage by weight of α-cyclodextrin | Percentage by weight of water | Particle size (nm)* |
|---|---|---|---|---|---|---|---|
| N-acylated chitosan | 250 | PA | 13.12 | 1 | 10 | 89 | 7320 ± 1823 |
| O-acylated chitosan | 250 | OA | 4.64 | 1 | 10 | 89 | 2090 ± 367 |

*Hydrodynamic diameter expressed by volume.

Figure 14:
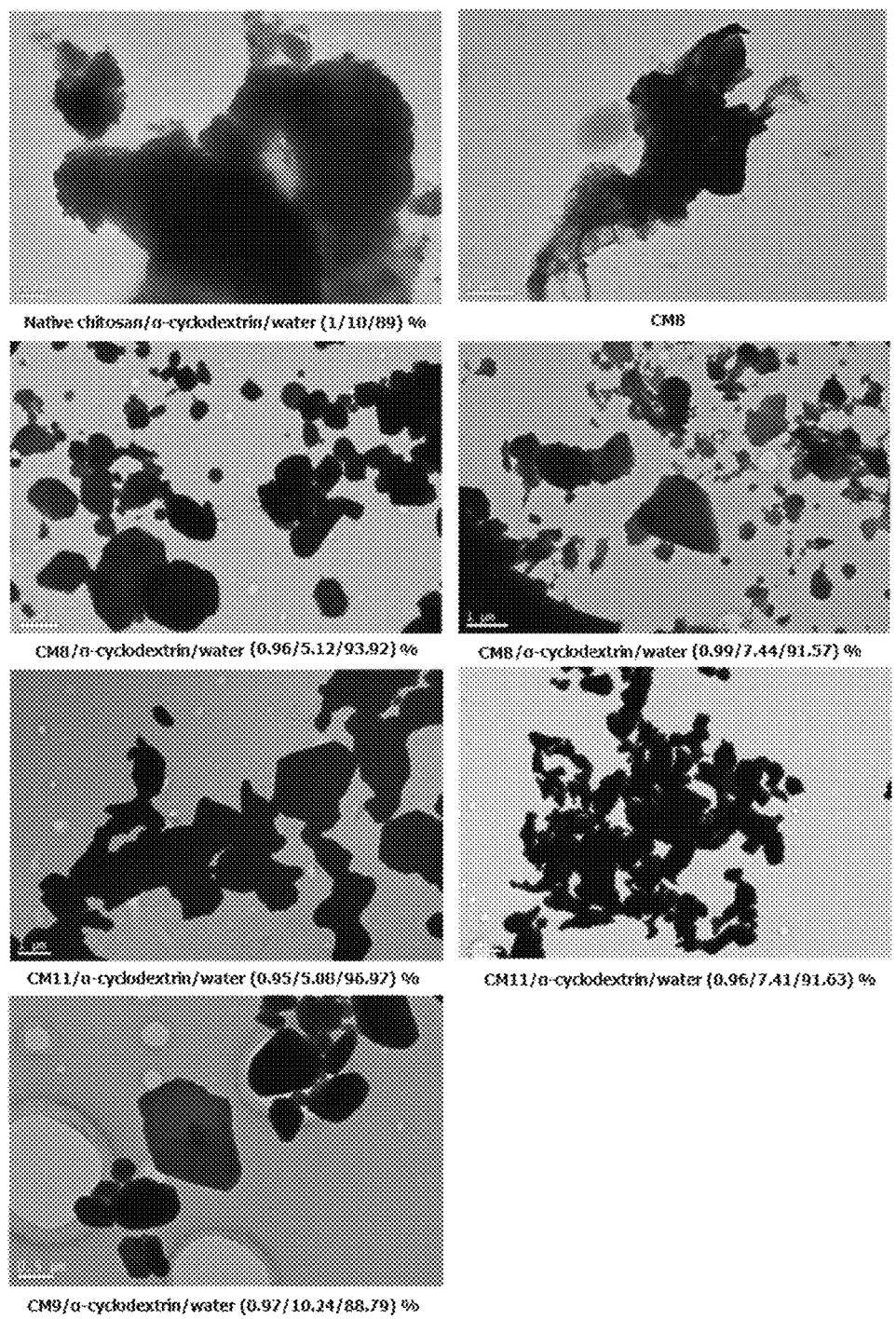
FIG. 14 shows the images of different preparations of particles, obtained by transmission electron microscopy.
Figure 15:
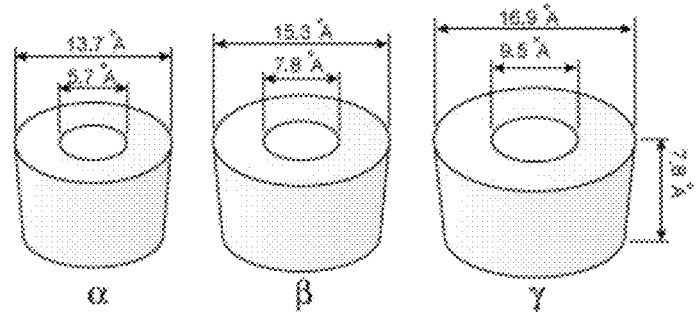
FIG. 15 shows the α, β and γ cyclodextrins. In the figure, the dimensions are given in Angstroms.

An example of an image of particles observed using transmission electron microscopy is shown in FIG. 14.

Example 14: Encapsulation of Water-Soluble Active Ingredients

The protocol adopted for encapsulating the hydrophilic active ingredients is to dissolve the active ingredient in water at an initial concentration as indicated in Table 5 and then adding the amphiphilic polysaccharide and the α-cyclodextrin. The mixture is magnetically stirred for 3 days. After this mixing for 3 days, the concentration of the active ingredient that has not been encapsulated is determined in the supernatant of the preparation. The supernatant is separated either by simple sedimentation or by centrifugation of the microparticles, or after ultracentrifugation in the case of the nanoparticles.

TABLE 5

Example of active molecules encapsulated.

| | Polysaccharide used | Initial concentration of active molecules (g/L) | Concentration encapsulated (g/L) | Encapsulation yield (%) |
|---|---|---|---|---|
| Vitamin B6 | MC8 | 194 | 104.65 | 53.94 |
| Vitamin B6 | MC9 | 2.31 | 1.52 | 65.82 |

TABLE 5-continued

Example of active molecules encapsulated.

| | Polysaccharide used | Initial concentration of active molecules (g/L) | Concentration encapsulated (g/L) | Encapsulation yield (%) |
|---|---|---|---|---|
| Paracetamol | MC11 | 2.34 | 0.78 | 33.33 |
| Caffeine | MC8 | 21.7 | 3.15 | 17.53 |
| Caffeine | MC6 | 21.7 | 3.59 | 16.55 |
| Caffeine | MC9 | 2.33 | 0.51 | 22.23 |

Example 15: Preparation and Characterization of Nanoparticles Composed of O-Palmitoyl-Heparin DS1

Figure 16:
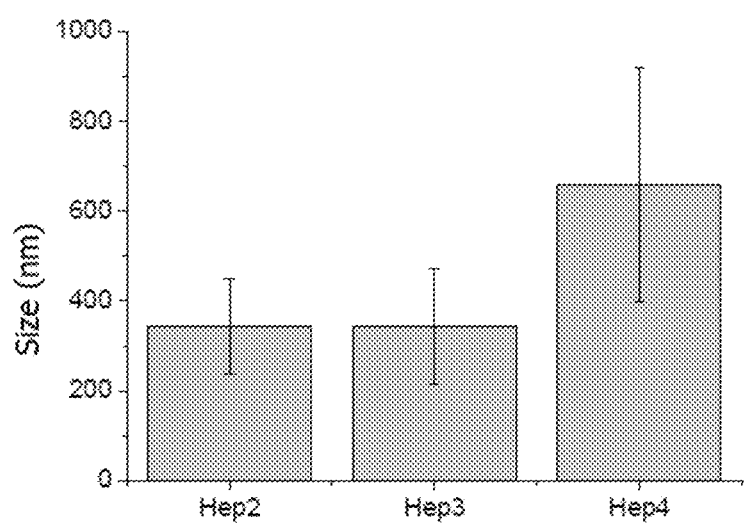
FIG. 16 shows the effect of the concentration of O-palmitoyl-heparin DS 1% on the $D_h$ of the nanoparticles.

The protocol consists of weighing O-palmitoyl-heparin DS1 and α-cyclodextrin in a flask. Next, water is added to the mixture. The whole is mixed for 72 h at ambient temperature using a magnetic stirring bar. The concentrations of O-palmitoyl-heparin DS1 and of α-cyclodextrin are shown in Table 6. The results of the measurements of the hydrodynamic diameters are shown in Table 6 and FIG. 16.

TABLE 6

Effect of varying the concentration of O-palmitoyl-heparin on the hydrodynamic diameter of the nanoparticles composed of heparin DS2

| Name | Concentration of α-CD (g/L) | Concentration of O-palmitoyl-heparin DS1 (g/L) | Concentration ratio α-CD/O-palmitoyl-heparin DS1 | $D_h$ (nm) |
|---|---|---|---|---|
| Hep1 | 0 | 10 | 0 | No formation of particles |
| Hep2 | 100 | 10 | 10 | 344 ± 105 |
| Hep3 | 100 | 5 | 20 | 344 ± 128 |
| Hep4 | 100 | 2.5 | 40 | 659 ± 260 |

Example 16: Preparation and Characterization of Nanoparticles Consisting of O-Palmitoyl-Heparin DS2

Figure 17:
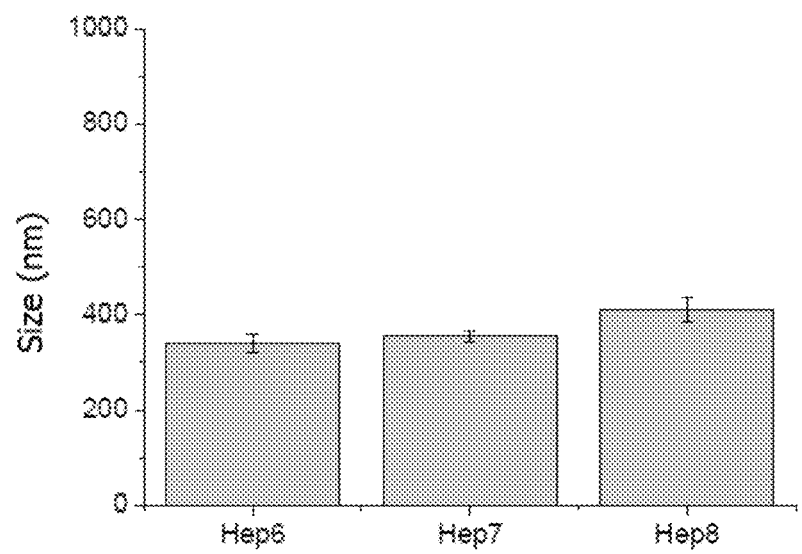
FIG. 17 shows the effect of the concentration of α-CD on the $D_h$ of the microparticles consisting of O-palmitoyl-heparin DS2.

O-Palmitoyl-heparin DS2 and α-cyclodextrin were weighed in a flask. Next, water is added to the mixture. The whole is mixed for 72 h at ambient temperature using a magnetic stirring bar. The concentrations of O-palmitoyl-heparin DS2 and of α-cyclodextrin are shown in Table 7. The results of the measurements of the hydrodynamic diameters are shown in Table 7 and FIG. 17.

TABLE 7

Effect of varying the concentration of α-CD on the hydrodynamic diameter of the nanoparticles consisting of heparin DS2

| Name | Concentration of α-CD (g/L) | Concentration of O-palmitoyl-heparin DS2 (g/L) | Concentration ratio α-CD/O-palmitoyl-heparin DS2 | $D_h$ (nm) |
|---|---|---|---|---|
| Hep5 | 0 | 10 | 0 | No formation of particles |
| Hep6 | 100 | 10 | 10 | 340 ± 19 |
| Hep7 | 50 | 10 | 5 | 355 ± 11 |
| Hep8 | 25 | 10 | 2.5 | 410 ± 24 |

Figure 18:
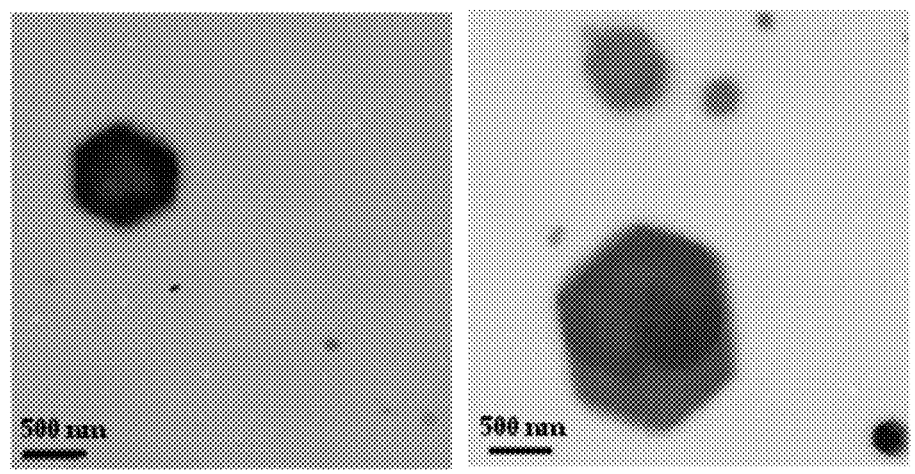
FIG. 18 shows TEM observation of the particles consisting of O-palmitoyl-heparin DS2.

FIG. 18 shows an example of images obtained by observations using transmission electron microscopy of the nanoparticles consisting of heparin DS2. These images, obtained without contrast agents, show that these nanoparticles self-assemble in a well-structured manner in the form of a hexagon.

Example 17: Preparation and Characterization of Microparticles of O-Palmitoyl-Carrageenan DS1

O-Palmitoyl-carrageenan DS1 as well as α-cyclodextrin are weighed in a flask. Next, water is added to the mixture. The whole is mixed for 72 h at ambient temperature using a magnetic stirring bar The concentrations of O-palmitoyl-carrageenan and of α-cyclodextrin, and the results of the measurements of the hydrodynamic diameters, are shown in Table 8.

TABLE 8

Figure 19:
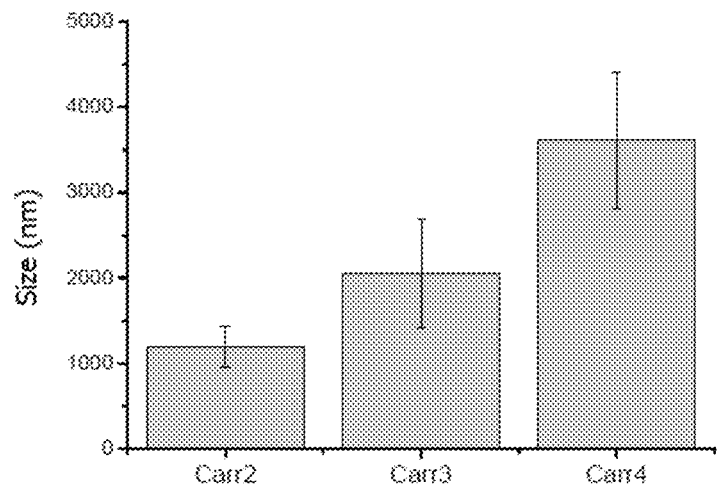
FIG. 19 shows the effect of the concentration of α-CD on the $D_h$ of the microparticles consisting of O-palmitoyl-carrageenan DS1.

Effect of varying the concentration of α-CD on the hydrodynamic diameter of the microparticles consisting of carrageenan DS1
Variation in the quantity of α-cyclodextrin (FIG. 19)

| Name | Concentration of α-CD (g/L) | Concentration of O-palmitoyl-carrageenan DS1 (g/L) | Concentration ratio α-CD/O-palmitoyl-carrageenan DS1 | $D_h$ (nm) |
|---|---|---|---|---|
| Carr1 | 0 | 10 | 0 | No formation of particles, the product is insoluble in water |
| Carr2 | 100 | 10 | 10 | 1196 ± 242 |
| Carr3 | 51 | 10 | 5 | 2053 ± 642 |
| Carr4 | 27 | 10 | 2.7 | 3613 ± 800 |

TABLE 9

Figure 20:
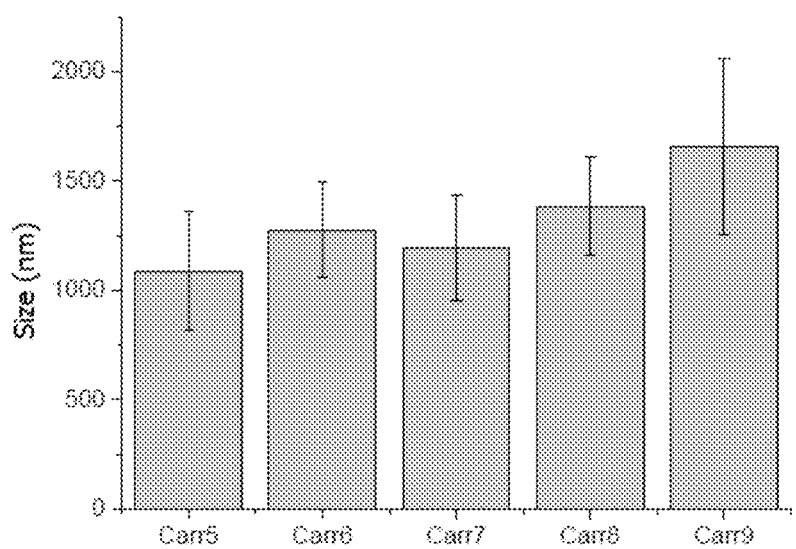
FIG. 20 shows the effect of the concentration of O-palmitoyl-carrageenan DS1 on the $D_h$ of the microparticles.

Effect of varying the concentration of O-palmitoyl-carrageenan on the hydrodynamic diameter of the microparticles consisting of carrageenan DS1
Variation in the quantity of O-palmitoyl-carrageenan DS1 (FIG. 20)

| Name | Concentration of α-CD (g/L) | Concentration of O-palmitoyl-carrageenan DS1 (g/L) | Concentration ratio α-CD/O-palmitoyl-carrageenan DS1 | $D_h$ (nm) |
|---|---|---|---|---|
| Carr5 | 100 | 2.5 | 40 | 1089 ± 272 |
| Carr6 | 100 | 5 | 20 | 1277 ± 218 |
| Carr7 | 100 | 10 | 10 | 1196 ± 242 |
| Carr8 | 100 | 20 | 5 | 1384 ± 225 |
| Carr9 | 100 | 30 | 3.3 | 1658 ± 403 |

Example 18: Preparation and Characterization of Microparticles and Nanoparticles of O-Palmitoyl-Carrageenan DS2

O-Palmitoyl-carrageenan DS2 and α-cyclodextrin are weighed in a flask. Next, water is added to the mixture. The whole is mixed for 72 h at ambient temperature using a magnetic stirring bar. The concentrations of O-palmitoyl-carrageenan and of α-cyclodextrin, and the results of the measurements of the hydrodynamic diameters, are shown in Table 10.

TABLE 10

Figure 21:
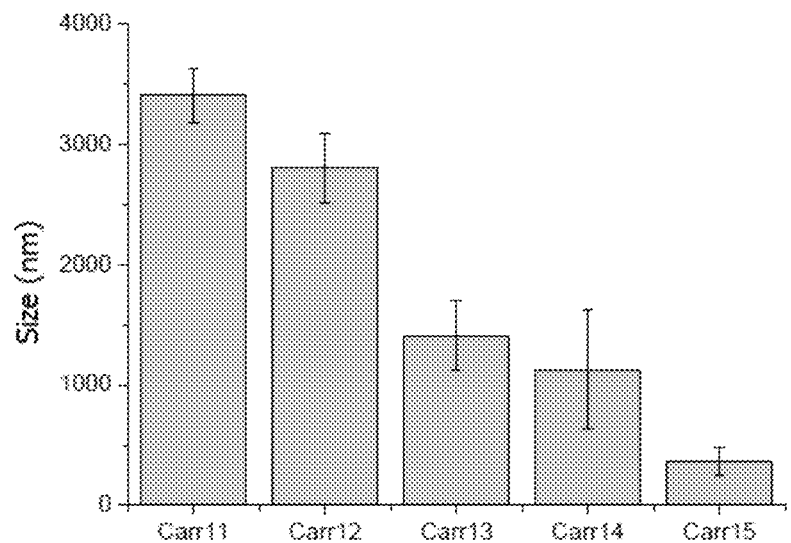
FIG. 21 shows the effect of the concentration of α-CD on the $D_h$ of the particles of O-palmitoyl-carrageenan DS2.
Figure 22:
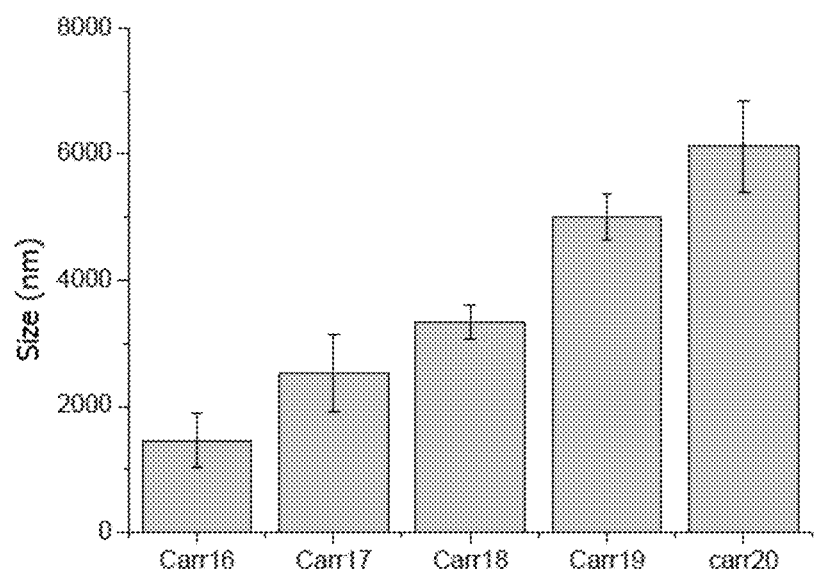
FIG. 22 shows the effect of the concentration of O-palmitoyl-carrageenan DS3 on the $D_h$ of the microparticles formed.

Effect of varying the concentration of α-CD on the hydrodynamic diameter of the microparticles and nanoparticles composed of carrageenan DS2
Variation in the quantity of α-cyclodextrin (FIG. 21)

| Name | Concentration of α-CD (g/L) | Concentration of O-palmitoyl-carrageenan DS2 (g/L) | Concentration ratio α-CD/O-palmitoyl-carrageenan DS2 | $D_h$ (nm) |
|---|---|---|---|---|
| Carr10 | 0 | 10 | 0 | No formation of particles, the product is insoluble in water |
| Carr11 | 100 | 10 | 10 | 3409 ± 226 |
| Carr12 | 50 | 10 | 5 | 2804 ± 288 |
| Carr13 | 25 | 10 | 2.5 | 1412 ± 290 |
| Carr14 | 10 | 10 | 1 | 1129 ± 491 |
| Carr15 | 5 | 10 | 0.5 | 365 ± 114 |

Example 19: Preparation and Characterization of Microparticles of O-Palmitoyl-Carrageenan DS3

O-Palmitoyl-carrageenan DS3 and α-cyclodextrin are weighed in a flask. Next, water is added to the mixture. The whole is mixed for 72 h at ambient temperature. The concentrations of O-palmitoyl-carrageenan and of α-cyclodextrin, and the results of the measurements of the hydrodynamic diameters, are shown in Table 11.

TABLE 11

Effect of varying the concentration of O-palmitoyl-carrageenan on the hydrodynamic diameter of the microparticles composed of carrageenan DS3
Variation in the quantity of O-palmitoyl-carrageenan DS3.

| Name | Concentration of α-CD (g/L) | Concentration of O-palmitoyl-carrageenan DS3 (g/L) | Concentration ratio α-CD/O-palmitoyl-carrageenan DS3 | $D_h$ (nm) |
|---|---|---|---|---|
| Carr16 | 100 | 2.5 | 40 | 1457 ± 431 |
| Carr17 | 100 | 5 | 20 | 2521 ± 612 |
| Carr18 | 100 | 10 | 10 | 3340 ± 265 |
| Carr19 | 100 | 20 | 5 | 5011 ± 371 |
| Carr20 | 100 | 30 | 3.3 | 6125 ± 730 |

Example 20: Manufacture of Microparticles and Nanoparticles Composed of N-Palmitoyl-Chitosan in the Presence of Castor Oil The microparticles and nanoparticles were formed from α-cyclodextrin and N-palmitoyl-chitosan MC9. The concentrations used are presented in the table below. The protocol consists of weighing N-palmitoyl-chitosan, α-cyclodextrin and castor oil labelled beforehand with Sudan III. The addition of Sudan III makes it possible to detect the phenomena of instability of the preparations. Next, water is added to the mixture. The whole is mixed for 72 h at ambient temperature.

The preparations observed by eye did not show phenomena of instability. The results of the measurements of size are presented in the following table.

TABLE 12

Effect of varying the concentration of castor oil on the hydrodynamic diameter of the microparticles and nanoparticles composed of chitosan MC9

| Concentration of α-CD (g/L) | Concentration of MC9 DS 17.01% (g/L) | Concentration of castor oil (g/L) | $D_h$ (nm) |
|---|---|---|---|
| 100 | 25 | 0 | 1416 ± 45 |
| 100 | 25 | 13 | 896 ± 44 |
| 100 | 25 | 23 | 964 ± 31 |

Example 21: Manufacture of Microparticles Composed of O-Oleoyl-Chitin in the Presence of Castor Oil The microparticles were formed from α-cyclodextrin and O-oleoyl-chitin DS 0.68%. The concentrations used are shown in the table below. The protocol consists of weighing O-oleoyl-chitin, α-cyclodextrin and castor oil labelled beforehand with Sudan III. The addition of Sudan III makes it possible to detect the phenomena of instability of the preparations. Next, water is added to the mixture. The whole is mixed for 72 h at ambient temperature. The preparations observed by eye did not show phenomena of instability. The results of the measurements of size are presented in the following table.

TABLE 13

Effect of varying the concentration of castor oil and the concentration of O-oleoyl-chitin on the hydrodynamic diameter of the microparticles

| Concentration of α-CD (g/L) | Concentration of O-oleoyl-chitin DS 0.68% (g/L) | Concentration of castor oil (g/L) | $D_h$ (nm) |
|---|---|---|---|
| 100 | 25 | 0 | 2734 ± 206 |
| 100 | 25 | 13 | 2057 ± 54 |
| 100 | 25 | 19.5 | 1875 ± 121 |
| 100 | 50 | 0 | 1487 ± 58 |
| 100 | 50 | 12 | 1579 ± 98 |
| 100 | 50 | 19.5 | 1310 ± 38 |

Example 22: Absence of the Formation of Particles Using Native Chitosan, not Grafted with Palmitic Acid α-Cyclodextrin (100 mg) and native chitosan (10 mg) were weighed in a vial. Next, water is added to the mixture to give a total volume of 1 mL. The whole is mixed using a magnetic stirring bar for 72 h at ambient temperature. FIG. 23 (1) is an image obtained after observations using transmission electron microscopy and shows the absence of formation of nanoparticles or of microparticles in comparison with the images of the nanoparticles obtained with O-palmitoyl-chitosan MC6/α-cyclodextrin/water (1/10/89)%.

Example 23: Drying of the Particles by Lyophilization

Lyophilization is a method of drying under vacuum at low temperature. The product containing water is frozen beforehand. Lyophilization is still the method of choice for drying heat-sensitive products.

The microparticles were prepared from α-cyclodextrin and N-oleoyl-chitosan, MC4, DS 13.47%. The protocol consists of weighing N-oleoyl-chitosan and α-cyclodextrin. The concentrations used are given in Table 14. Next, water is added to the mixture. The whole is mixed for 72 h at ambient temperature.

Lyophilization is carried out on 1 mL of preparation containing the microparticles, frozen beforehand at (−20° C.) for 12 h, and then placed in the lyophilizer for 24 h.

After being lyophilized, the preparations are resuspended in 1 mL of MilliQ® water; it is noted that the macroscopic appearance of the samples has not changed. In order to ensure that the lyophilization step had not altered the physicochemical characteristics of the particles, measurements of the hydrodynamic diameter were carried out after lyophilization and were compared with those obtained before lyophilization (Table 14).

TABLE 14

Measurement of the hydrodynamic diameters of the particles (of chitosan MC4: 145 kDa N-acylated with OA and a DS 13.47%) before and after lyophilization

| Concentration | | $D_h$ (nm) | |
|---|---|---|---|
| of N-oleoyl-chitosan (g/L) | Concentration of α-CD (g/L) | Before lyophilization | After lyophilization |
| 10 | 20 | 3050 ± 345 | 2880 ± 1102 |
| 10 | 100 | 1300 ± 139 | 1910 ± 173 |

Example 24: Scale-Up of Particle Manufacture

Transition to the pilot scale is a necessity for developing this method on an industrial scale. A pilot plant was designed composed of a reactor stirred with a mechanical stirrer of the propeller type. The stirring speed is fixed at 350 rpm. Regulation of the temperature at 25° C. is ensured by circulation of fluid (water/ethylene glycol) connected to a thermostat. 100-mL batches of microparticles are obtained by adding successively to the reactor (1 g) of chitosan of molecular weight 250 kDa N-acylated with 10 equivalents of palmitic acid (MC9, DS 17.01%), 10 g of α-cyclodextrin and MilliQ® water q.s. 100 mL.

The results obtained at the pilot scale are presented in Table 15 and compared with those obtained at the laboratory scale.

TABLE 15

Results of measurements of the hydrodynamic diameters of the microparticles obtained at the pilot scale in comparison with those obtained at the laboratory scale

| | Laboratory scale | Pilot scale |
|---|---|---|
| Final volume prepared | 2 mL | 100 mL |
| $D_h$ (nm) | 1680 ± 437 | 1730 ± 110 |

No significant change in $D_h$ was reported. The TEM images showed that the microparticles retained their hexagonal structure.

Example 25: Manufacture of Microparticles with a Mixture of Two Polysaccharides

TABLE 16

Hydrodynamic diameters of the microparticles composed of a mixture of O-palmitoyl-chitosan and O-palmitoyl-dextran

| Concentration of α-CD (g/L) | Concentration of O-palmitoyl-chitosan (g/L) | Concentration of O-palmitoyl-dextran (g/L) | $D_h$ (nm) |
|---|---|---|---|
| 100 | 7.6 | 2.5 | 1707 ± 122 |
| 100 | 2.5 | 7.5 | 3261 ± 230 |

TABLE 17

Hydrodynamic diameters of the microparticles composed of a mixture of O-palmitoyl-chitosan and O-palmitoyl-pullulan

| Concentration of α-CD (g/L) | Concentration of O-palmitoyl-chitosan (g/L) | Concentration of O-palmitoyl-pullulan (g/L) | $D_h$ (nm) |
|---|---|---|---|
| 100 | 7.7 | 2.5 | 2292 ± 89 |
| 100 | 5 | 5 | 2908 ± 112 |
| 100 | 2.5 | 7.5 | 2057 ± 271 |

TABLE 18

Hydrodynamic diameters of the microparticles composed of a mixture of O-palmitoyl-chitin and O-palmitoyl-dextran

| Concentration of α-CD (g/L) | Concentration of O-oleoyl-chitin (g/L) | Concentration of O-palmitoyl-dextran (g/L) | $D_h$ (nm) |
|---|---|---|---|
| 100 | 7.6 | 2.5 | 4899 ± 185 |
| 100 | 2.5 | 7.5 | 3960 ± 311 |

TABLE 20

Hydrodynamic diameters of the microparticles composed of a mixture of O-palmitoyl-chitin and O-palmitoyl-pullulan

| Concentration of α-CD (g/L) | Concentration of O-oleoyl-chitin (g/L) | Concentration of O-palmitoyl-pullulan (g/L) | $D_h$ (nm) |
|---|---|---|---|
| 100 | 5 | 5 | 3372 ± 283 |
| 100 | 2.5 | 7.5 | 3342 ± 210 |

Example 26: Antiviral Activity of the Nanoparticles Composed of O-Palmitoyl Heparin Cells. Kidney epithelial cells extracted from an African green monkey (Vero cells, (ATCC CCL-81), human epithelial cells Hep-2 and (ATCC CCL-23) and kidney epithelial cells extracted from an African green monkey (MA-104, ATCC CRL-2378.1) are cultured in monolayers in Eagle's minimum essential medium (MEM) (Gibco/BRL, Gaithersburg, Md.) supplemented with 10% of heat-inactivated fetal calf serum and 1% of antibiotic-antifungal solution (Zell Shield, Minerva Biolabs GmbH, Berlin, Germany). The 293TT cell line, derived from human embryonic kidney cells transformed with the large T antigen of simian virus 40 (SV40), is cultured in Dulbecco modified Eagle medium (DMEM) (Gibco-BRL, Gaithersburg, Md.) supplemented with 10% of fetal calf serum (FCS; Gibco-BRL), Glutamax-I 1% (Invitrogen, Carlsbad, Calif.) and 1% of non-essential amino acids (Sigma Aldrich, Steinheim, Germany). The 293TT cells allow expression of a high level of proteins from vectors containing the replication origin of SV40 owing to over-replication of the expression vectors (Buck et al., 2004).

Virus. Clinical isolates of HSV-1 and HSV-2 were supplied by Professor M. Pistello (University of Pisa, Italy). The HSV-1 and HSV-2 strains were propagated and titrated by the plating technique on Vero cells. The strain A2 RSV (ATCC VR-1540) was propagated and titrated by the Reed-Muench method on Hep-2 cells described previously (Donalisio et al., 2012). The strain of human rotavirus Wa(ATCC VR-2018) was activated with 5 µg/ml of porcine pancreatic trypsin of the IX type (Sigma, St. Louis, Mo.) for 30 min at 37° C. and propagated in MA104 cells using MEM medium containing 0.5 µg of trypsin per ml as described previously (Coulson et al., 1986). The stocks of virus were kept frozen (−80° C.).

HPV PsV production. The plasmids and 293TT cells used for producing pseudovirus (PsV) were supplied by John Schiller (National Cancer Institute, Bethesda, Md.). The details of the protocols and the maps of the plasmids of this study may be consulted on the following link: http://home.c-cr.cancer.gov/lco/default.asp. HPV-16 pseudoviruses were produced by methods described previously (Buck et al., 2005). Briefly, the 293TT cells are transfected with plasmids expressing the proteins of major and minor capsids of papillomaviruses (respectively L1 and L2) and a reporter plasmid expressing secreted alkaline phosphatase (SEAP), pYSEAP. The capsids were matured overnight in a cellular lysate, and the clarified supernatant was then loaded above a density gradient from 27 to 33 to 39%, Optiprep (Sigma-Aldrich, St. Louis, Mo.), at ambient temperature for 4 h. The material was then centrifuged at 340,000 g for 3.5 h at 16° C. in an SW50.1 rotor (Beckman Coulter, Inc., Fullerton, Calif.) and then collected by puncture at the bottom of the tubes. The fractions are analysed for purity in gels of glycine-Tris-10% Sodium Dodecyl Sulphate (SDS), titrated on 293TT cells to test infectivity by detection with SEAP, and then combined and frozen at −80° C. for the desired time. The content of protein L1 of the stocks of PsV was determined by comparison with standard bovine serum albumin on polyacrylamide-SDS gels stained with Coomassie Blue.

TABLE 21

Values of the median effective concentration (EC50) in µg/mL.

| | Hep2 | Hep3 | Hep4 | Hep8 |
|---|---|---|---|---|
| HSV-1 | 0.99 | 1.25 | 1.13 | 6.61 |
| HSV-2 | 0.65 | 0.83 | 1.22 | 3.65 |
| HPV-16 | 1.96 | 0.24 | 3.95 | 2.55 |
| RSV | 0.24 | 0.28 | 0.27 | 0.36 |
| Rotavirus | — | — | — | — |

Example 27: Absence of the Formation of Particles Using the Derivatives of β-Cyclodextrin and O-Palmitoyl-Chitosan (MC12)

TABLE 22

Absence of the formation of particles by mixing O-palmitoyl-chitosan (MC12) with HP-β-CD or Me-β-CD

| CD used | Concentration of MC12 (g/L) | Concentration of CD (g/L) | Appearance of the preparation |
|---|---|---|---|
| HP-β-CD | 1.25 | 100 | Large insoluble white aggregates |
| | 2.5 | 100 | |
| | 5 | 100 | |
| | 5 | 10 | |
| | 5 | 15 | |
| | 5 | 20 | |
| | 5 | 25 | |
| | 5 | 50 | |
| Me-β-CD | 2.5 | 100 | |
| | 5 | 100 | |
| | 10 | 100 | |
| | 5 | 10 | |
| | 5 | 15 | |
| | 5 | 20 | |
| | 5 | 25 | |
| | 5 | 50 | |

Example 28: Absence of the Formation of Particles Using the Derivatives of β-Cyclodextrin and O-Oleoyl-Chitin

TABLE 23

Absence of the formation of particles using the derivatives of β-cyclodextrin and O-oleoyl-chitin

| CD used | Concentration O-oleoyl-chitin DS 0.1% (g/L) | Concentration CD (g/L) | Appearance of the preparation |
|---|---|---|---|
| HP-β-CD | 2.5 | 100 | Large white aggregates |
| | 5 | 100 | |
| | 10 | 100 | |
| | 5 | 10 | |
| | 5 | 15 | |
| | 5 | 20 | |
| | 5 | 25 | |
| Me-β-CD | 2.5 | 100 | White aggregates |
| | 5 | 100 | |
| | 10 | 100 | |
| | 5 | 10 | |
| | 5 | 15 | |
| | 5 | 20 | |
| | 5 | 25 | |
| | 5 | 50 | |

Example 29: Absence of the Formation of Particles Using the Derivatives of β-Cyclodextrin and O-Palmitoyl-Pullulan

TABLE 24

Absence of the formation of particles using the derivatives of β-cyclodextrin and O-palmitoyl-pullulan

| CD used | Concentration of O-palmitoyl-pullulan (g/L) | Concentration CD (g/L) | Appearance of the preparation |
|---|---|---|---|
| HP-β-CD | 2.5 | 100 | Solution: dissolution of O-palmitoyl-pullulan |
| | 5 | 100 | White aggregates |
| | 10 | 100 | |
| | 5 | 10 | |
| | 5 | 15 | |
| | 5 | 20 | |
| | 5 | 25 | |
| Me-β-CD | 2.5 | 100 | |
| | 5 | 100 | |
| | 10 | 100 | |
| | 5 | 10 | |

Example 30: Preparation and Characterization of Microparticles of O-Palmitoyl-Hyaluronic Acid O-Palmitoyl-hyaluronic acid and α-cyclodextrin are weighed in a flask. Next, water is added to the mixture. The whole is mixed for 72 h at ambient temperature. The concentration of α-cyclodextrin and the results of the measurements of the hydrodynamic diameters are shown in Table 25.

TABLE 25

Effect of varying the concentration of α-CD on the size of the microparticles consisting of O-palmitoyl-hyaluronic acid

| Concentration of α-CD (g/L) | Concentration of O-palmitoyl-hyaluronic acid (g/L) | Concentration ratio α-CD/O-palmitoyl-acid hyaluronic | $D_h$ (nm) |
|---|---|---|---|
| 0 | 10 | 0 | Absence of the formation of particles, presence of large insoluble aggregates |
| 25 | 10 | 2.5 | 1946 ± 589 |
| 100 | 10 | 10 | 2479 ± 334 |

Example 31: Encapsulation of the Active Ingredients in the Presence of a Solvent The protocol adopted for encapsulating the hydrophobic active ingredients is to dissolve the active ingredient in an ethanol/water mixture at an initial concentration as shown in Table 26 and then add the amphiphilic polysaccharide and the α-cyclodextrin. The mixture is maintained under magnetic stirring for 3 days. After mixing for 3 days, the concentration of the active ingredient that has not been encapsulated is determined in the supernatant of the preparation. The supernatant is separated either by simple sedimentation or by centrifugation of the microparticles, or after ultracentrifugation in the case of the nanoparticles.

TABLE 26

Example of encapsulated active molecules.

| | Ethanol/ water % v/v | Polysaccharide used | Initial concentration of active molecules (g/L) | Encapsulated concentration (g/L) | Encapsulation yield (%) |
|---|---|---|---|---|---|
| Ketoprofen | 40/60 | MC6 | 3.5 | 1.09 | 31.12 |

The invention claimed is:

1. An inclusion complex formed by interaction in solvent between at least:
   one polysaccharide selected from the group consisting of chitosan, dextran, hyaluronic acid, amylose, amylopectin, pullulan, heparin, chitin, heparan sulphate, dermatan sulphate, keratan sulphate, chondroitin sulphate, cellulose sulphate, dextran sulphate, dextrin sulphate, starch, pectin, the alginates, the carrageenans, fucan, curdlan, xylan, polyguluronic acid, xanthan, arabinan, and polymannuronic acid, said polysaccharide comprising hydrophobic groups selected from linear or branched alkyl groups containing from 2 to 1000 carbon atoms, or linear or branched alkenyl groups, which contain at least one C=C double bond, said hydrophobic groups being bound covalently to said polysaccharide such that said polysaccharide is amphiphilic, and
   one α-cyclodextrin (CD) in the form of monomer,
   wherein the polysaccharide and the cyclodextrin are bound non-covalently, and
   wherein the polysaccharide and the cyclodextrin are present in a ratio of concentration of the cyclodextrin in g/L of the solvent to concentration of polysaccharide in g/L of the solvent in a range from 3.3 to 40.

2. The inclusion complex according to claim 1, wherein the polysaccharide is composed of at least 3 saccharide units, the polysaccharide having a molecular weight in the range from 100 Da to 1,000,000 kDa, and wherein the polysaccharide has a degree of substitution with the hydrophobic groups from 0.001 to 100%.

3. The inclusion complex according to claim 1, wherein:
   the polysaccharide is a chitosan bearing hydrophobic groups at the level of oxygen atoms originating from the —OH groups and/or from the —CH$_2$OH groups fixed to the chitosan ring, and having the formula

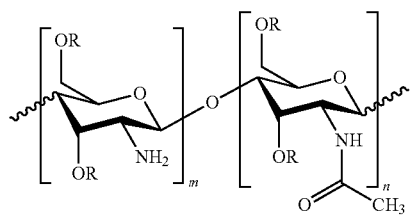

in which
R represents
   a hydrogen atom, or
   a group of formula

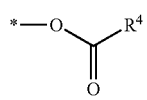

in which
R$^4$ represents the hydrophobic group and is selected from:
   a linear or branched alkyl group containing from 1 to 1000 carbon atoms, and a linear or branched alkenyl group containing 2 to 1000 carbon atoms and containing at least one C=C double bond, provided that R represents at least one group of formula

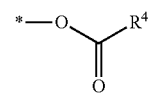

m represents the number of D-glucosamine units,
n represents the number of N-acetyl-D-glucosamine units, provided that the degree of deacetylation (DDA) representing the percentage of m relative to the total number of units is greater than 50%,
and the α-cyclodextrin CD has the formula

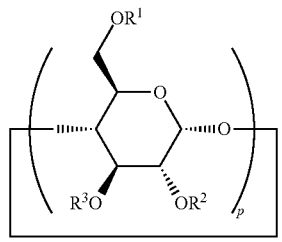

in which
   p is equal to 6,
   R$^1$, R$^2$ and R$^3$, which are identical or different, are hydrogen atoms, alkyl groups comprising 1 to 3 carbon atoms, selected from methyls, ethyls, propyls, isopropyls, —NH$_2$ amino groups, —NH$_3^+$ ammonium groups, or —SO$_4^{2-}$ sulphate groups, said CD being alpha-cyclodextrin (α-CD) in the form of monomer.

4. The inclusion complex according to claim 1, wherein the polysaccharide is selected from the group consisting of:
   the polysaccharide is a dextran bearing hydrophobic groups, fixed by oxygen atoms of said dextran and representing groups of formula

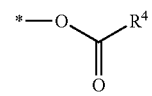

in which
R$^4$ has the meanings designated above,
* represents dextran,
   the polysaccharide is hyaluronic acid bearing hydrophobic groups, fixed by oxygen atoms of said hyaluronic acid and representing groups of formula

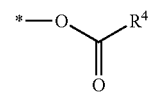

in which
R⁴ has the meanings designated above,
* represents hyaluronic acid,
the polysaccharide is an amylopectin bearing hydrophobic groups fixed by oxygen atoms of said amylopectin and representing groups of formula

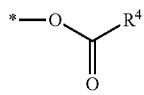

in which
R⁴ has the meanings designated above,
* represents an amylopectin,
the polysaccharide is a pullulan bearing hydrophobic groups fixed by oxygen atoms of said pullulan and representing groups of formula

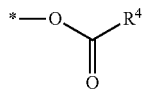

in which
R⁴ has the meanings designated above,
* represents pullulan,
the polysaccharide is a heparin bearing hydrophobic groups fixed by nitrogen atoms of said heparin and representing groups of formula

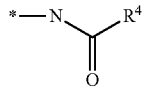

in which
R⁴ has the meanings designated above,
* represents heparin,
the polysaccharide is a heparin bearing hydrophobic groups fixed by oxygen atoms of said heparin, these oxygens originating from the hydroxyl or carboxyl groups of the heparin, and representing groups of formula

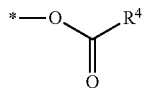

in which
R⁴ has the meanings designated above,
* represents heparin,
the polysaccharide is a carrageenan bearing hydrophobic groups fixed by nitrogen atoms of said carrageenan sulphate and representing groups of formula

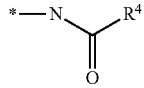

in which
R⁴ has the meanings designated above,
* represents carrageenan, and
the polysaccharide is a carrageenan bearing hydrophobic groups fixed by oxygen atoms of said carrageenan, these oxygens originating from the hydroxyl or carboxyl groups of carrageenan, and representing groups of formula

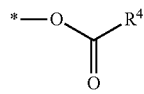

in which
R⁴ has the meanings designated above,
* represents carrageenan.

5. A particle with a size in the range from 1 nm to 100,000 nm containing inclusion complexes according to claim 1.

6. An encapsulation system comprising one or more particles according to claim 5 that encapsulate a substance having pharmaceutical properties.

7. A pharmaceutical composition containing a substance having pharmaceutical properties encapsulated in the inclusion complex according to claim 1 or in particles with a size in the range from 1 nm to 100,000 nm containing said inclusion complex, together with a pharmaceutically acceptable vehicle, in solid form, or in the form of solution or suspension in a physiological medium.

8. A method for preparing an inclusion complex according to claim 1, comprising a step of mixing at least:
one polysaccharide in the form of a suspension in a solvent, comprising hydrophobic groups bound covalently to the polysaccharide by oxygen atoms of said polysaccharide such that that said polysaccharide is amphiphilic,
and one α-cyclodextrin (CD) in the form of monomer, to obtain an inclusion complex, wherein said polysaccharide and said cyclodextrin are bound non-covalently,
wherein the polysaccharide and the cyclodextrin are present in a ratio of concentration of the cyclodextrin in g/L of the solvent to concentration of polysaccharide in g/L of the solvent in a range from 3.3 to 40, and wherein:
the polysaccharide is selected from the group consisting of chitosan, dextran, hyaluronic acid, amylose, amylopectin, pullulan, heparin, chitin, heparan sulphate, dermatan sulphate, keratan sulphate, chondroitin sulphate, cellulose sulphate, dextran sulphate, dextrin sulphate, starch, pectin, the alginates, the carrageenans, fucan, curdlan, xylan, polyglucuronic acid, xanthan, arabinan, and polymannuronic acid, said polysaccharide comprising hydrophobic groups of formula

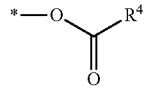

in which
* represents the polysaccharide,
R⁴ represents
a linear or branched alkyl group containing from 1 to 1000 carbon atoms,
a linear or branched alkenyl group containing 2 to 1000 carbon atoms and bearing
at least one C=C double bond, an α-cyclodextrin (CD) having the formula

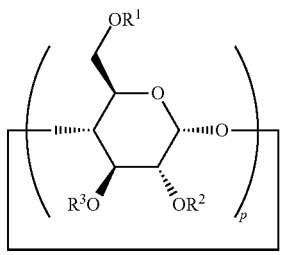

in which
p is equal to 6,
R$^1$, R$^2$ and R$^3$, which are identical or different, are hydrogen atoms, alkyl groups comprising 1 to 3 carbon atoms, selected from methyls, ethyls, propyls, isopropyls, —NH$_2$ amino groups, —NH$_3$ ammonium groups, or —SO$_4^{2-}$ sulphate groups, said CD being alpha-cyclodextrin (α-CD) in the form of monomer.

9. A cosmetic composition, comprising particles according to claim 5.

10. The inclusion complex according to claim 2, wherein the molecular weight is equal to 20 kDa, 145 kDa or 250 kDa.

11. The inclusion complex according to claim 1, wherein the ratio of the concentration of cyclodextrin in g/L of the solvent to that of the polysaccharide in g/L of the solvent is in the range from 4 to 15.

12. The inclusion complex according to claim 3, wherein R4 is selected from the group consisting of —(CH$_2$)$_{14}$—CH$_3$, —(CH$_2$)$_{16}$—CH$_3$, —(CH$_2$)$_7$—CH=CH—CH$_2$—(CH$_2$)$_7$—CH$_3$ and —(CH$_2$)$_7$—CH=CH—(CH$_2$)$_7$—CH$_3$.

13. An encapsulation system comprising one or more particles according to claim 5 that encapsulate a substance having cosmetic properties.

* * * * *